(12) United States Patent
Taghioskoui

(10) Patent No.: US 12,089,932 B2
(45) Date of Patent: Sep. 17, 2024

(54) APPARATUS, SYSTEM, AND METHOD FOR TRANSFERRING IONS

(71) Applicant: Trace Matters Scientific LLC, Somerville, MA (US)

(72) Inventor: Mazdak Taghioskoui, Somerville, MA (US)

(73) Assignee: Trace Matters Scientific LLC, North Bethesda, MD (US)

( * ) Notice: Subject to any disclaimer, the term of this patent is extended or adjusted under 35 U.S.C. 154(b) by 339 days.

(21) Appl. No.: 17/570,235

(22) Filed: Jan. 6, 2022

(65) Prior Publication Data
US 2022/0202317 A1  Jun. 30, 2022

Related U.S. Application Data

(63) Continuation of application No. 16/509,016, filed on Jul. 11, 2019, now Pat. No. 11,219,393, which is a
(Continued)

(51) Int. Cl.
*A61B 5/1473* (2006.01)
*A61B 5/00* (2006.01)
(Continued)

(52) U.S. Cl.
CPC .......... *A61B 5/1473* (2013.01); *A61B 5/4842* (2013.01); *A61B 10/04* (2013.01);
(Continued)

(58) Field of Classification Search
CPC ... A61B 5/1473; A61B 5/4842; A61B 5/0077; A61B 5/444; A61B 5/6851;
(Continued)

(56) References Cited

U.S. PATENT DOCUMENTS

| 4,988,879 A | 1/1991 | Zare et al. |
| 5,572,035 A | 11/1996 | Franzen |

(Continued)

FOREIGN PATENT DOCUMENTS

| EP | 1566828 | 2/2005 |
| EP | 1825495 | 11/2011 |

(Continued)

OTHER PUBLICATIONS

Balog, Julia, et al. "Identification of the species of origin for meat products by rapid evaporative ionization mass spectrometry" Journal of agricultural and food chemistry 64.23 (2016) 4793-4800.
(Continued)

*Primary Examiner* — Kiet T Nguyen
(74) *Attorney, Agent, or Firm* — Lee & Hayes, P.C.

(57) ABSTRACT

An ion transfer device that includes first and second ion guides, one or more RF voltage sources, and one or more DC voltage sources that produce first and second potential gradients in the first and second ion guides such that the potential gradients push the ions to move toward the outlet of each ion guide such that the one or more DC voltages produce a potential barrier, the potential barrier preventing the ions in the first ion guide from entering the second ion guide, the ions accumulate behind the potential barrier and form an ion packet, and the potential barrier is reduced after a predetermined time period to move the ion packet from the first ion guide to the second ion guide.

62 Claims, 55 Drawing Sheets

Related U.S. Application Data continuation-in-part of application No. 16/350,396, filed on Jul. 12, 2018, now Pat. No. 10,840,077.

(60) Provisional application No. 62/680,592, filed on Jun. 5, 2018, provisional application No. 62/838,076, filed on Apr. 24, 2019, provisional application No. 62/855,089, filed on May 31, 2019.

(51) Int. Cl.

| | | |
|---|---|---|
| *A61B 10/04* | (2006.01) | |
| *G01N 27/622* | (2021.01) | |
| *G01N 33/483* | (2006.01) | |
| *H01J 49/00* | (2006.01) | |
| *H01J 49/06* | (2006.01) | |
| *H01J 49/16* | (2006.01) | |
| *H01J 49/36* | (2006.01) | |
| *H01J 49/42* | (2006.01) | |
| *A61B 18/00* | (2006.01) | |
| *A61B 18/24* | (2006.01) | |

(52) U.S. Cl.
CPC ....... *G01N 27/622* (2013.01); *G01N 33/4833* (2013.01); *H01J 49/0013* (2013.01); *H01J 49/0031* (2013.01); *H01J 49/065* (2013.01); *H01J 49/164* (2013.01); *H01J 49/165* (2013.01); *H01J 49/36* (2013.01); *H01J 49/4235* (2013.01); *A61B 2018/00577* (2013.01); *A61B 18/24* (2013.01); *A61B 2218/007* (2013.01); *A61B 2503/40* (2013.01)

(58) Field of Classification Search
CPC ....... A61B 5/6887; A61B 10/04; A61B 18/24; A61B 18/203; A61B 18/26; A61B 18/22; A61B 2018/00577; A61B 2018/00327; A61B 2018/00488; A61B 2018/00494; A61B 2018/00505; A61B 2018/00982; A61B 2018/00476; A61B 2018/00559; A61B 2018/2035; A61B 2018/2211; A61B 2218/007; A61B 2503/40; G01N 27/622; G01N 33/4833; H01J 49/0013; H01J 49/0031; H01J 49/0404; H01J 49/065; H01J 49/164; H01J 49/165; H01J 49/36; H01J 49/4235; H01J 49/068; H01J 49/062

USPC .................................................. 250/281, 282
See application file for complete search history.

(56) References Cited

U.S. PATENT DOCUMENTS

| | | | |
|---|---|---|---|
| 6,107,328 A | 8/2000 | Parsons | |
| 6,107,628 A | 8/2000 | Smith et al. | |
| 6,231,054 B1 | 5/2001 | Allen, Jr. et al. | |
| 6,369,383 B1 | 4/2002 | Cornish et al. | |
| 6,583,408 B2 | 6/2003 | Smith et al. | |
| 6,849,848 B2 | 2/2005 | Baranov et al. | |
| 6,960,760 B2 | 11/2005 | Bateman et al. | |
| 7,365,317 B2 | 4/2008 | Whitehouse et al. | |
| 7,391,021 B2 | 6/2008 | Stoermer et al. | |
| 7,423,261 B2 | 9/2008 | Truche et al. | |
| 7,492,822 B2 | 2/2009 | Cotton et al. | |
| 7,700,913 B2 | 4/2010 | Musselman | |
| 7,705,297 B2 | 4/2010 | Musselman | |
| 7,786,435 B2 | 8/2010 | Whitehouse et al. | |
| 7,838,826 B1 | 11/2010 | Park | |
| 7,888,635 B2 | 2/2011 | Belov et al. | |
| 7,919,747 B2 | 4/2011 | Green et al. | |
| 7,928,364 B2 | 4/2011 | Musselman | |
| 7,982,183 B2 | 7/2011 | Makarov et al. | |
| 8,008,617 B1 | 8/2011 | Berends, Jr. et al. | |
| 8,022,358 B2 | 9/2011 | Green | |
| 8,049,169 B2 | 11/2011 | Satake et al. | |
| 8,222,597 B2 | 7/2012 | Kim et al. | |
| 8,227,748 B2 | 7/2012 | Berg et al. | |
| 8,242,440 B2 | 8/2012 | Splendore et al. | |
| 8,286,260 B2 | 10/2012 | Vertes et al. | |
| 8,309,916 B2 | 11/2012 | Wouters et al. | |
| 8,507,848 B1 | 8/2013 | Ding et al. | |
| 8,591,459 B2 | 11/2013 | Clymer et al. | |
| 8,637,817 B1 | 1/2014 | Krutchinsky et al. | |
| 8,759,757 B2 | 6/2014 | Hardman et al. | |
| 8,835,839 B1 | 9/2014 | Anderson et al. | |
| 8,969,800 B1 | 3/2015 | Tolmachev et al. | |
| 9,006,647 B2 | 4/2015 | Kenny et al. | |
| 9,046,448 B2 | 6/2015 | Takats | |
| 9,281,174 B2 | 3/2016 | Takats | |
| 9,324,548 B1 | 4/2016 | Benter et al. | |
| 9,396,919 B2 | 7/2016 | Makarov et al. | |
| 9,966,244 B2 | 5/2018 | Anderson et al. | |
| 10,254,275 B2 | 4/2019 | Salzet et al. | |
| 10,460,920 B1 | 10/2019 | Smith et al. | |
| 10,840,077 B2 | 11/2020 | Taghioskoui | |
| 11,031,232 B1 | 6/2021 | Stewart et al. | |
| 11,222,776 B1 | 1/2022 | Taghioskoui | |
| 11,600,480 B2 | 3/2023 | Nieto Ramos et al. | |
| 11,756,779 B2 | 9/2023 | Taghioskoui | |
| 2001/0020679 A1 | 9/2001 | Franzen | |
| 2004/0026611 A1 | 2/2004 | Bateman et al. | |
| 2007/0138384 A1 | 6/2007 | Keiser | |
| 2007/0158545 A1* | 7/2007 | Verentchikov | H01J 49/004 250/282 |
| 2007/0278397 A1* | 12/2007 | Bateman | H01J 49/062 250/296 |
| 2008/0116370 A1 | 5/2008 | Splendore et al. | |
| 2008/0142698 A1 | 6/2008 | Atherton et al. | |
| 2008/0308721 A1 | 12/2008 | Senko et al. | |
| 2009/0045330 A1 | 2/2009 | Wang et al. | |
| 2009/0159790 A1 | 6/2009 | Kostiainen et al. | |
| 2009/0173880 A1 | 7/2009 | Bateman et al. | |
| 2009/0206250 A1 | 8/2009 | Wollnik | |
| 2009/0321655 A1 | 12/2009 | Makarov et al. | |
| 2011/0024618 A1 | 2/2011 | Brown et al. | |
| 2011/0049357 A1 | 3/2011 | Giles | |
| 2011/0101216 A1 | 5/2011 | Musselman | |
| 2011/0168882 A1 | 7/2011 | Hoyes | |
| 2011/0186724 A1 | 8/2011 | Nolting et al. | |
| 2011/0192969 A1 | 8/2011 | Verentchikov | |
| 2011/0240844 A1 | 10/2011 | Ouyang et al. | |
| 2011/0266434 A1 | 11/2011 | Li et al. | |
| 2011/0295250 A1 | 12/2011 | Johnson et al. | |
| 2012/0153141 A1 | 6/2012 | Wouters et al. | |
| 2012/0261570 A1 | 10/2012 | Shvartsburg et al. | |
| 2012/0312979 A1 | 12/2012 | Cooks et al. | |
| 2013/0175440 A1 | 7/2013 | Perelman et al. | |
| 2013/0206973 A1 | 8/2013 | Kovtoun et al. | |
| 2013/0306861 A1 | 11/2013 | Papanastasiou et al. | |
| 2014/0276201 A1 | 9/2014 | Woloszko et al. | |
| 2015/0076343 A1 | 3/2015 | Tolmachev et al. | |
| 2015/0155150 A1* | 6/2015 | Bateman | H01J 49/0031 250/283 |
| 2015/0287578 A1 | 10/2015 | Bendall et al. | |
| 2015/0338413 A1 | 11/2015 | Agar | |
| 2015/0364309 A1* | 12/2015 | Welkie | H01J 49/063 250/288 |
| 2016/0181080 A1 | 6/2016 | Williams | |
| 2016/0225598 A1 | 8/2016 | Ristroph | |
| 2016/0322209 A1 | 11/2016 | Wouters et al. | |
| 2016/0341712 A1 | 11/2016 | Agar | |
| 2017/0076931 A1 | 3/2017 | Ibrahim et al. | |
| 2017/0184552 A1 | 6/2017 | Guzzonato et al. | |
| 2017/0350860 A1 | 12/2017 | Rather et al. | |
| 2018/0049643 A1 | 2/2018 | Balog et al. | |
| 2018/0103935 A1 | 4/2018 | Pringle et al. | |
| 2018/0158661 A1 | 6/2018 | Eberlin et al. | |
| 2018/0238776 A1 | 8/2018 | Karancsi et al. | |
| 2018/0271502 A1 | 9/2018 | Zarrine-Afsar et al. | |
| 2018/0323050 A1* | 11/2018 | Smith | H01J 49/4225 |
| 2019/0267221 A1 | 8/2019 | Pringle et al. | |

(56) References Cited

U.S. PATENT DOCUMENTS

| | | |
|---|---|---|
| 2019/0371591 A1 | 12/2019 | Taghioskoui |
| 2020/0015717 A1 | 1/2020 | Taghioskoui |
| 2020/0111655 A1 | 4/2020 | Taghioskoui |
| 2022/0208536 A1 | 6/2022 | Taghioskoui |
| 2023/0118221 A1 | 4/2023 | Stewart et al. |

FOREIGN PATENT DOCUMENTS

| | | |
|---|---|---|
| EP | 3038134 | 12/2015 |
| EP | 3252460 | 4/2017 |
| GB | 2499587 | 8/2013 |
| WO | WO2016034125 | 3/2016 |
| WO | WO2017182794 | 10/2017 |
| WO | WO2018048494 | 3/2018 |
| WO | WO2019104328 | 5/2019 |

OTHER PUBLICATIONS

Balog, Julia, et al. "In vivo endoscopic tissue identification by rapid evaporative ionization mass spectrometry (REIMS)" Angewandte Chemie International Edition 54.38 (2015) 11059-11062.

Balog, Julia, et al. "Intraoperative tissue identification using rapid evaporative ionization mass spectrometry" Science translational medicine 5.194 (2013) 194ra93-194ra93.

Brown, Hannah Marie, Valentina Pirro, and R. Graham Cooks. "From DESI to the MasSpec Pen Ambient Ionization Mass Spectrometry for Tissue Analysis and Intrasurgical Cancer Diagnosis" Clinical chemistry 64.4 (2018) 628-630.

Chen, Chien-Hsun, et al. "Development of a mass spectrometry sampling probe for chemical analysis in surgical and endoscopic procedures" Analytical chemistry 85.24 (2013) 11843-11850.

Chen, Lee Chuin, et al. "In vivo endoscopic mass spectrometry using a moving string sampling probe" Analyst 142.15 (2017) 2735-2740.

Chen, Lee Chuin, et al. "Towards Practical Endoscopic Mass Spectrometry" Mass Spectrometry 6.3 (2017) S0070-S0070.

Clemett, Simon J., and Richard N. Zare. "Microprobe two-step laser mass spectrometry as an analytical tool for meteoritic samples" Symposium—International Astronomical Union. vol. 178. Cambridge University Press, 1997.

Ehlert, Sven, et al., "Rapid on-site detection of explosives on surfaces by ambient pressure laser desorption and dlirect inlet single photon ionization or chemical ionization mass spectrometry", Anal Bioanal Chem, 2013, pp. 5979-6993, Springer.

Garimella et al., "Simulation of Electric Potentials and Ion Motion in Planar Electrode Structures for Lossless Ion Manipulations (SLIM)," J. Am. Soc. Mass Spectrom. 25(11):1890-1896 (Nov. 2014).

Giles et al., "A method for direct measurement of ion mobilities using a travelling wave ion guide," International Journal of Mass Spectrometry, 298(1): 10-16 (Dec. 2010).

Giles et al., "Enhancements in travelling wave ion mobility resolution," Rapid Commun. Mass Spectrom., 25(11):1559-1566 (Jun. 15, 2011).

Glaskin et al., "Ion Trapping for Ion Mobility Spectrometry Measurements in a Cyclical Drift Tube," Anal. Chem., 85(15):7003-7008 (Jul. 2013).

Gundogdu, Yasemin, et al. "Discrimination of cancerous and healthy colon tissues: A new laser-based method" Lasers in surgery and medicine 51.4 (2019) 363-369.

Hahn, Jong Hoon, et al. "Application of two-step laser mass spectrometry to cosmogeochemistry: Direct analysis of meteorites" Science 239.4847 (1988) 1523-1525.

Hamid et al., "Characterization of Traveling Wave Ion Mobility Separations in Structures for Lossless Ion Manipulations," Anal. Chem., 87: 11301-11308 (Oct. 28, 2015).

Hanel, Lorena, et al. "Mass spectrometry-based intraoperative tumor diagnostics" Future science OA 5.3 (2019) FSO373.

Hars, et. al., "Flexible ion conduit for use under rarefied atmospheric conditions", Review of Scientific Instruments 68, 3351 (1997), Jun. 4, 1998; entire document; especially Fig. 2, 3, pp. 3351-3354; < https://aip.scitation.org/doi/abs/10.1063/1.1148296 > last visited May 27, 2020.

Hendricks, Paul I, et al., "Autonomous in Situ Analysis and Real-Time Chemical Detection Using a Backpack Miniature Mass Spectrometer: Concept, Instrumentation Development, and Performance" Analytical Chemistry, 2014, pp. 2900-2908, 86, ACS Publications.

Ho, Ying-Ning, Lin-Jie Shu, and Yu-Liang Yang. "Imaging mass spectrometry for metabolites: technical progress, multimodal imaging, and biological interactions" Wiley Interdisciplinary Reviews Systems Biology and Medicine 9.5 (2017) e1387.

Ibrahim et al., "Development of a new ion mobility (quadrupole) time-of-flight mass spectrometer," International Journal of Mass Spectrometry, 377:655-662 (Feb. 1, 2015).

Ibrahim et al., "New frontiers for mass spectrometry based upon structures for lossless ion manipulations," The Analysyst, 142(7):1010-1021, Mar. 3, 2017, 24 pages.

Ifa, Demian R., and Livia S. Eberlin. "Ambient ionization mass spectrometry for cancer diagnosis and surgical margin evaluation" Clinical chemistry 62.1 (2016) 111-123.

Jarmusch, Alan K., et al. "Lipid and metabolite profiles of human brain tumors by desorption electrospray ionization-MS" Proceedings of the National Academy of Sciences 113.6 (2016) 1486-1491.

Kim, Jae Young, et al. "Atmospheric pressure mass spectrometric imaging of live hippocampal tissue slices with subcellular spatial resolution" Nature communications 8.1 (2017) 2113.

Li, Li-Hua, Hua-Yi Hsieh, and Cheng-Chih Hsu. "Clinical application of ambient ionization mass spectrometry" Mass Spectrometry 6.2 (2017) S0060-S0060.

Merenbloom et al., "Effects of Select Anions from the Hofmeister Series on the Gas-Phase Conformations of Protein Ions Measured with Traveling-Wave Ion Mobility Spectrometry/Mass Spectrometry," J. Am. Soc. Mass Spectrom. 22:1978-1990 (Nov. 22, 2011).

Non Final Office Action dated Jan. 7, 2020 for U.S. Appl. No. 16/151,162 "Reconfigurable Sequentially-Packed Ion (SPION) Transfer Device" Taghioskoui, 9 pages.

Office Action for U.S. Appl. No. 17/071,458, mailed on May 27, 2021, Taghioskoui, "Ion Analysis System and Method With Multiple Ionization Sources and Analyzers", 5 Pages.

Office Action for U.S. Appl. No. 16/509,016, mailed on Feb. 22, 2021, Taghioskoui, "Reconfigurable Sequentially-Packed Ion (Spion) Transfer Device and System", 10 pages.

Non Final Office Action dated May 1, 2020 for U.S. Appl. No. 16/350,396 "Reconfigurable Sequentially-Packed Ion (SPION) Transfer Device" Taghioskoui, 10 pages.

Office Action for U.S. Appl. No. 16/151,162, mailed on Jun. 26, 2019, Taghioskoui, "Reconfigurable Sequentially-Packed Ion (SPION) Transfer Device", 7 pages.

PCT Search Report and Written Opinion mailed on May 22, 2020 for PCT Application No. PCT/IB19/55944, 15 pages.

Phelps, David L., et al. "The surgical intelligent knife distinguishes normal, borderline and malignant gynaecological tissues using rapid evaporative ionisation mass spectrometry (REIMS)" British journal of cancer 118.10 (2018) 1349.

Pringle et al., "An investigation of the mobility separation of some peptide and protein ions using a new hybrid quadrupole/travelling wave IMS/oa-ToF instrument," International Journal of Mass Spectrometry, 261 (1):1-12 (Mar. 1, 2007).

Schelten, J et al., "Properties an limitations of an Ion Guide, Nuclear Instruments and Methods in Physics Research" A292, 1990, 45-51, North Holland, Elsevier Science Publishers BY.

Shvartsburg et al., "Fundamentals of Traveling Wave Ion Mobility Spectrometry," Anal. Chem., 80(24):9689-9699 (Dec. 15, 2008).

Smith et al., "Deciphering drift time measurements from travelling wave ion mobility spectrometry-mass spectrometry studies," European Journal of Mass Spectrometry, 15(2): 113-130 (Jan. 2009).

(56) References Cited

OTHER PUBLICATIONS

Sobott et al., "A Tandem Mass Spectrometer for Improved Transmission and Analysis of Large Macromolecular Assemblies," Anal. Chem., 74(6):1402-1407 (Apr. 2002).
Tolmachev et al., "Characterization of Ion Dynamics in Structures for Lossless Ion Manipulations," Anal. Chem., 86(18):9162-9168 (Sep. 16, 2014).
Tridas, Eric Miguel et al., "High transmission 3D printed ftex-PCB-based ion funnel", Journal of Mass Spectrometry 2015, pp. 938-943, 50, John Wiley & Sons.
Webb et al., "Experimental Evaluation and Optimization of Structures for Lossless Ion Manipulations for Ion Mobility Spectrometry with Time-of-Flight Mass Spectometry," Anal. Chem., 86(18):9169-9176 (Sep. 5, 2014).
Webb et al., "Mobility-Resolved Ion Selection in Uniform Drift Field Ion Mobility Spectrometry/Mass Spectrometry: Dynamic Switching in Structures for Lossless Ion Manipulations," Anal. Chem., 86(19):9632-9637 (Oct. 7, 2014).
Yoshimura, Kentaro, et al. "Development of non-proximate probe electrospray ionization for real-time analysis of living animal" Mass Spectrometry 3. Special_Issue_3 (2015) S0048-S0048.
Zhang, Wenpeng, et al. "Ambient ionization and miniature mass spectrometry systems for disease diagnosis and therapeutic monitoring" Theranostics 7.12 (2017) 2968.
Zhang et al., "Ion Trapping, Storage, and Ejection in Structures for Lossless Ion Manipulations," Anal. Chem., 87(12):6010-6016 (May 2015).
Zhong et al., "Characterizing the resolution and accuracy of a second-generation traveling-wave ion mobility separator for biomolecular ions," The Royal Society of Chemistry, 136(17):3534-3541 (Mar. 2011).
Office Action for U.S. Appl. No. 17/570,279, mailed on Oct. 14, 2022, Taghioskoui, "Ion Analysis System and Method With Multiple Ionization Sources and Analyzers", 5 pages.
Office Action for U.S. Appl. No. 18/224,460, mailed on Mar. 14, 2024, Taghioskoui, "Apparatus, system, and method for transporting biological samples between two analytical systems", 6 pages.

* cited by examiner

FIG.9R  FIG.9S

APPARATUS, SYSTEM, AND METHOD FOR TRANSFERRING IONS

RELATED APPLICATIONS

The present application is a continuation of and claims priority benefit of the application Ser. No. 16/509,016 filed on Jul. 11, 2019, which is a continuation-in-part (CIP) of application Ser. No. 16/350,396, filed on Jul. 12, 2018, which claims priority to Provisional Application No. 62/680,592 filed on Jun. 5, 2018; and application Ser. No. 16/509,016 further claims priority to Provisional Application No. 62/838,076 filed on Apr. 24, 2019, and Provisional Application No. 62/855,089 filed on May 31, 2019, and the content and disclosure of which are hereby incorporated by reference in their entireties herein.

TECHNICAL FIELD

The present disclosure relates to ion source probes, ion transfer devices, and methods or algorithms to produce and transfer ions using the ion source probes and ion transfer devices, which collectively may be referred to as reconfigurable sequentially-packed ion (SPION) transfer device or reconfigurable SPION transfer system or platform in the present disclosure. In particular, the present disclosure is related to one or more ionization probes that produce ions from one or more samples and one or more ion transfer devices that are flexible or re-configurable and may be bent or re-configured from one shape to another shape while transferring ions produced from a sample in a first location, the ions being produced using the one or more ionization sources, including ionization probes, to one or more ion analyzers (such as one or more mass spectrometers and/or one or more ion mobility analyzers, which analyze ions based on mass to charge ratio or ion mobility, respectively) in the second location. The ions may be transferred via the ion transfer device in sequentially-packed ion packets.

BACKGROUND

Mass spectrometry and ion mobility spectrometry are analytical techniques for chemical analysis to detect and identify analytes of interest in various applications. With the increased use of these instruments, their applications and the variety of applications have increased. However, their size still remains large, hindering their applications in point of care/action/need applications, where size and portability is limiting. In addition, they are originally designed for bedside clinical applications.

A mass spectrometer is a complex system composed of various components, as shown in FIG. 1. The critical components of a typical mass spectrometer consist of sample introduction and ionization 1, sampling inlet 2, ion optics and mass analyzer 4, detector 5, vacuum chamber or housing 3, vacuum system 9 including vacuum pumps and gauges, voltage supply systems 6, control systems 7, and data acquisition systems 8. In a typical mass spectrometer, first, the ionization source 1 ionizes a sample to produce positive and negative ions. The produced ions travel through the sampling inlet 2 and are guided, for example, by ion guides, such as an ion funnel and/or multipole ion guides, to enter the mass analyzer 4. All of these components are closely and rigidly connected to each other. The mass analyzer 4, which is derived by voltage supply systems 6, separates ions based on their m/z. The detector 5 produces an electrical signal when the ions hit the detector 5. The data acquisition systems 8 receive the electrical signal from the detector 5, typically in the form of electrical current or voltage, and produce and record spectra. The spectra provide fingerprints for chemical identification of the sample. Control systems 7 control various components. All components related to the mass analysis and ion detection are placed inside a vacuum chamber 3, maintained at high vacuum. Although FIG. 1A shows sample introduction/ionization block 1 outside the vacuum region, ionization of samples may occur in a wide range of pressures, from atmospheric pressure to high vacuum. In a conventional mass spectrometer, the sample introduction/ionization 1 is attached to the sampling inlet 2.

Mass spectrometers require high vacuum for proper mass analysis because, ideally, ions must travel inside a mass spectrometer without colliding with background gas molecules. Therefore, the vacuum in the mass analyzer 4 of a mass spectrometer must be maintained at a pressure that correlates with ion mean free path length longer (ideally several folds) than the length of the mass analyzer. According to the kinetic theory of gases, the mean free path L (in m) is given by: $L = KT/\sqrt{2}\, p\sigma$, where k is the Boltzmann constant, T is the temperature (K), p is the pressure (Pa), and $\sigma$ is the collision cross-section ($m^2$). In a typical mass spectrometer with $k=1.38\times10^{-21}$ $JK^{-1}$, T=300 K, and $\sigma=45\times10^{-20}$ $m^2$, the mean free path equation simplifies to L=4.95/p, where L is in centimeters and p is in milli-Torr In laboratory-scale mass spectrometers, ion filtering and detection usually occur in high vacuum, i.e. $<10^{-5}$ Torr, corresponding to a mean free path of >4.95 meters. This is necessary to achieve high resolution separation of ions. To achieve a pressure of $<10^{-5}$ Torr with available vacuum technologies, a two-stage vacuum generation process is utilized. First, pressure is reduced to $\sim 10^{-2}$ Torr using mechanical or roughing pumps, and then one or more turbo-molecular pumps, ion pumps, or cryogenic pumps further reduce the pressure to $<10^{-5}$ Torr. Turbo-molecular pumps provide relatively higher pumping capacities compared to ion pumps and are more appropriate for atmospheric pressure sampling and ionization. Ion pumps have advantages when vibration-free operation and ultra-high vacuum is required (vacuum levels of $<10^{-10}$ Torr).

Prior to the introduction of soft ionization and ambient ionization techniques, mass spectrometry was generally limited to the analysis of volatile, relatively low-molecular-mass samples, and mass spectrometric analysis of biomolecules was difficult if not impossible. Also, conventional ionization sources, such as electron impact ionization, caused excessive fragmentation when applied to biomolecules. The advent of soft ionization techniques, which produce molecular ions with little or no fragmentation in ambient or near-ambient environment, made it possible to analyze large organic molecules and biomolecules with mass spectrometers. In particular, the development of electrospray ionization (ESI) and matrix-assisted laser desorption/ionization (MALDI) has extended the application of mass spectrometry to biomolecules. These techniques have demonstrated unparalleled advantages, for example in analyzing peptides and proteins, because of the speed of experiments, the amount of information generated, and the outstanding resolution and sensitivities offered.

Among various soft ionization techniques, ESI sources are best suited for direct analysis of biomolecules. ESI may function as a liquid sample introduction system and an ionization source at the same time. In ESI, the sample in a solution (typically a 50/50 mixture of water/methanol with 0.1-1% acetic or formic acid) enters a narrow capillary and leaves the capillary as a liquid spray. The voltage at the end of the capillary is significantly higher (3 to 5 kV) than that of the mass analyzer, so the sample is sprayed or dispersed into an aerosol of highly charged droplets. Evaporation of solvent decreases the size of the droplets. Because the electrically charged droplets retain their charge but get smaller, their electric field increases. At some point, mutual repulsion between like charges causes ions to leave the surface of the droplet. As a result, multiply charged ions from individual biomolecules, free from solvent, are released and enter the sampling inlet for analysis by a mass spectrometer.

Except for MALDI and similar ionization methods that ionize samples in the high-vacuum region, most mass spectrometry techniques for analyzing biomolecules rely on interfaces or sampling inlets that deliver gas-phase molecular ions from atmospheric pressure or near atmospheric pressure to high vacuum through orifices or capillaries. Achieving high ion transfer efficiencies for mass spectrometers is crucial and challenging. Conductance limiting orifice plates enable differential pumping of various stages of a mass spectrometer. Smaller orifices enable operation with lower pumping capacities but result in lower ion transfer efficiencies. Larger-diameter orifices may improve efficiency of ion transfer but allow more neutrals to enter the vacuum region, thus requiring larger, higher-speed pumps to maintain the desired vacuum. Therefore, the pumping capacity of the vacuum system indirectly determines the ion transfer efficiency because the size and dimensions of the sampling inlet must be designed according to the pumping capacity of the vacuum system. Finding the right balance between the pumping capacity and the ion transfer efficiency is a challenge for mass spectrometers if a limited pumping capacity is available.

Various sampling mechanisms are developed to address the above-noted challenges, such as the discontinuous atmospheric pressure interface (DAPI) and the pulsed pinhole atmospheric pressure interface (PP-API). The continuous atmospheric pressure interface enabled by differential pumping is another sampling mechanism that uses multistage vacuum pumps for differential pumping, to provide gradual pressure reduction to transport ions from atmospheric pressure to high vacuum. The extent to which the motion of ions may be controlled in different vacuum stages determines the overall ion transmission efficiency of a mass spectrometer. Recently, ion funnels in combination with heated-capillary inlet have attracted significant interest in atmospheric pressure sampling in addition to the conventional multipole ion guides. Ion funnels enable manipulation and focusing of ions in a pressure regime (0.01 to 30 Torr), providing much greater ion transmission efficiencies. In mass spectrometers employing ion funnel technology, ion funnels are located right after heated capillary inlets inside a mass spectrometer. Ion funnels are rigid structures that guides ions in mid-vacuum level of 0.01 to 30 Torr. In ion funnels, the spacing between ring electrodes are constant.

Mass analyzers are the core components of mass spectrometers and are typically characterized by their mass range and resolution. Mass range is the maximum resolvable m/z by the analyzer. Resolution is an indicator of how selective a mass filter is in distinguishing ions with m/z that are close in value. Thus far, various mass analyzers with different mechanisms have been developed. Mass analyzers may be categorized into beam analyzers, such as quadrupole and TOF analyzers, and trapping analyzers, such as ion traps. Other types of mass analyzer include quadrupole mass analyzer, time of flight mass analyzer, magnetic sector mass analyzer, electrostatic sector mass analyzer, quadrupole ion trap mass analyzers, Orbitrap®, or ion cyclotron resonance.

Faraday cups and micro channel plate (MCP) detectors are the two most widely used ion detectors in mass spectrometry. Faraday cups may operate at high pressures (up to atmospheric pressure), but are less sensitive, and are not compatible with high-resolution mass spectrometry due to slow response times. MCPs support high mass resolution, dynamic range, and detection sensitivity. Most modern MCP detectors consist of two MCPs, with angled channels rotated 180° from each other, producing a chevron (v-like) shape. The angle between the channels reduces ion feedback. In a chevron MCP, the electrons that exit the first plate initiate the cascade in the next plate. The advantage of the chevron MCP over the straight channel MCP is significantly more gain at a given voltage. The two MCPs may either be pressed together or have a small gap between them to spread the charge across multiple channels.

With the advent of ambient desorption ionization sources, which desorb and ionize molecules in their native state, the applications of mass spectrometers have been extended significantly. For example, ambient desorption ionization techniques may be used to analyze human tissues during a surgery to differentiate cancer cells. As another example, ambient ionization desorption techniques may be used in homeland security to monitor cargo and passengers at security check points for explosives. Three different scenarios have been used thus far for such applications. In the conventional method shown in FIG. 1B, the samples are brought close to a mass spectrometer for ionization and analyses. In this approach, samples are directly place in front of a mass spectrometer. In a second approach shown in FIG. 1C, samples or sample molecules are transferred through a bare tube 19, which may be plastic or metal, into an ionization source 11 of the mass spectrometer. A sampling medium, such as water, may be used to mix sample with sampling medium to be transferred through the bare tube to a mass spectrometer. In other methods that use second approach, vapor, ions and/or plume from a remote sample flows through the tube to reach the mass spectrometer. In the third approach shown in FIG. 1D, samples are ionized using an ion source that is detached from a mass spectrometer and the produced ions are transferred via the bare tube 19 to a mass spectrometer for analysis. All of these approaches have disadvantages. Loss of sensitivity due to inefficient sample/ion transfer, and cross-contamination are the main drawbacks. Further, placing a sample directly in front of a mass spectrometer (FIG. 1B) may not be practical in many applications, particularly when the sample is bulky or immobile, or for clinical application at the surgery room. Second transferring sample molecules via the bare tube 19 to a mass spectrometer (FIG. 2B) may result in memory effects from sample residue/molecules sticking to the inner surface of the bare tube 19. These residues may contaminate the inner side of the bare tube 19 and may adversely affect the analytical results. Transferring ions through bare tube 19, as shown in FIG. 1D, may result in decreased ion transfer efficiency because most ions are lost to the inner walls of the bare tube 19 and deteriorate ion transfer efficiency. In other words, the ion transfer efficiency may not be sufficient, and a majority of ions may be lost in the ion transfer process, thus negatively affecting analytical performance.

SUMMARY

One or more embodiments of the present disclosure relates to a flexible ion transfer device that may transfer ions from a first location to a second location, such that the first location may be in a proximity of where samples to be analyzed are located and the second location is where a mass spectrometer is located. Mass spectrometers are still bulky but the growing demand of mass spectrometers in point of need/care/action, such as clinical, medical and security applications require having mass spectrometers more accessible. Conventional mass spectrometers are not really designed for such application because, for example, mass spectrometers are bulky and large. Further, ambient ionization techniques produce ions from samples in their native environment (such as human tissues during surgery to detect cancer cells). Therefore, the present disclosure aims to provide an improvement over the state-of-the-art by providing a flexible ion transfer device that may be connected between an ambient ionization source (which may be constructed as an application-specific or general-purpose ionization probe) in a first location and a mass spectrometer in a second location such that the ions produced by the ionization source may be efficiently transferred to a mass spectrometer via the flexible ion transfer device. The flexible ion transfer device provides an advantage that an operator/user may easily move the ionization source to/around the sample and may produce ions for mass spectrometry analysis without having to bring a mass spectrometer closer to a sample under test. Further, various ionization sources or ionization source probes may be attached to a single mass spectrometer, which results in more efficient use of a mass spectrometer. It is noted that the sample analysis in a mass spectrometer from the moment ions are produced to the moment the ions are detected by the detector takes milliseconds to a few seconds. Therefore, mass spectrometers are ideally able to provide continuous analysis every few seconds at most. However, the sample introduction techniques are currently a limiting factor of the process. The time in between two mass spectrometric analyses currently lag behind a mass spectrometers ideal throughput because of the slow sample introduction. Therefore, producing a sequence of ion packets from different samples to be analyzed by a mass spectrometer will significantly improve throughput of mass spectrometry analysis. For example, sequentially packed ions may be produced from various ionization sources and may be queued and transferred to a mass spectrometer for analysis, thus increasing throughput of analyses. The present disclosure provides an ion transfer device and an ion transfer method for producing ions in a remote location and for transferring the produced ions sequentially to a mass spectrometer for analysis.

In one or more embodiments, an ion transfer device that transfers ions from at least one ion inlet to at least one ion outlet of the ion transfer device, the ion transfer device includes an enclosure configured to maintain reduced pressure; and a plurality of electrodes disposed at least in part inside the enclosure such that one or more electrodes of the plurality of electrodes are configured to be flexible, re-configurable, or flexibly connected to each other.

In one or more embodiments, ion transfer device is configured to be flexible or re-configurable and is configured or be bent from two or more bend positions to form a plurality of one or more curvatures, for example, while actively and efficiently transferring the ions. In one or more embodiments, the one or more electrodes of the plurality of electrodes are flexibly connected to each other to make the ion transfer device re-configurable while actively transferring the ions from a first location to a second location. In one or more embodiments, the enclosure and the at least two electrodes are flexibly attached or connected to each other to allow the ion transfer device to transfer the ions in two or more different shapes or configurations.

In one or more embodiments, the the plurality of electrodes are configured to be transformable between two or more different physical shapes, and the plurality of electrodes are configured to transfer the ions in the two or more different physical shapes from the at least one ion inlet to the at least one ion outlet. In one or more embodiments, the reduced pressure is between 0.0001 Torr to 750 Torr. In one or more embodiments, the ion transfer device is re-configurable or transformable between at least a first configuration and a second configuration, the ion transfer device, in the first configuration, transfers ions from a first location to a second location, and the ion transfer device, in the second configuration, transfers the ions from the first location to a third location, the third location being different from the second location.

In one or more embodiments, at least two of the plurality of electrodes are configured to be flexibly attached to each other, for example, using electrically insulating material In one or more embodiments, a first group of electrodes comprising a first number of the plurality of electrodes are attached to each other in a non-flexible manner, a second group of electrodes including a second number of the plurality of electrodes are attached to each other in a non-flexible manner, and the first group of electrodes and the second group of electrodes are attached to each other in a flexible manner to allow bending of the first group of electrodes or the second group of electrodes around one or more axes with respect to each other.

In one or more embodiments, the plurality of electrodes are ring-shaped electrodes that are stacked, and for example, form an elongated ion funnel structure. In one or more embodiments, the plurality of electrodes are wires in helical form. In one or more embodiments, the plurality of electrodes are disposed parallel to each other and are elongated along an axis of the ion transfer device. In one or more embodiments, the plurality of electrodes are attached to an inner surface of the enclosure. In one or more embodiments, RF voltage and DC voltage are applied to the plurality of electrodes, for example, the RF voltage and DC voltage being applied to each of the plurality of electrodes respectively via a capacitor and a resistor. In one or more embodiments, the DC voltage is traveling DC voltage pulse. In one or more embodiments, RF voltage applied to each of the plurality of electrodes is out of phase with the RF voltage applied to adjacent electrodes.

In one or more embodiments, the DC voltage causes the ions to move axially parallel to an axis of the ion transfer device, and the RF voltage causes the ions to move radially around the axis of the ion transfer device. In one or more embodiments, the ion transfer device is connected to an ion source that is configured to be freely movable in 3-dimentional space, for example, to bring it in close to a sample under test to produce the ions from the sample under test. In one or more embodiments, An ion analysis system includes at least one ion source configured to produce ions from a sample; at least one ion transfer device having an enclosure, and a plurality of electrodes disposed at least in part inside the enclosure, one or more electrodes of the plurality of electrodes are configured to be flexible, re-configurable, or flexibly connected to each other; at least one analyzer configured to separate the ions based on mobility or mass to charge ratio; and at least one detector configured to detect the separated ions. In one or more embodiments, A method includes transferring ions with at least one ion transfer device having an enclosure configured to maintain reduced pressure, and a plurality of electrodes disposed at least in part inside the enclosure such that the one or more electrodes of the plurality of electrodes are configured to be flexible, re-configurable, or flexibly connected to each other.

In one or more embodiments, ion transfer device further includes RF voltage sources configured to supply RF voltages; DC voltage sources configured to supply constant DC voltages, time-variable DC voltages, or both; and a controller configured to control the RF voltage sources and DC voltage sources.

In one or more embodiments, ion transfer device further includes a first adapter configured to connect to an ion source; and a second adapter configured to connect to an ion guide of a mass spectrometer or an ion mobility analyzer. In one or more embodiments, one or more of the plurality of electrodes are flexibly connected to each other via the enclosure, a plurality of connectors, a plurality of wires, or a combination thereof. In one or more embodiments, the ions move from the at least one ion inlet to the at least one ion outlet of the ion transfer device in separate ion packets in sequential manner. In one or more embodiments, the separate ion packets are produced by a plurality of ion sources operated in a multiplexed manner and each ion source has an allocated time frame to introduce one or more ion packets into a mass spectrometer or ion mobility analyzer.

In one or more embodiments, each of the separate ion packets are produced by one or more different ion sources, or by one or more of the same ion sources. In one or more embodiments, each of the separate ion packets are produced from same location on a sample, from different locations on a sample, from different samples, or a combination thereof. In one or more embodiments, a plurality of electrode units trap or contain the ions in ion packets, each electrode unit being a group of electrodes from the plurality of electrodes.

In one or more embodiments, DC voltages applied to the electrodes of each electrode unit are periodically increased or decreased from one voltage value to another voltage value to allow each of the ion packets move into an adjacent electrode unit. In one or more embodiments, the ion packets are shifted sequentially in the electrode units to move from the at least one inlet to the at least one outlet of the ion transfer device. In one or more embodiments, the ions are trapped or contained in the ion packets in each of the plurality of electrode units by RF voltages and DC voltages, the DC voltages creating potential barrier between two adjacent electrode units. In one or more embodiments, the DC voltages of each electrode of the electrode unit are individually controlled, or the DC voltages of electrodes of the electrode unit are controlled by a single DC voltage.

In one or more embodiments, the enclosure is one or more tubes, one or more heat-shrink tubes, one or more bellow tubes, or a combination of one or more tubes, one or more heat-shrink tubes, and one or more bellow tubes. In one or more embodiments, the one or more tubes, one or more heat-shrink tubes, and one or more bellow tubes are made of plastic, metal, or a combination of plastic and metal. In one or more embodiments, heat-shrink tube shrinks upon application of heat and flexibly holds the plurality of electrodes. In one or more embodiments, a plurality of wires are disposed outside or inside the enclosure.

In one or more embodiments, all the plurality of electrodes are flexible or re-configurable. In one or more embodiments, the plurality of electrodes are printed circuit board (PCB) electrodes and are made of PCB. In one or more embodiments, a resistor and a capacitor are assembled on the PCB electrode. In one or more embodiments, capacitors and resistors are assembled on separate flexible or rigid PCB connected to the PCB electrodes. In one or more embodiments, a plurality of connectors of each PCB electrode connect the PCB electrode to adjacent PCB electrodes. In one or more embodiments, the plurality of connectors connect the PCB electrode to DC power supplies and RF power supplies. In one or more embodiments, electrical connections from one board to the next board are made with connectors, soldering, or spot-welding. In one or more embodiments, diameters of the plurality of electrodes vary along a length of the ion transfer device.

In one or more embodiments, the plurality of electrodes are connected by matching extrusions on two sides of the electrodes that engage with corresponding matching extrusions of adjacent electrodes. In one or more embodiments, a plurality of spacers are placed in between the plurality of electrodes. In one or more embodiments, length of the ion transfer device is greater than 10 cm, 50 cm, 100 cm, 150 cm, or 200 cm, 2 meters, 5 meters, or 10 meters. In one or more embodiments, the ions are transferred efficiently from the at least one ion inlet to the at least one ion outlet of the ion transfer device. In one or more embodiments, the ion transfer device holds or retains a new shape or form after changing the shape or form from an old shape to a new shape. In one or more embodiments, the ion transfer device does not hold or retain a new shape or form after changing the shape or form from an old shape to a new shape. In one or more embodiments, degree of bending with respect to an axis of each electrode to an axis of an adjacent electrode is between 0.0001 to 5 degrees. In one or more embodiments, the ion transfer device actively transfers the ions from a first location to a second location. In one or more embodiments, each of the plurality of electrodes are flexibly connected to each other. In one or more embodiments, the plurality of electrodes have a central hole. In one or more embodiments, the RF voltage and DC voltage are applied to the plurality of electrodes respectively via capacitors and a resistors. In one or more embodiments, two or more ionization sources are connected, via one or more of the ion transfer devices, to an ion guide of a mass spectrometer or ion mobility analyzer. In one or more embodiments, the ion analysis system is used to analyze traces of explosives, peptide, proteins, biological samples, human or animal tissue, or quality in manufacturing line.

In one or more embodiments, one or more ion sources are connected to an ion processor. In one or more embodiments, the ion analysis system provides real-time analysis.

In one or more embodiments, method further includes producing ions in at least one ion source; transferring the ions with the at least one ion transfer device; separating the ions with at least one analyzer configured to separate the ions based on mobility or mass to charge ratio; and detecting the separated ions with at least one detector.

In one or more embodiments, a probe includes at least one ion source configured to produce ions from a sample such that the probe is connected to an analyzer via at least one ion transfer device, the ion transfer device comprising: an enclosure configured to maintain reduced pressure; and a plurality of electrodes disposed at least in part inside the enclosure such that the one or more electrodes of the plurality of electrodes are configured to be flexible, re-configurable, or flexibly connected to each other. In one or more embodiments, the probe is moved by an operator, a user, or a robotic arm of a robot.

In one or more embodiments a method for analyzing a sample using mass spectrometry or ion mobility spectrometry includes producing gas-phase ions and neutrals from the sample in a proximity of the sample; transferring the produced ions from the sample to a distance via a flexible or re-configurable ion transfer device, the flexible or re-configurable ion transfer device employing RF voltages to transfer the ions; separating the produced ions with a mass spectrometer or a mobility analyzer located at the distance to provide spectrometric results; and detecting the separated ions with at least one detector.

In one or more embodiments, the sample is a biological sample of a human subject or a non-human animal subject, or a specimen derived from said human or non-human animal subject. In one or more embodiments, the biological sample is in vivo tissue.

In one or more embodiments, the method further includes determining presence, type, grade, stage, or a combination thereof of a disease in one of more regions of the sample that is a biological sample based on the spectrometric results.

In one or more embodiments, determining is performed based on determining one or more biomarkers for the disease in the biological sample. In one or more embodiments, the disease is one or more cancers, cancer tumors, or tumor margins.

In one or more embodiments, the method further includes separating the produced ions based on ion mobility in the flexible or re-configurable ion transfer device while transferring the produced ions along the ion transfer device. In one or more embodiments, the proximity is between 0.1 mm to 50 mm.

In one or more embodiments, the method further includes before transferring, ionizing the gas-phase neutrals in the proximity of the sample with one or more ionization sources.

In one or more embodiments, from the produced gas-phase ions and neutrals from the sample, only the produced ions from the sample is transferred by the ion transfer device.

In one or more embodiments, the produced neutrals from the sample that are not ionized by the one or more ionization sources in the proximity of the sample, are not transferred in the transferring and are not separated in the separating.

In one or more embodiments, neutrals include one or more of aerosols, vapor, particles, or clusters from the sample.

In one or more embodiments, the producing includes performing ablation or desorption of the sample to produce a plume including the gas-phase ions and neutrals; and ionizing the plume in the proximity of the sample with one or more ionization sources.

In one or more embodiments, the performing ablation or desorption and the ionizing the plume are performed by irradiating laser pulses and electrospray ionization respectively.

In one or more embodiments, the performing ablation or desorption and the ionizing the plume are performed by irradiating IR and UV laser pulses respectively.

In one or more embodiments, the ionizing the plume is performed between 1 nanosecond to 5 seconds after the performing ablation or desorption.

In one or more embodiments, the ionizing the plume is performed at ambient pressure or reduced pressure by one or more ambient pressure or reduced pressure ionization sources.

In one or more embodiments, the one or more ambient pressure or reduced pressure ionization sources are UV lamp, UV laser, electrospray, gas discharge, or plasma, or combination of UV lamp, UV laser, electrospray, gas discharge, and plasma.

In one or more embodiments, length of the ion guide is greater than 10 cm, 50 cm, 100 cm, 150 cm, or 200 cm, 2 meters, 5 meters, or 10 meters.

In one or more embodiments, the producing ions from the sample in the proximity of the sample is performed by a hand-held probe.

In one or more embodiments, the producing is performed by steering one or more laser beams on a surface of the sample to produce a chemical or biological spectrometric image of the surface with the spectrometric results.

In one or more embodiments, the producing ions from the biological sample in the proximity of the biological sample is performed by an endoscopic probe.

In one or more embodiments, the producing is performed at one end of the endoscopic probe that inserted inside body and is in the proximity of the biological sample.

In one or more embodiments, an endoscopic ion source used with a mass spectrometer or an ion mobility analyzer for in vivo tissue analysis includes a multi-lumen tubing having a tip and a plurality of channels, the multi-lumen tubing configured to be inserted into human or animal body for the tip to reach a proximity of tissue; one or more optical fibers positioned inside the plurality of channels, the one or more optical fibers configured to guide one or more laser beams from one or more laser sources to the tissue, the laser beams configured to produce gas-phase ions and neutrals by ablation, desorption, ionization, or a combination thereof from the tissue; a first set of tubes positioned inside the plurality of channels configured to provide gas flow at the tip; and a second set of tubes positioned inside the plurality of channels configured to suck in the produced gas-phase ions and neutrals from the tip of one of the second set of tubes, the one of the second set of tubes being connected to a voltage or ground.

In one or more embodiments, the first set of tubes and the second set of tubes are concentric.

In one or more embodiments, the first set of tubes and the second set of tubes are made of non-conductive materials or conductive materials, or a combination thereof.

In one or more embodiments, the first set of tubes and the second set of tubes are concentric and provide a sampling inlet with curtain gas.

In one or more embodiments, a first laser beam of the laser beams produces a plume including gas-phase ions and neutrals, and the second laser beam of the laser beams ionizes the plume in the proximity of the tissue.

In one or more embodiments, the first laser beam and the second laser beam are respectively IR and UV laser pulses.

In one or more embodiments, the endoscopic ion source further includes one or more second ion sources configured to ionize a plume produced by one or more laser beams in the proximity of the tissue.

In one or more embodiments, the one or more second ion sources ionize the plume by one or more ambient pressure or reduced pressure ionization sources.

In one or more embodiments, the one or more second ion source ionizes the plume between 1 nanosecond to 5 seconds after the plume is produced.

In one or more embodiments, the one or more ambient pressure or reduced pressure ionization sources are UV lamp, UV light emitting diode, UV laser, electrospray, gas discharge, or plasma, or a combination of UV lamp, UV light emitting diode, UV laser, electrospray, gas discharge, and plasma.

In one or more embodiments, the proximity is between 0.1 mm to 50 mm. In one or more embodiments, a diameter of the multi-lumen tubing is less than 10 mm or less than 5 mm. In one or more embodiments, the first set of tubes, the second set of tubes, and the one or more optical fibers are bundled together and fixed in the multi-lumen tubing in a non-removable manner.

In one or more embodiments, the first set of tubes, the second set of tubes, and the one or more optical fibers are positioned in the multi-lumen tubing in a removable manner.

In one or more embodiments, a plurality of wheels control a position of the tip for navigation inside the body.

In one or more embodiments, the produced ions and neutrals are sucked into at least one of the second set of tubes from one end at the tip and from other end enter a flexible or re-configurable ion transfer device to be transferred to a mass spectrometer or ion mobility analyzer, the flexible or re-configurable ion transfer device employing RF voltages to efficiently transfer the produced ions.

In one or more embodiments, the ion source is connected to a flexible or re-configurable ion transfer device employing RF voltages to transfer the produced ions.

In one or more embodiments, from the produced gas-phase ions and neutrals from the tissue, only the produced ions from the tissue are transferred by the ion transfer device.

In one or more embodiments, the produced neutrals are not transferred by the ion transfer device if the produced neutrals are not ionized by the one or more ionization sources in the proximity of the tissue.

In one or more embodiments, the produced neutrals include one or more of aerosols, vapor, particles, or clusters from the tissue.

In one or more embodiments, the produced ions are analyzed with the mass spectrometer or the ion mobility analyzer located at the distance to produce spectrometric results.

In one or more embodiments, presence, type, grade, stage, or combination thereof of a disease in one of more regions of the tissue is determined based on the spectrometric results.

In one or more embodiments, the presence, type, grade, stage, or combination thereof of the disease is determined by determining one or more biomarkers for the disease in the tissue. In one or more embodiments, the ion transfer device is configured to be bent from one or more bend positions to form a plurality of curvatures.

In one or more embodiments, the ion transfer device is configured to be bent from one or more bend positions to form a plurality of curvatures while actively and efficiently transferring the ions.

In one or more embodiments, the ion transfer device comprises a plurality of electrodes configured to be flexibly connected to each other to make the ion transfer device re-configurable while actively transferring the ions to the mass spectrometer or the ion mobility analyzer.

In one or more embodiments, the ion transfer device is configured to be transformable between two or more different physical shapes, and the ion transfer device is configured to transfer the ions in the two or more different physical shapes from the ion source to the mass spectrometer or the ion mobility analyzer.

In one or more embodiments, the ion transfer device is maintained at a pressure between 0.0001 to 750 Torr.

In one or more embodiments, the ion transfer device is re-configurable or transformable between at least a first configuration and a second configuration. In one or more embodiments, the endoscopic ion source is flexible. In one or more embodiments, the tip includes a protective cover. In one or more embodiments, pressure at one end of the second set of tubes that is in the proximity of the sample is atmospheric pressure of 760 Torr, and pressure at the other end of the second set of tubes is reduced pressure in range of 0.001 to 750 Torr. In one or more embodiments, at least one of the first set of tubes, the second set of tubes, and one or more optical fibers extend from the tip of the multi-lumen tubing.

In one or more embodiments, an ion source probe that produces ions from a sample for analysis by a mass spectrometer or ion mobility analyzer includes a housing; one or more ion sources located inside the housing and configured to produce gas-phase ions and neutrals from the sample by ablation, desorption, ionization, or combination thereof in a proximity of the sample; and an ion extractor located inside the housing and configured to extract and transfer the produced gas-phase ions and neutrals to a flexible or re-configurable ion transfer device connected to the probe, the flexible or re-configurable ion transfer device employing RF voltages to transfer the produced ions.

In one or more embodiments, the ion extractor includes a first set of tubes configured to suck in the produced gas-phase ions and neutrals from an inlet of one of the plurality of tubes.

In one or more embodiments, the ion extractor further includes a second set of tubes configured to provide gas flow.

In one or more embodiments, the first set of tubes and the second set of tubes are concentric.

In one or more embodiments, the first set of tubes and the second set of tubes are made of non-conductive materials or conductive materials, or a combination thereof, the conductive materials being connected to a voltage or ground.

In one or more embodiments, the first set of tubes and the second set of tube are concentric and provide a sampling inlet with curtain gas.

In one or more embodiments, the ion extractor includes a stacked ring ion guide, or an ion funnel.

In one or more embodiments, at least one of the one or more ion sources is a first laser beam that produces a plume including gas-phase ions and neutrals.

In one or more embodiments, at least another of the one or more ion sources is a second laser beam that ionizes the plume in the proximity of the sample.

In one or more embodiments, the ablation or desorption to create the plume and the ionization of the plume are respectively performed by irradiating IR and UV Jaser.

In one or more embodiments, ion source probe further includes one or more second ion sources configured to ionize the plume in the proximity of the sample.

In one or more embodiments, the one or more second ion sources ionizes the plume by one or more ambient pressure or reduced pressure ionization sources.

In one or more embodiments, the one or more second ion source ionizes the plume between 1 nanosecond to 5 seconds after the plume is produced.

In one or more embodiments, the one or more ambient pressure or reduced pressure ionization sources are UV lamp, UV laser, electrospray, gas discharge, or plasma, or a combination of UV lamp, UV laser, electrospray, gas discharge, or plasma.

In one or more embodiments, a laser beam steering device steers laser beam on a surface of the sample to produce chemical composition imaging of the surface.

In one or more embodiments, the proximity is between 0.1 mm to 50 mm.

In one or more embodiments, the produced ions and neutrals are extracted and transferred by the ion extractor to a flexible or re-configurable ion transfer device to be transferred to a mass spectrometer or ion mobility analyzer, the flexible or re-configurable ion transfer device employing RF voltages to efficiently transfer the produced ions.

In one or more embodiments, the ion source probe is connected to a flexible or re-configurable ion transfer device employing RF voltages to transfer the produced ions.

In one or more embodiments, from the produced gas-phase ions and neutrals from the tissue, only the produced ions from the tissue are transferred by the ion transfer device.

In one or more embodiments, the produced neutrals are not transferred if the produced neutrals are not ionized by the one or more ionization sources in the proximity of the sample.

In one or more embodiments, the ions are analyzed with the mass spectrometer or the ion mobility analyzer located at the distance to provide spectrometric results.

In one or more embodiments, the sample is a biological sample of a human subject or a non-human animal subject, or a specimen derived from said human or non-human animal subject. In one or more embodiments, the biological sample is in vivo tissue.

In one or more embodiments, presence, type, grade, stage, or a combination thereof of a disease in one of more regions of the tissue is determined based on the spectrometric results.

In one or more embodiments, the ion transfer device is configured to be bent from one or more bend positions to form a plurality of curvatures.

In one or more embodiments, the ion transfer device is configured to be bent from one or more bend positions to form a plurality of curvatures while actively and efficiently transferring the ions.

In one or more embodiments, the ion transfer device comprises a plurality of electrodes configured to be flexibly connected to each other to make the ion transfer device re-configurable while actively transferring the ions to the mass spectrometer or the ion mobility analyzer.

In one or more embodiments, the ion transfer device is configured to be transformable between two or more different physical shapes, and the ion transfer device is configured to transfer the ions in the two or more different physical shapes from the ion source probe to the mass spectrometer or the ion mobility analyzer.

In one or more embodiments, the ion transfer device is maintained at a pressure between 0.0001 to 750 Torr.

In one or more embodiments, the ion transfer device is re-configurable or transformable between at least a first configuration and a second configuration.

In one or more embodiments, pressure inside the housing is atmospheric pressure of 760 Torr.

In one or more embodiments, pressure inside the housing is reduced pressure in range of 0.0001 to 750 Torr.

In one or more embodiments, the sample is a sample of interest in forensic toxicology, metabolomics, proteomics, pharma or biopharma, and clinical research, drug testing and discovery, food contamination detection, pesticide residue analysis, isotope ratio determination, or protein identification.

BRIEF DESCRIPTION OF DRAWINGS

Certain embodiments of the present disclosure are described with reference to the accompanying drawings. However, the accompanying drawings illustrate only certain aspects or implementations of the present disclosure by way of example and are not meant to limit the scope of the claims.

FIG. 9Q, FIG. 9R, and FIG. 9S show views of an electrode of the flexible or re-configurable ion transfer device connected to each other in accordance with one or more embodiments of the present disclosure.

DETAILED DESCRIPTION

In general, embodiments of the present disclosure relate to a flexible or re-configurable ion transfer device and methods for transferring ions with a flexible or re-configurable ion transfer device. Further, embodiments of the present disclosure relate to ionization probes, ion transfer devices, and methods or algorithms to produce and transfer ions using the ionization probes and ion transfer devices, which may be referred to as reconfigurable sequentially-packed ion (SPION) transfer device or reconfigurable SPION transfer platform or system in the present disclosure.

Specific embodiments are disclosed with reference to the accompanying drawings. In the following description, numerous details are set forth as examples of the present disclosure. It will be understood by those skilled in the art that one or more embodiments of the present disclosure may be practiced without these specific details and that numerous variations or modifications may be possible without departing from the scope of the invention. Certain details known to those of ordinary skill in the art are omitted to avoid obscuring the description.

Figure 1A:
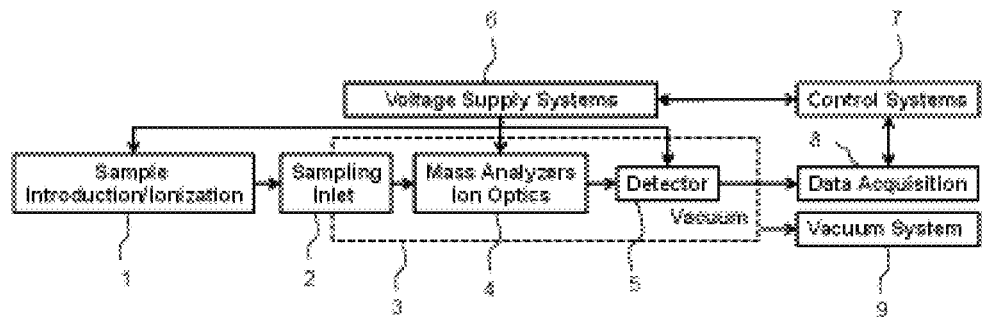
FIG. 1A shows a block diagram of a conventional mass spectrometer.
Figure 1B:
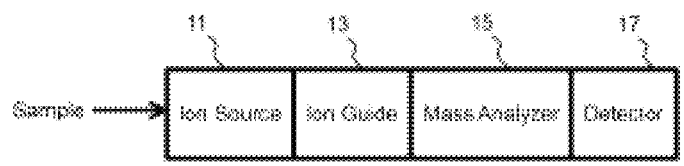
FIG. 1B shows a block diagram of a conventional mass spectrometer.
Figure 1C:
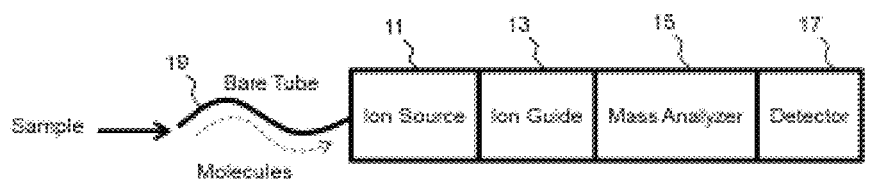
FIG. 1C shows a block diagram of a conventional mass spectrometer such that the ionization source is detached from the ion guide and the ions are transferred to ion guide of a mass spectrometer via a bare tube.
Figure 1D:
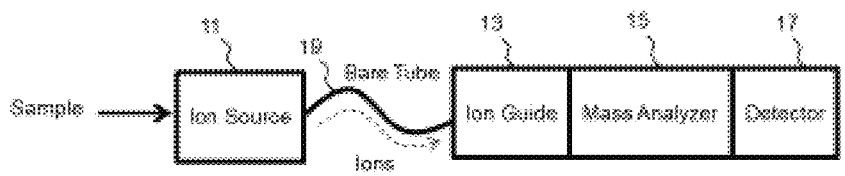
FIG. 1D shows a block diagram of a conventional mass spectrometer such that the sample is located at a distance from the ionization source and the ions are transferred to ionization source of a mass spectrometer via a bare tube.
Figure 2A:
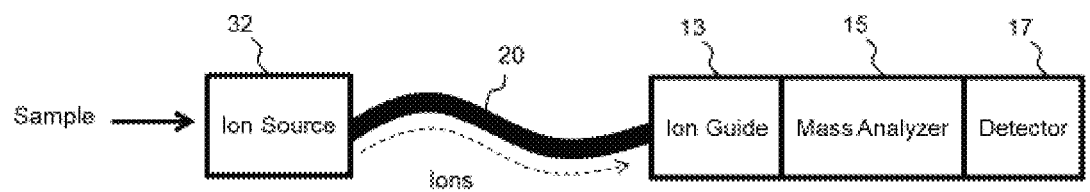
FIG. 2A shows a block diagram of a mass spectrometry system such that the ionization source is detached from the ion guide and the ions are efficiently transferred to ion guide via a flexible or re-configurable ion transfer device in accordance with one or more embodiments of the present disclosure.

FIG. 2A shows a block diagram of a mass spectrometry system such that the ionization source 32 is detached from the ion guide 13 (the ion guide 13 as shown in FIG. 2A, and other figures is a mass spectrometers inlet portion which may include a heated-capillary inlet, an ion funnel, and/or one or more multipole ion guides at an intermediate pressure lower than atmospheric pressure (~760 Torr) and higher than the pressure of mass analyzer portion (usually lower than 10e-5 Torr) of a mass spectrometer produced by differential pumping) and the ions are efficiently transferred to the ion guide 13 via a flexible or re-configurable ion transfer device 20 in accordance with one or more embodiments of the present disclosure. The mass spectrometry system, as disclosed herein, may include the ionization source 32, the ion transfer device 20, the ion guide 13, the mass analyzer 15, the detector 17, and the corresponding vacuum systems and electronics systems (additional sub-systems that is required for operation of a mass spectrometer) for proper operation of the mass spectrometer. Additional sub-systems for a mass spectrometer are shown in FIG. 1A and omitted in this and some other figures of the present application to avoid obscuring the description and drawings and for maintaining simplicity of illustration. One of ordinary skill in the art, in view of the present disclosure, will understand that the mass spectrometry system includes additional sub-systems such as those shown in FIG. 1A for operation.

In FIG. 2A, the mass spectrometry system includes an ionization source 32 that is detached from an ion guide 13 of the mass spectrometry system and the ions are efficiently transferred from the ionization source 32 to the ion guide 13 of the mass spectrometry system through the ion transfer device 20 that is flexible or re-configurable. The ion transfer device in extends out of the mass spectrometers inlet and allows de-coupling of the ion source 32. In one or more embodiments, the flexibility or re-configurability of the ion transfer device 20 may be in form of, or similar to, positioning arms (such as goosenecks, bend-and-stay, Loc-Line®, and Snap-Loc® coolant hoses) that the ion transfer device 20 memorizes and hold a shape after being re-configured. In one or more embodiments, the flexibility or re-configurability of the ion transfer device 20 may be in form of, or similar to, a flexible memory-less hose or tube that do not hold a specific shape after being re-configured or bent. The ion guide 13 may be one or more ion funnels, or one or more multipole ion guides having a plurality of even number of poles used in conventional mass spectrometers. The ionization source 32 may be electrospray, plasma, glow discharge, laser, photoionization, or a combination of them used in ambient ionization techniques. In one or more embodiments, the ionization source 32 may use any ambient ionization techniques under categories "extraction" (a solid or liquid extraction processes dynamically followed by spray or chemical ionization), "plasma" (thermal or chemical desorption with chemical ionization), "two-step" (desorption or ablation followed by ionization), "laser" (laser desorption or ablation followed by ionization), "acoustic" (acoustic desorption followed by ionization), or multimode (involving two of the above modes).

In one or more embodiments, the ionization source 32 (that may be in form of a probe or an endoscopic probe) may be any of Air flow-assisted ionization, Air flow-assisted desorption electrospray ionization, Atmospheric pressure glow discharge desorption ionization, Ambient pressure pyroelectric ionization source, Atmospheric pressure thermal desorption chemical ionization, Atmospheric pressure thermal desorption/ionization, Atmospheric pressure solids analysis probe, Beta electron-assisted direct chemical ionization, Charge assisted laser desorption/ionization, Desorption atmospheric pressure chemical ionization, Desorption atmospheric pressure photoionization, Direct analysis in real time, Dielectric barrier discharge ionization, Desorption corona beam ionization, Desorption chemical ionization, Desorption electro-flow focusing ionization, Desorption electrospray/metastable-induced ionization, Desorption electrospray ionization, Desorption sonic spray ionization, Desorption ionization by charge exchange, Direct inlet probe-atmospheric-pressure chemical ionization, Direct probe electrospray ionization, Electrode-assisted desorption electrospray ionization, Easy ambient sonic-spray ionization, Extractive electrospray ionization, Electrospray laser desorption ionization, Electrospray-assisted pyrolysis ionization, Electrostatic spray ionization, Flowing atmospheric pressure afterglow, Field-induced droplet ionization, High-voltage-assisted laser desorption ionization, Helium atmospheric pressure glow discharge ionization, Infrared laser ablation metastable-induced chemical ionization, Jet desorption electrospray ionization, Laser assisted desorption electrospray ionization, Laser ablation electrospray ionization, Laser ablation flowing atmospheric pressure afterglow, Laser ablation inductively coupled plasma, Laser desorption atmospheric pressure chemical ionization, Laser diode thermal desorption, Laser desorption electrospray ionization, Laser desorption spray post-ionization, Laser electrospray mass spectrometry, Liquid extraction surface analysis, Laser-induced acoustic desorption-electrospray ionization, Liquid micro-junction-surface sampling probe, Leidenfrost phenomenon-assisted thermal desorption, Liquid sampling-atmospheric pressure glow discharge, Laser spray ionization, Low temperature plasma, Matrix-assisted inlet ionization, Matrix-assisted laser desorption electrospray ionization, Microfabricated glow discharge plasma, micro-wave induced plasma desorption ionization, Nano-spray desorption electrospray ionization, Neutral desorption extractive electrospray ionization, Plasma-assisted desorption ionization, Paint spray, Plasma-assisted laser desorption ionization, Plasma-assisted multiwavelength laser desorption ionization, Plasma-based ambient sampling/ionization/transmission, Paper assisted ultrasonic spray ionization, Probe electrospray ionization, Paper spray, Pipette tip column electrospray ionization, Radiofrequency acoustic desorption and ionization, Remote analyte sampling transport and ionization relay, Rapid evaporative ionization mass spectrometry, Robotic plasma probe ionization, Surface activated chemical ionization, Solvent-assisted inlet ionization, Surface acoustic wave nebulization, Secondary electrospray ionization, Solid probe assisted Nano-electrospray ionization, Single-particle aerosol mass spectrometry, Sponge-Spray Ionization, Surface sampling probe, Switched ferroelectric plasma ionizer, Thermal desorption-based ambient mass spectrometry, Transmission mode desorption electrospray ionization, Touch spray, Ultrasonication-assisted spray ionization, Venturi easy ambient sonic-spray ionization, Brush-Spray Ionization, or Fiber-Spray Ionization. The ionization source may be any other ionization source that creates gas-phase ions from a sample and any gas-phase ion irrespective of methods or techniques used for production of the ions may be used with the ion transfer device 20.

In one or more embodiments, re-configurable or flexible in the present disclosure is defined as the capability of being transformed between at least two different shapes, configurations, or forms, or being transformed from one configuration to another configuration. In one or more embodiments, re-configurable or flexible in the present disclosure is defined as the capability to be moved in one, two or three dimensions. In one or more embodiments, this transformation occurs and a shape or a form of the ion transfer device 20 is changed when ions are being actively transferred by the ion transfer device 20. The ion transfer device 20 may have at least one or a plurality of bend positions 12a and 12b, and the ion transfer device may form one or more curvatures (for example, having a bend radius of 0.5" to 3", or 3" to 10" or even up to 20" or more) around the bend positions. In one or more embodiments, the flexible or re-configurable ion transfer device 20 may hold or retain a new shape or form after changing the shape or form from an old shape to a new shape, for example, by simply being hold by a person or robotic arm, a force applied by hands of a person, robotic arm, or an operator. In one or more embodiments, the flexible or re-configurable ion transfer device 20 may be soft and may not retain or hold a new shape or form after changing the shape or form from an old shape to the new shape. In one or more embodiments, flexible or re-configurable in the present disclosure is defined as the capability of being bent (in one or more locations with a bend radius of 0.5" to 30") and being able to change from an old form or shape to a new form or shape when the ion transfer device 20 is actively transferring the ions. In one or more embodiments, flexible or re-configurable (or flexibility or re-configurability) may be defined as the ion transfer device 20 having a plurality of bend positions or the ion transfer device 20 being able to or configured to form at least one curvature. In one or more embodiments, flexibility is defined as the achievable range of motion or being at one or more bend positions without affecting or with minimal change (for example less than 1%, 5%, 10%, or 20%) in the ion transfer efficiency (ion transfer efficiency in one or more embodiment is defined as the ratio of the ions entering to the ions exiting the ion transfer device 20) of the ion transfer device 20, without losing the functionality of the ion transfer device 20, or without shorting electrical connections of the ion transfer device 20 as a result of bending. In one embodiment, flexible is defined as being capable of having a plurality of curvatures around an axis of the ion transfer device 20. In one embodiment, flexibility of the ion transfer device 20 may or may not retain a form or a shape while being flexible or re-configurable. In one or more embodiments, flexibility may be defined as spacing between electrodes of the ion transfer device 20 being increased or decreased. In one or more embodiments, being flexible and being re-configurable may be used in an interchangeable manner.

The ion transfer device 20 has a diameter and a length. The diameter may be the same or different (may gradually increase or decrease or a combination of both) along the ion transfer device 20. In one or more embodiments, the diameter of the ion transfer device 20 may be any value between 0.2 to 2 inches or even up to 5 inches, the length of the ion transfer device 20 may be any value between 0.5 to 1000 inches or may be 0.1 to 500 feet or more. In one or more embodiments, the length may be 1-10, 10-100, or 100-1000 times or more of the diameter (or the largest or the smallest diameter if the diameter varies along the length). The length is defined as the distance between the point the ion transfer device 20 is connected to the ionization source 32, (or for example the ion inlet of the ion transfer device 20) and the point the ion transfer device 20 is connected to the ion guide 13 (or for example the ion outlet of the ion transfer device 20) when the ion transfer device 20 is in the form of a straight-line between these two points. The ion inlet (illustrated in FIG. 4A-D as "ions in") and the ion outlet (illustrated as "ions out") in the present disclosure are defined as the two sides of ion transfer device 20 from which ions respectively enter and exit the ion transfer device 20.

Figure 2B:
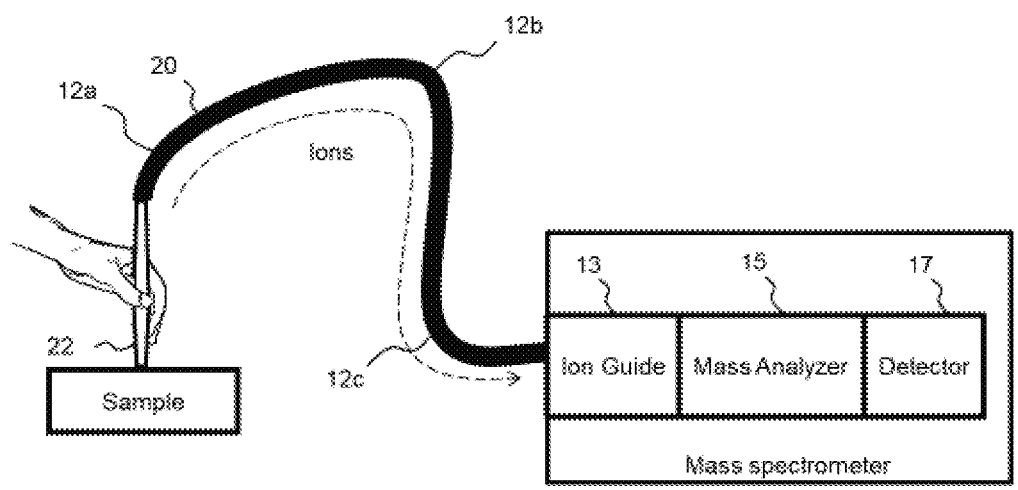
FIG. 2B shows a block diagram of a mass spectrometry system such that the ionization source in form of an ionization source probe is detached from the ion guide and the ions are efficiently transferred to the ion guide via a flexible or re-configurable ion transfer device in accordance with one or more embodiments of the present disclosure.

FIG. 2B shows a block diagram of a mass spectrometry system such that the ionization source probe 22 is detached from the ion guide 13 and ions are efficiently transferred to ion guide 13 via a flexible or re-configurable ion transfer device 20 in accordance with one aspect of the present disclosure. The mass spectrometry system shown in FIG. 2B includes a flexible ion transfer device 20, which may efficiently transfer ions from a hand-held or portable ionization probe 22 to an ion guide 13 of a conventional mass spectrometer that also includes a mass analyzer 15 and a detector 17.

The terms "Efficient" or "efficient transfer" of ions or "efficient ion transfer," or "efficiently transferring ions" or "actively transferring ion" are defined, in one or more embodiments of the present disclosure as the transfer of ions with help of electric fields generated by DC and/or RF and/or alternating current (AC) with no ion loss or with minimal loss (for example <1%, <10%, or <20%-50%). The ion loss may be caused by collisions of ions with the inner walls of the ion transfer device 20 or by colliding with structures disposed inside the ion transfer device 20. In some embodiments, efficient ion transfer may be ion transfer with the ratio of ion exiting the ion outlet of the ion transfer device 20 to the ions entering the ion inlet of the ion transfer device 20 being greater than 0.99, 0.95, 0.90, 0.85, 0.80, 0.5, 0.2 or 0.1. In one or more embodiments, ion transfer efficiency is defined as the ratio of "the ion exiting the outlet of the ion transfer device 20 when all required voltages for the ion transfer device 20 operation is applied" to "the ions exiting the outlet of the ion transfer device 20 when no voltage is applied to the ion transfer device 20" being greater than, for example, 1.5, 2, 3, 10, 50, 500, 1000, or being greater than 1000 or more. In one or more embodiments, efficient may be defined as the percentage of ions exiting the outlet of the ion transfer device 20. The efficiency may be greater than 90%, 50%, or 10%. The number of ions entering the ion inlet or exiting the ion outlet of the ion transfer device 20 may be measured or quantified, for example, by monitoring ion current at the ion inlet or ion outlet of the ion transfer device 20 with ion current detector such as an ammeter, an electrometer, or an electron multiplier. In one or more embodiments, Active ion transfer or actively transferring ions in the present disclosure is defined as transfer of ions with aid of electric fields or potentials created by application of voltages to electrodes of the ion transfer device 20 or when various voltages (such as DC, AC, or RF or a combination of them) are applied to electrodes of the ion transfer device 20. Transfer or movement of ions inside the ion transfer device 20 may be under the effect of electric field, or gas flow due to differential pumping, or a combination of both. Further, ion-ion repulsion or space charge effects may move ions inside the ion transfer device 20, for example, when new ions entering the ion transfer device 20 push forward the ions already inside the ion transfer device 20 due to repulsion of like charges.

The pressure inside the ion transfer device 20 may be in the range of 0.001 to 760 Torr. In this pressure regime, the ions have a relatively small mean free path, (in the order of a few nanometers to several micrometers), and therefore, collision of ions with background gas exists inside the ion transfer device 20 when ions enter the ion transfer device 20. The collision of ions with the background gas (for example air, Ar, He, or Nitrogen molecules) in these pressure regimes results in ions not travelling in straight lines and frequently colliding with background gas molecules and changing path as a result of these collisions. Collisional cooling under these pressure regimes may also be present. A combination of out-of-phase RF voltages, AC voltages in conjunction with DC voltages are used to efficiently guide and transfer the ions inside ion transfer device 20. RF voltages radially push ions towards a central axis of the ion transfer device 20 and maintain the ions around the central axis of the ion transfer device 20, thus reducing the ion loss due to collision with inner walls. While RF voltages and the resulting electric field from RF voltages retain ions in a central axis of the ion transfer device 20 (for example along a longitudinal axis of the ion transfer device 20), the DC voltages may provide a gradient to transfer and guide the ions in a direction towards the ion outlet of the ion transfer device 20.

The ion transfer device 20 may be in a shape of a flexible tube or a flexible bellow with a plurality of electrodes disposed inside the flexible tube or bellow to receive the ions from an ion inlet of the ion transfer device 20 from an ionization source, such as the hand-held ionization probe 22, and then actively transfer the ions to an ion outlet of the ion transfer device 20, where ions then enter the ion guide 13 of the mass spectrometer. In one or more embodiments, "active" transfer or "actively" transferring of ions are defined as transfer of ions with help of electric field (or electric-field-enhanced transfer) that may be produced by DC, AC and/or RF voltages. In one or more embodiments, "active" or "actively" may be interchangeably used with "efficient transfer" as defined in the present disclosure.

Although the present disclosure mainly describes use of a mass spectrometer to describe operation of the ion transfer device 20, however, the present disclosure also relates to an ion mobility spectrometer or any other apparatus that transfers gas-phase ions. Further, the ion transfer device 20 may be used as an ion mobility separation stage for mass spectrometers because the ions may separate based on ion mobility during transfer. Ions in the present disclosure are defined as charged particles, having positive or negative charges. Therefore, a mass spectrometer in all exemplary embodiments may be replaced by an ion mobility spectrometer without changing the scope, or any other apparatus that uses ions or any charged particles. In one or more embodiments, ions are atoms or molecules with a net electric charge due to the loss or gain of one or more electrons, and the atoms or molecules may be the same or different. The ions may be from atomic ions of 10 atomic mass unit (amu) up to large biomolecules with hundreds of thousands of amu mass range.

The ion transfer device 20 may include a tube with one or more layers made from a single material such as a plastic or metal tube or made from multiple materials. In one or more embodiments, the tube may include several layers, for example, 2 to 10 different layers. In one or more embodiments, the tube may be constructed by extruding molten plastic one or more layers of plastic or the electrodes or a tube of the ion transfer device 20. In one or more embodiments, the plastic tube may be manufactured by casting and molding processes and methods such as injection molding with polyurethane or silicone. One or more layers of tubes may be used to provide vacuum-tightness and to provide housing for wires, capacitors, resistors, and electrodes in between different layers of tubing. In one or more embodiments, the tube may contain a metal layer (for example braided metal at ground potential) to contain the electromagnetic radiation. In one or more embodiments, two or more layers of tube is used, and wires connecting the plurality of electrode unit 31*a-j*, as later disclosed in the present application, are passed in between the layers. In one or more embodiments, at least one layer of the tube is a plastic or metal tape wrapped around. In one or more embodiments, the plastic tube may include a heat-shrink tube. Heat-shrink tube may be made of any one of thermoplastics, including silicone, polyolefin, polyvinyl chloride (PVC), Viton® (for high-temp and corrosive environments), Neoprene®, polytetrafluoroethylene (PTFE), fluorinated ethylene propylene (FEP) and Kynar®. In addition to these polymers, some types of heat-shrink may also include an adhesive lining that may help to bond the tubing to underlying electrodes and connectors, forming strong seals that may be waterproof or gas-tight to maintain the required pressure inside the ion transfer tube 20. In one embodiment, the heat-shrink tubing may have conductive polymer thick film to provides electrical connections between the two or more portions of the ion transfer device 20 without the need to soldering and/or to shield the electromagnetic field produced by the RF voltages of the ion transfer device 20.

The sample, as shown in FIG. 2B, may be any arbitrary sample under analysis or test, which the ionization source probe 22 produces ions from, such as a biological sample, a human or animal tissue, geological samples, or any sample of interest that includes a number of analytes of interest. The sample may be a human body part for example a human hand, for example, being screen for skin cancer. The sample may be located on a surface or may be located inside a structure accessed via a hole, for example a small incision in case of biological tissues. The ion transfer device 20 may have or may form a plurality of bend positions 12*a*, 12*b*, 12*c* when handled by a person or a robotic arm of a robot.

Figure 2C:
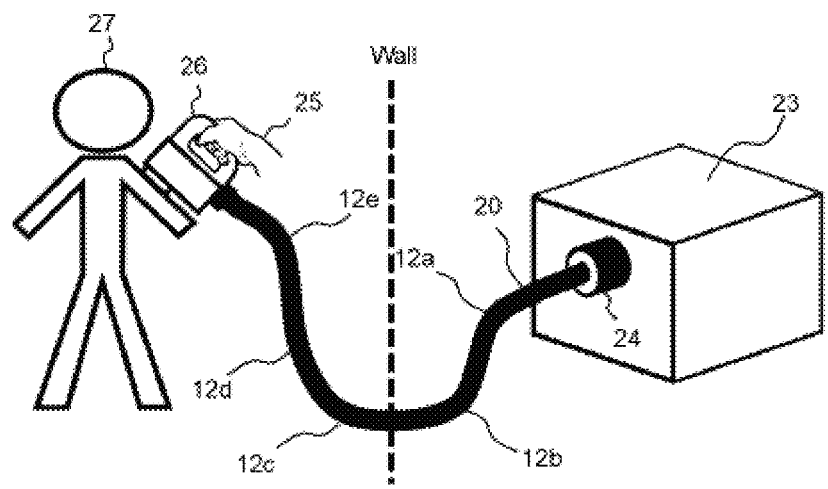
FIG. 2C shows a block diagram of a mass spectrometry system such that the ionization source is detached from the mass spectrometer and the ions produced in an ionization probe are efficiently transferred to the mass spectrometer via a flexible or re-configurable ion transfer device in accordance with one or more embodiments of the present disclosure.

FIG. 2C shows a block diagram of a conventional mass spectrometer 23 such that the ionization source is detached from the mass spectrometer and the ions produced in an ionization probe 26 are transferred to the mass spectrometer 23 via a flexible or re-configurable ion transfer device 20 in accordance with embodiments of the present disclosure. A conventional mass spectrometer 23 is used and the ionization source of the mass spectrometer (which is directly attached to the mass spectrometer 23 in place of an adapter 24) is replaced with the ion transfer device 20 including the adapter 24 on one end (on the ion outlet side) that is connected to the mass spectrometer 23 and an ionization probe 26 at the other end of the ion transfer device 20 (on the ion inlet side). In one embodiment, the adapter 24 (also known as the interface that connects the ion transfer device 20 to the mass spectrometer 23), the ion transfer device 20, and the ionization probe 26 replaces conventional ionization source assemblies provided by mass spectrometer manufacturers (not shown-normally connected where the adapter 24 is connected in FIG. 2C as understood by those skilled in the art) of the mass spectrometer 23. This configuration allows using an ionization probe 26 that may be extended to a distance, for example in a range from 0.1 to 10 m or more depending on a length of the ion transfer device 20, from the mass spectrometer 23, thus enabling easy scanning and analysis of different areas of an object under test 27. The adapter 24 shape may depend on a type of the mass spectrometer 23 and the interface design of a mass spectrometer. For mass spectrometers with one or more ion funnels at the inlet after the heater-capillary, the exit end of the ion transfer device 20 may simply be introduced in the central region inside an ion funnel. In mass spectrometers with double-cone structure, the exit end of the device may be constructed to form an ion funnel structure to further focus the ions into a smaller diameter for their efficient transfer through the one or more cones.

The ion transfer device 20 efficiently transfers the ions produced by the ionization probe 26 to the mass spectrometer 23. The flexible or re-configurable ion transfer device 20 is connected to the mass spectrometer 23 with the adapter 24 that fits the ionization source inlet (or the sampling interface) of the mass spectrometer 23 (where the adapter 24 is connected in FIG. 2C). The ionization probe 26 may be an ambient ionization source, atmospheric pressure ionization source, or a reduced pressure ionization source, which is hand-held, which may be easily held with a hand 25 of an operator or a robot and moved to different locations or parts of an object under test 27. For example, the ionization probe 26 may be freely moved to different parts of a human body so that the ionization probe 26 may become in contact with skin of different parts such as hand or leg of a person 27 so that the ionization probe 26 may produce ions from human skin that is transferred to the mass spectrometer 23 by the ion transfer device 20 for analysis by the mass spectrometer 23. In one or more embodiments, the ionization probe may penetrate the tissue via an incision for in vivo sampling and analysis.

The flexibility of the ion transfer device 20 enables using a hand-held ionization probe 26 and provides several advantages not available in conventional mass spectrometers, thus extending the use of such mass spectrometry systems to many new applications such as clinical applications and in vivo mass spectrometry with high sensitivity. Because conventional mass spectrometers are bulky and because ionization sources of conventional mass spectrometers are directly attached to the mass spectrometer, therefore, in order to in vivo analysis such as analyzing human skin with conventional mass spectrometers, the human must move and bring various body parts to directly in front of a conventional mass spectrometer for testing. This may be difficult, impractical, or impossible in case of such analysis during surgery. The flexible ion transfer device 20, as disclosed herein, enables the ionization probe 26 to flexibly be moved and handled in form of a probe (as disclosed in this application) to different body parts located away from the mass spectrometer 23. This ability to move the ionization source 26 to different locations while maintaining efficient ion transfer enables using conventional mass spectrometers without losing sensitivity (as a result of ion loss) in new applications, such as hospitals and medical offices, for example, for real-time skin analyses during surgery by replacing the conventional ionization sources with the ionization probe 26 which is connected to the mass spectrometer 23 via the flexible ion transfer device 20. Therefore, the mass spectrometer 23 may be located far from the place where the sampling/ionization is taking place by the ion source probe 26. For example, the mass spectrometer 23 may be placed in a separate room and the ion transfer device 20 may transfer the ions using the ion transfer device 20 that is passed through a wall that separates the mass spectrometer 23 from the object under test 27. Further, this approach enables efficient transfer (without losing sensitivity) of ions to the mass spectrometer 23 without or with minimal ion loss, resulting in increased analytical performance, such as better detection limits and sensitivities required for many applications such as in vivo and/or in situ tissue analysis. In other words, the ion transfer device 20 enables extending the ion source 26 of the mass spectrometer 23 away from a mass spectrometer to enable sample analysis from objects 27 that are practically difficult to bring close to the mass spectrometer 23. The object under test 27 may be a patient that is going through surgery on a hospital bed. The ion transfer device 20 may have a plurality of curvatures or bend positions 12a, 12b, 12c, 12d, 12e around which the ion transfer device 20 may form a plurality of curvatures.

Figure 2D:
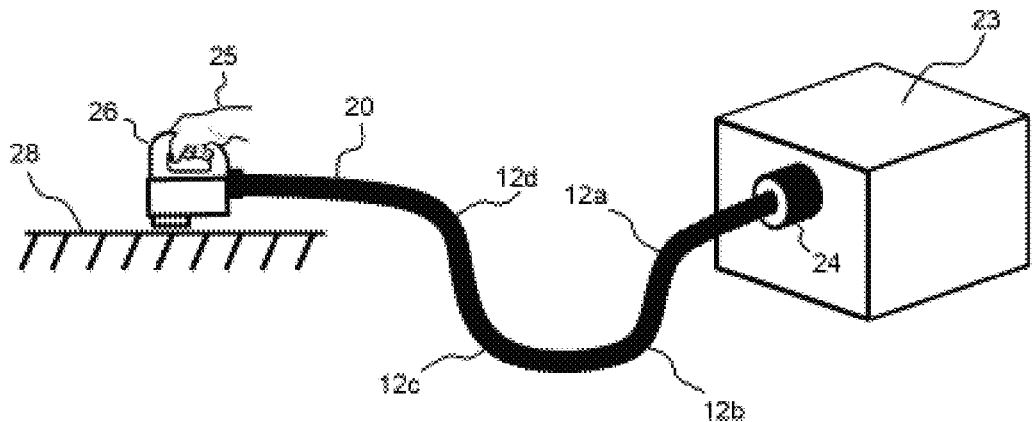
FIG. 2D shows a block diagram of a mass spectrometer such that the ionization source is detached from the mass spectrometer and the ions produced in an ionization probe are efficiently transferred to the mass spectrometer via a flexible or re-configurable ion transfer device in accordance with one or more embodiments of the present disclosure.

FIG. 2D shows a block diagram of a mass spectrometer 23 such that the ionization source is detached from the mass spectrometer and the ions produced in an ionization probe 26 are transferred to the mass spectrometer 23 via a re-configurable ion transfer device 20 in accordance with one or more embodiments of the present disclosure. The ionization probe 26 may be held by a hand 25 of an operator or a user (or for example by a robotic arm of a robot) and a surface of interest 28 may be analyzed without having the mass spectrometer 23 close to the surface of interest 28. The length of the ion transfer device 20 may be greater than 10 cm, 50 cm, 100 cm, 150 cm, or 200 cm, or more. In one or more embodiments, the length of the ion transfer device 20 may be greater than 2 meters, 5 meters, or 10 meters, or more.

The ionization probe 26 produces ions from the surface of interest 28 and the produced ions are transferred via the ion transfer device 20 to the mass spectrometer 23 for analysis. As noted above, this enables modifying the conventional mass spectrometer 23 by replacing the original or conventional ionization sources (not shown) of a conventional mass spectrometer 23 by an adapter 24 that connects the ion transfer device 20 to the mass spectrometer 23 (replaces the original ion source of the instrument) and efficiently transfers the ions from the ionization source probe 26 to the mass spectrometer 23. This allows use of ionization probes 26 that may be freely moved around to scan one or more surfaces of interest 28. For example, at an airport, the ionization source in form of the probe 26 may be used by a security staff at a checkpoint to scan for traces of explosives on passengers, cargo, or luggage In a space rover for planetary exploration in space application, such a configuration enables placing the ionization source 26 on a robotic arm and placing the mass spectrometer 23 on a body of the rover. The ionization source 26 may be used in a manufacturing lines to monitor for the quality or contamination of produced products, such as pharmaceutical products in the production line with one or more ionization sources 26 connected with one or more ion transfer devices 20 to one or more mass spectrometers 23. The ion transfer device 20 may have a plurality of bend positions 12a, 12b, 12c, 12d around which the ion transfer device 20 may form curvatures.

Figure 2E:
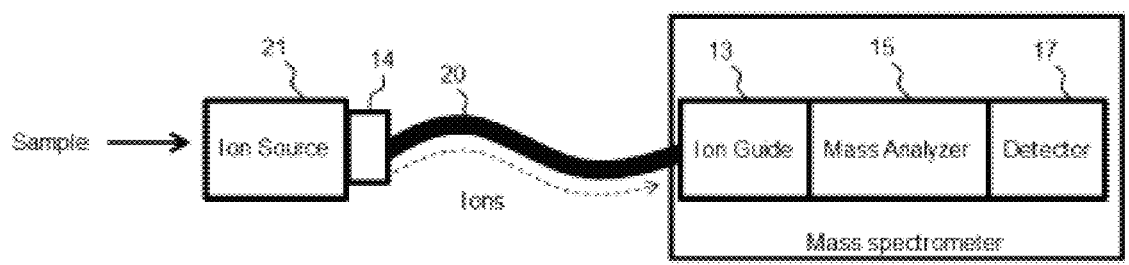
FIG. 2E shows a block diagram of a mass spectrometry system such that the ionization source is detached from the ion guide and the ions are efficiently transferred to ion guide via a flexible or re-configurable ion transfer device in accordance with one or more embodiments of the present disclosure.
Figure 2F:
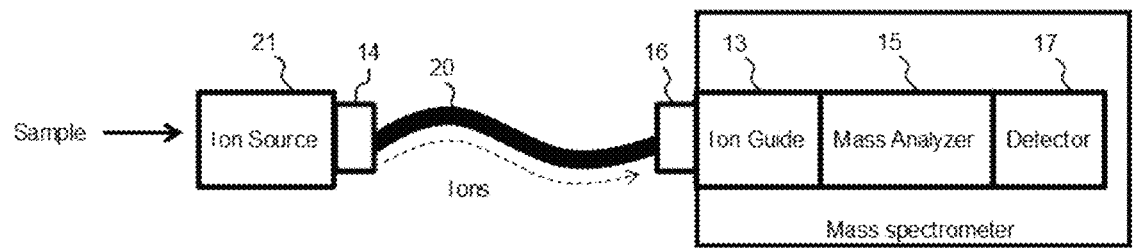
FIG. 2F shows a block diagram of a mass spectrometry system such that the ionization source is detached from the ion guide and the ions are efficiently transferred to ion guide via a flexible or re-configurable ion transfer device in accordance with one or more embodiments of the present disclosure.

FIG. 2E and FIG. 2F show two block diagrams of a mass spectrometry system such that the ionization source 32 is detached from the ion guide 13 and the ions are transferred to ion guide 13 via a re-configurable ion transfer device 20 in accordance with one or more embodiments of the present disclosure. The flexible ion transfer device 20 may have an adapter 14 (including one or more electrodes such as skimmer and sample cones disposed inside, or conventional ion funnels and ion guides) that connects to the ionization source 32 and efficiently transfers ions from the ionization source 32 to the flexible ion transfer device 20. The adapter 14 may also include the electronics necessary to operate the ion transfer device 20, including direct current (DC), alternating current (AC), or radio frequency (RF) voltages for powering and operation of the ion transfer device 20. In one embodiment, the ion transfer device 20 may be connected to a second adapter 16 that connects the ion transfer device 20 to an ion guide 13 of a mass spectrometer. The second adapter 16 may be used to attach the ion transfer device 20 to the mass spectrometer in an air-tight or vacuum-tight manner (for example to maintain a vacuum of minimum 0.01 Torr) while efficiently transferring the ions from the ion transfer device 20 to first vacuum stage of the mass spectrometer. The second adapter 16 may include electronics and connectors necessary to operate the ion transfer device 20 (such as RF and DC voltage power supplies and the related control unit for controlling the power supplies, and/or pogopins or spring contact pins at the interface that the ion transfer device 20 connects to the adapter 16 or adapter 14) or may include one or more electrodes floated at a voltage (such as skimmer and sampler cones, or one or more conventional ion funnels) for efficient transfer and extraction of ions from the ion outlet of the ion transfer device 20 to the ion guide 13 of the mass spectrometer. The first adapter 14 or the second adapter 16 may include electronics and other components necessary to operate the ionization source 32, for example, connectors, electronics for plasma ionization, liquid reservoir for electrospray ionization or laser modules with optical fibers that may be attached to the outer diameter or may be implemented inside or in between the one or more layers of the tube of the ion transfer device 20 (as disclosed elsewhere in the present application) for laser electrospray desorption/ionization, or a combination of them. Wires and optical fibers may be attached to the ion transfer device 20 to reach the ionization source 32 from the mass spectrometer or the adapter 16. This is advantageous for reducing the weight and size of the ionization source 32 that may be constructed in from of an ionization probe 26 used by an operator, which require reduced weight for easy handling, maintenance and service, manipulation, and movement of the ionization source probe 26 by the operator.

Figure 3A:
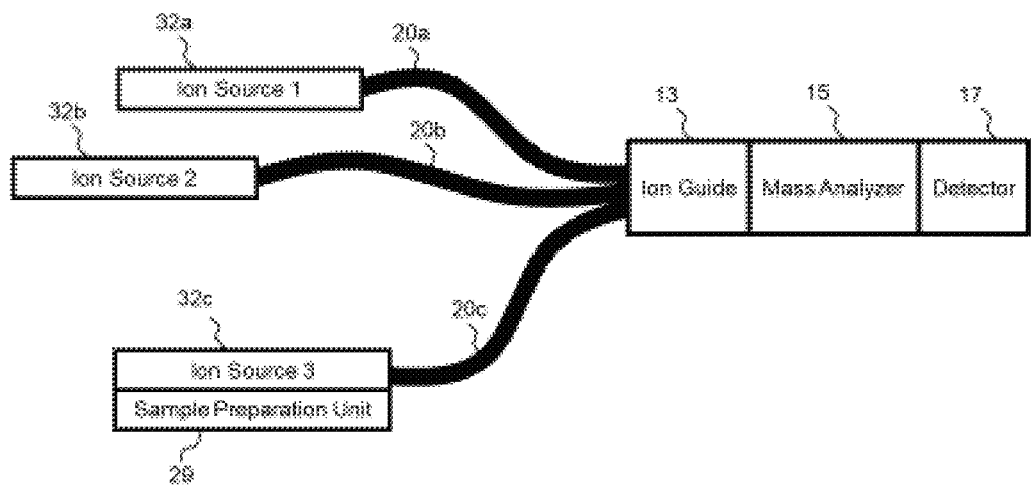
FIG. 3A shows a block diagram of a mass spectrometry system such that three different ionization sources are attached to mass spectrometry system via flexible or re-configurable ion transfer devices in accordance with one or more embodiments of the present disclosure.

FIG. 3A shows a block diagram of a mass spectrometry system such that the three ion sources 32a-c are attached to a mass spectrometer via a re-configurable ion transfer device 20 in accordance with one or more embodiments of the present disclosure. Three ionization sources 32a-c, which may be different or the same located at three different locations, are connected to an ion guide 13 of a mass spectrometer. The ionization sources 32a-c may be different or the same. One or more ionization sources 32a-c may be connected to one or more sample preparation devices 29 to prepare the samples for ionization. For example, the ionization sources 32a-c may be connected one or more sample preparation or separation instruments, such as a high-pressure liquid chromatography system (LC or HPLC system) or a gas chromatography (GC) system to separate analytes before analysis with the mass spectrometer. The ionization sources 32a-c may be operated in a multiplexed manner and each ionization source has a periodic allocated time frame to introduce ions into the mass spectrometer via corresponding ion transfer tube that is attached to the ionization source for analysis. In the present disclosure, the combination of the ion guide 13 the mass analyzer 15 and the detector 17 may be referred as the mass spectrometer. This configuration provides the advantage that a single mass spectrometer may be used to analyze different sample located in different places and coming from different separation or sample preparation instruments as disclosed above. Because analysis by a mass spectrometer is performed in milliseconds to seconds, thus such multiplexing may significantly enhance optimal use of mass spectrometers by continuously and sequentially providing ions from different locations/instruments or ionization sources 32a-c to the mass spectrometer for analysis.

Figure 3B:
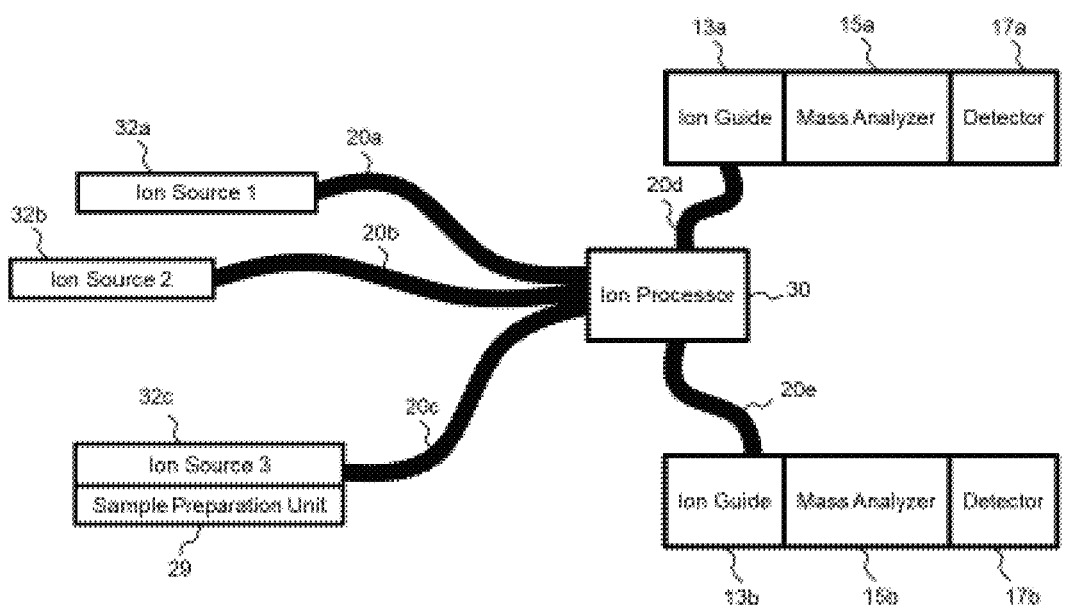
FIG. 3B shows a block diagram of a mass spectrometry system such that three different ionization sources are efficiently transfer ions to two different mass spectrometry systems via flexible or re-configurable ion transfer devices in accordance with one or more embodiments of the present disclosure.

FIG. 3B shows a block diagram of a mass spectrometry system such that the three ionization sources 32a-c are attached to two mass spectrometers via re-configurable ion transfer devices 20a-e in accordance with one or more embodiments of the present disclosure. The ion processor 30 (also referred to as the ion manipulation device in the present disclosure, an example of which is described in U.S. Pat. No. 9,966,244 for lossless ion manipulation (SLIM)) may be used to selectively transfer the ions received from three ionization sources 32a-c respectively connected to three flexible ion transfer devices 20a-c to the ion processor 30. The ion processor 30 then selectively transfers the ions via two flexible ion transfer devices 20d, 20e to, for example, two different mass spectrometers: the first mass spectrometer including the ion guide 13a, the mass analyzer 15a and the detector 17a, and the second one including the ion guide 13b, the mass analyzer 15b and the detector 17b, as shown in FIG. 3B. The ion processor 30 may trap, store, process (for example separate ions based on their mobility), and selectively transfers ion packets into these two mass spectrometers. The two mass spectrometers may have the same or different analyzers 15a-b.

Figure 3C:
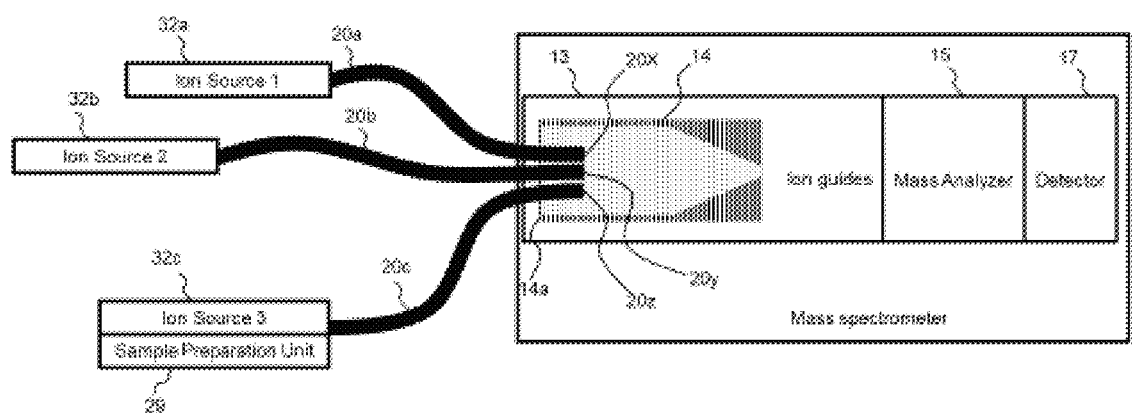
FIG. 3C shows a block diagram of a mass spectrometry system such that three different ionization sources are attached to mass spectrometry system via flexible or reconfigurable ion transfer devices in accordance with one or more embodiments of the present disclosure.

FIG. 3C shows a block diagram of a mass spectrometry system such that three different ionization sources 32a-c are connected to ion guides 13 of a mass spectrometer via three flexible or re-configurable ion transfer devices 20a-c in accordance with one or more embodiments of the present disclosure such that the three ion transfer devices 20a-c enter an ion funnel 14 of the ion guides 13. The ion guides 13 may have one or more multipole ion guides after the ion funnel 14. The diameter of the entrance 14a of the ion funnel 14 may be the same or larger than the diameter of the ion outlet 20x or all the ion outlet 20x-z combined of the three ion transfer devices 20a-c. Such connection of the three ion transfer devices 20a-c to an ion funnel 14 provide the advantage that interfacing is simple and the ions from the three ion transfer devices 20a-c are simply provided into the ion funnel for collection and focusing for transferring to the next stages (may be one or more ion funnels or ion guides downstream to the ion funnel 14) of the mass spectrometer. The interface region (the region the ion outlet 20x-z are introduced into or to a proximity of ion funnel 14 where the distance between the ion outlet 20*x-z* and first ring 14*a* of ion funnel 14 may be any value between 0 and 10 inches or more) may be made by introducing or positioning the ion outlets 20*x-z* of the ion transfer devices 20*a-b* directly into the ion funnel 14 of the mass spectrometer, as shown in FIG. 3C. In one or more embodiments, the first entrance ring 14*a* of the ion funnel and the last electrodes on the ion outlets 20*x-z* of the ion transfer device 20*a-c* may be constructed on the same substrate. Although FIG. 3C illustrates interfacing three ion transfer devices 20*a-c* to an ion funnel, any number of ion transfer devices 20 may be connected to a mass spectrometer. The configuration disclosed herein that enables connecting two or more the same or different ionization sources 32*a-c* to the mass spectrometer via the ion transfer devices 20*a-c* provides the advantage that performance of the ionization sources 32*a-c* may be compared to each other simultaneously, for example, in case ions are produced from a single sample with different ionization methods. Further, the ionization methods of each of the ionization sources 32*a-c* may be different o provide complementary chemical composition information of the sample. Further, this configuration provides the advantage that a single mass spectrometer may be shared by different operators using different ionization sources or probes 32*a-c* at different locations, and therefore, reducing the cost of acquisition and operation of a mass spectrometer. Any custom-made or commercially-available mass spectrometer or ion mobility spectrometer may be interfaced and used as the "mass spectrometer" in the present disclosure such as quadrupole mass analyzer, time of flight mass analyzer, magnetic sector mass analyzer, electrostatic sector mass analyzer, Orbitrap®, quadrupole ion trap mass analyzers, ion cyclotron resonance, or field asymmetric ion mobility spectrometry.

Figure 4A:
FIG. 4A, FIG. 4B, FIG. 4C, and FIG. 4D show block diagrams of different configurations for ion transfer devices in accordance with one or more embodiments of the present disclosure.

FIG. 4A shows a block diagram of an ion transfer device 20 in accordance with one or more embodiments of the present disclosure. The ion transfer device 20 may include at least an electrode unit 31. In the present disclosure, each electrode unit may be defined as an assembly of individual electrodes or an assembly of one or more electrodes connected to one or more voltages such that each of the individual electrodes may or may not have connectors, capacitors, and resistors. The one or more voltages may be supplied to each of the electrode units 31 via electrical connection, for example, at one or both ends of the ion transfer device 20. One or more wires may be also wrapped around or pass along the ion transfer device 20 to supply power at some points along the ion transfer device 20 to electrodes units of the ion transfer device 20 in between layers of an enclosure 21 as disclosed in the present application. The ion transfer device 20 may include an ion transfer enclosure 21. The ion transfer enclosure 21 may be a tube made from, for example, plastic or metal that may be connected to a voltage or ground if the tube is made from metal or conductive plastic (grounded or floated at a voltage). In one or more embodiments, the ion transfer enclosure 21 may also include tubing layers or jackets to restrict the bend radius of the ion transfer device 20, for example, to 0.5" to 30" bend radius. In one or more embodiments, the ion transfer enclosure 21 may also include tubing layers or jackets to protect the ion transfer device 20 from impact. The ion transfer enclosure 21 may include a plurality of tubes. The ion transfer enclosure 21 may be a soft or a corrugated tubing or in bellow form (for example vacuum bellows) to allow flexible bending of the ion transfer enclosure 21 and the ion transfer device 20 to produce a plurality of curvatures. The ion transfer enclosure 21 may be constructed from one or more heat-shrink tubes. The ion transfer enclosure 21 (or simply referred to as the enclosure) seals and/or maintains the one or more electrode units 31 in reduced pressure (or intermediate pressure, also known as fore-vacuum pressure mass spectrometer, below 760 Torr) and also provides a mechanical structure to support and protect the electrode unit 31 and the corresponding assemblies as those shown in the drawings in the present application. The pressure level inside the ion transfer enclosure 21 may be maintained between in a range from 0.001 Torr to 760 Torr, for example in a range from 0.01 to 30 Torr. One or more vacuum pumps may be connected to and maintain vacuum inside the enclosure 21 and/or the ion transfer device 20 at different locations along the ion transfer device 20 or at the two ends of the ion transfer device 20. In one or more embodiments, one or more vacuum pumps may be connected to the ion inlet side (indicated as "ions in" in FIG. 4A-D) and/or the ion outlet side (indicated as "ions out" in FIG. 4A-D) and/or one or more locations along the ion transfer device 20 in between the ion inlet or the ion outlet, for example, in a middle portion of the enclosure 21. The pressure inside the ion transfer device 20 may be maintained the same or different at different locations inside the enclosure 21 along the ion transfer device 20. For example, the pressure at ion inlet may be maintained at 1-20 Torr and at the ion outlet may be maintained at 0.1-10. A differential pressure via differential pumping may be maintained along the ion transfer device 20 to produce a gas flow from higher pressure to lower pressure air transfer of ions along the ion transfer device 20 to aid transferring ions in the ion transfer device 20. The pressure inside the enclosure may be in a range from 0.01 to 30 Torr. The electrode units of the ion transfer device may have one or more jet disrupters to disrupt the movement of neutrals in the flow inside the ion transfer device 20.

The electrode unit 31 may be flexible or may be flexibly connected for flexible bending along with the ion transfer enclosure 21. The ion transfer device 20 may include one electrode unit 31 having two or more electrodes, which may be flexible electrodes, such as those shown, and disclosed later in the present application. In one or more embodiments, the one electrode unit includes a plurality of electrodes that are flexibly connected to each other or the enclosure 21, examples of which are shown in FIG. 6A-D, FIG. 7A-B, FIG. 9A-Z, FIG. 10A-b, FIG. 13, FIG. 15A-C, and/or FIG. 16 as disclosed in the present application. The enclosure 21 may be bent to have, at least one, or two or more different shapes or forms or configurations to have a plurality of curvatures (which may also be referred to as a plurality of twists, arcs, bends, or curves).

Figure 4B:
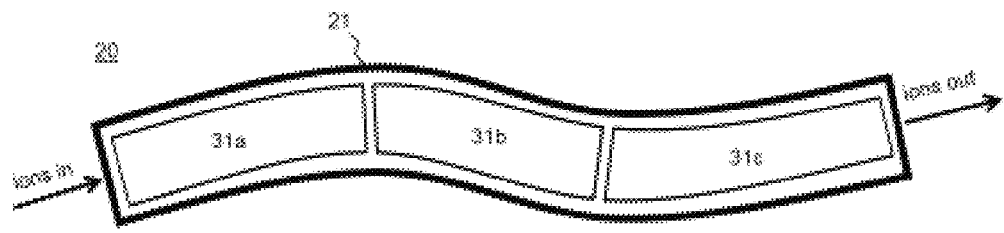
Figure 4C:
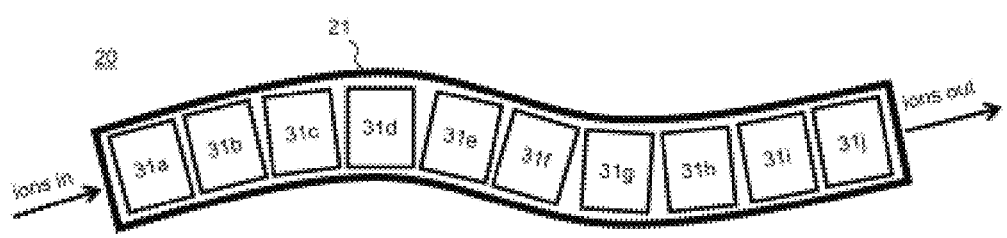

FIG. 4B and FIG. 4C show two block diagrams of embodiments of the ion transfer device 20 in accordance with one or more embodiments of the present disclosure. The ion transfer device 20 may include a plurality of electrode units 31*a-c* in FIG. 4B or 31*a-j* in FIG. 4C that are connected to each other. Each of the plurality of electrode units 31*a-j* may include a plurality of electrodes, which may be flexible electrodes, such as those shown, and disclosed in the present application. In one or more embodiments, the ion transfer device 20 may include a plurality of electrodes that are flexibly connected to each other or the enclosure 21, as disclosed in the present application. The plurality of electrode units 31*a-j* and the enclosure 21 may be flexible or bendable or re-configurable from a first shape or configuration to a second shape or configuration. In one or more embodiments, the plurality of electrode unit 31*a-j* may be not flexible or re-configurable but flexibly connected to each other to provide flexibility to the ion transfer device 20. A long ion transfer device in the present application may comprise one or more ion transfer devices 20 connected to each other in series, each of the one or more ion transfer devices 20 may have connectors for making connections on two sides such that the connection supports vacuum and also makes the electrical connections.

Figure 4D:
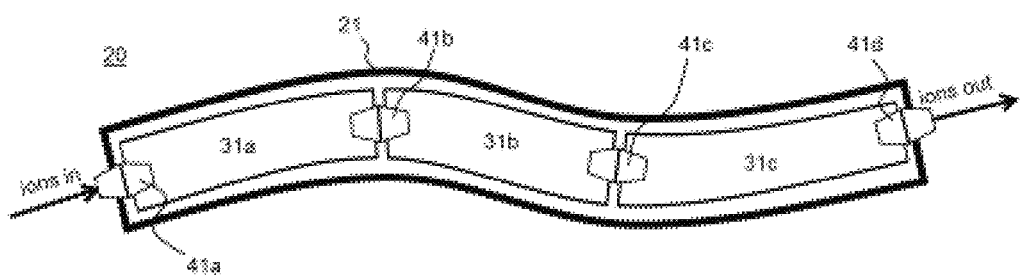

FIG. 4D shows a block diagram of an ion transfer device 20 in accordance with one aspect of the present disclosure. In one embodiment, a plurality of connecting or interface electrodes segments 41a-d, which may or may not be electrically isolated from the plurality of electrode units 31a-j, and may be individually connected to different voltages, connect the plurality of electrode units 31a-c. In one embodiment, the plurality of connecting electrodes segments 41a-d may facilitate efficient transfer of ions between two neighboring electrode units (31a and 31b) and/or (31b and 31c). The plurality of connecting electrodes segments 41a-d may be in form of skimmer cones or conductance limiting orifices and similar structures used in differential pumping in conventional mass spectrometers. In one or more embodiments, the plurality of connecting electrodes segments 41a-d, may be one or more conductance limiting orifices or a plurality of capillary tubes. In one or more embodiments, the plurality of connecting electrodes segments 41a-d may be the electrodes of the that gradually decrease in inner diameter, similar to those of ion funnels.

Figure 5A:
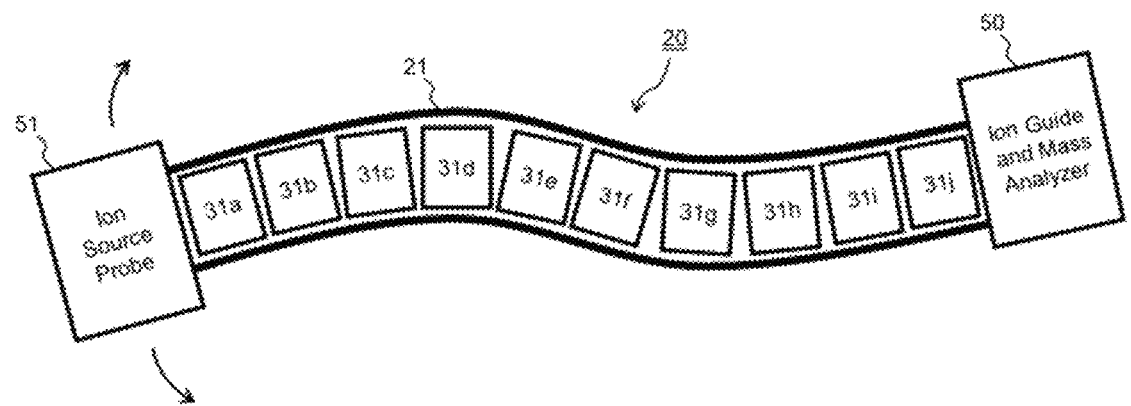
FIG. 5A, FIG. 5B, and FIG. 5C show block diagrams of different configurations of ion transfer device in accordance with one or more embodiments of the present disclosure.
Figure 5B:
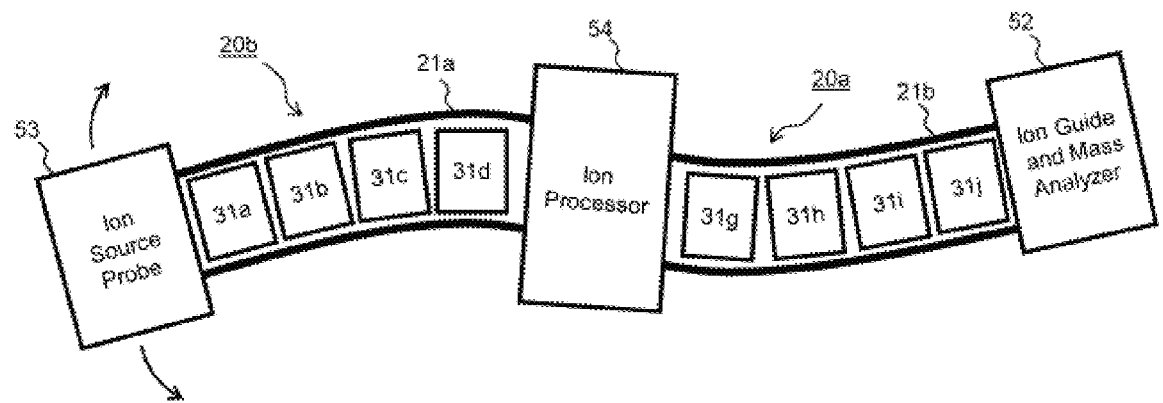
Figure 5C:
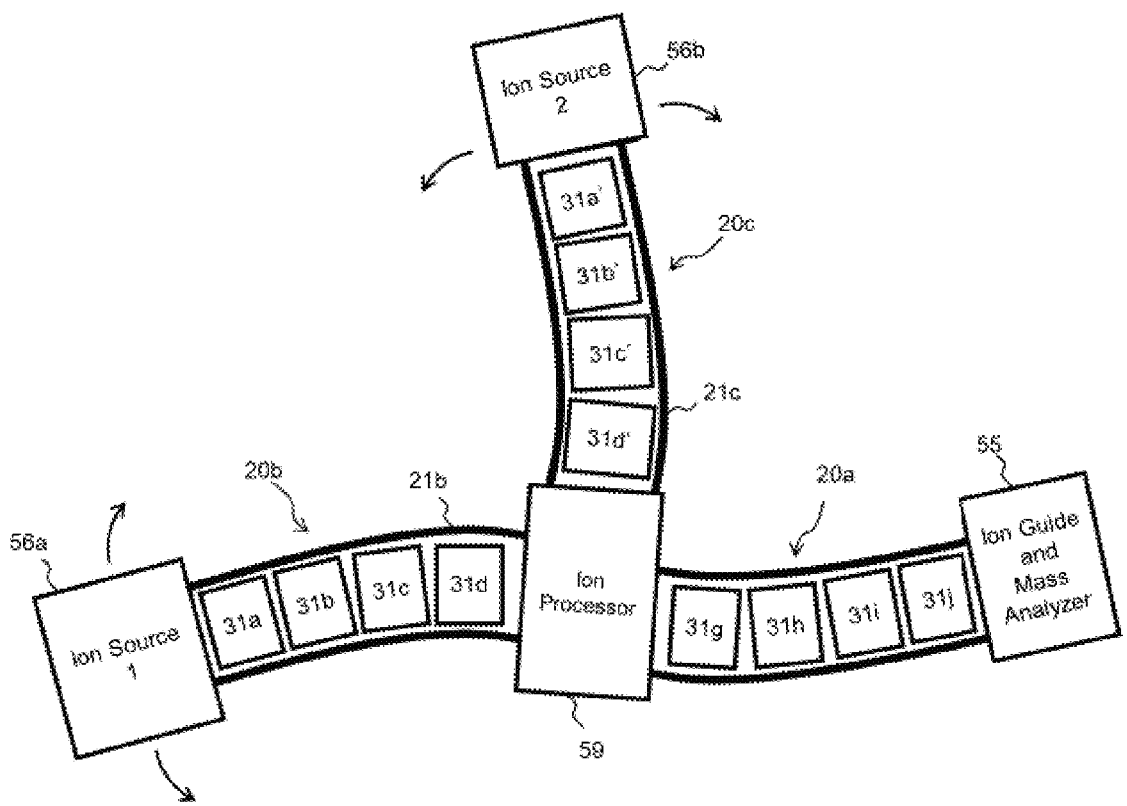

FIG. 5A, FIG. 5B, and FIG. 5C show three block diagrams of different embodiments of the ion transfer device 20 connections to the mass spectrometers 50, 52, 55 in accordance with one or more embodiments of the present disclosure. The ion transfer devices 20a-b may include a plurality of electrode units 31a-j, as disclosed above, that are connected to each other. Each of the plurality of electrode units 31a-j may be flexible or may be rigid and flexibly connected to each other, as described above, and are located, at least partially, inside the enclosure 21. The plurality of electrode units 31a-j and the enclosure 21 may be bent to have two or more different shapes (forms or configurations) and may be reconfigurable or flexible. The ion transfer device 20 may be connected at one end to the ionization source probe 51 that may freely move in 3-dimensional space because of the flexibility of the ion transfer device 20. The ionization source probe 51 may be flexibly moved around to bring the ionization source probe 51 close to sample or object under test to be analyzed. Further, the ion transfer device 20 may be connected to ion guide and mass analyzer of a mass spectrometer 50. The flexibility of ion transfer device 20 enables either to fix the mass spectrometer and move the ion source or fix the ion source and move the mass spectrometer, or both.

In one embodiment shown in FIG. 5B, an ion processor 54 may be included and the ion processor, ion manipulator, or ion mobility separator (as describes above regarding U.S. Pat. No. 9,966,244) may be connected to the ionization source probe 53 on one end and the mass spectrometer 52 on the other end using two different ion transfer devices 20a-b so that flow or pre-separation of ions (based on their ion mobility in the ion processor 54) may be controlled. FIG. 5C is similar to FIG. 5B with the modification that the ion processor 59 is connected to two different ionization sources 56a-b, and multiplexes the ions received from these two ionization sources to the mass spectrometer 55.

FIG. 6A, FIG. 6B, FIG. 6C, and FIG. 6D show perspective views of one or more embodiments of the flexible or re-configurable ion transfer device 20, in accordance with one or more embodiments of the present disclosure. In one or more embodiments, the plurality of electrodes 63 each having a central hole 65 (of the same or different diameter, for example ascending or descending diameters, at least one of which may also act as conductance limiting orifice to limit gas flow between two adjacent electrode units and provide differential pressure in two adjacent electrode units while focusing ions) may be connected to each other using wires or rods 61a-d, which go through a plurality of holes 62 (or half-holes) provided on each of the plurality of the electrodes 63. In one or more embodiments, the electrodes 63 may be made of printed circuit board (PCB) that also may include the components (for example resistors 69 and capacitors 70a-b). The ion transfer device 20 having a number of electrodes 63, for example any value between 1 and 1000 or more electrodes, may also be considered or defined or constitute as the electrode unit 31a-j as previously disclosed. The electrode units of the ion transfer device 20 disclosed in this application may have the same or different number of electrodes. The two electrodes 63 at the two ends of each electrode unit 31a-j may be referred to as the entrance and exit electrodes, ion inlet and ion outlet electrodes, or the first and the last electrode in the present disclosure.

In one or more embodiments, the rods 61a-d may be replaced with conductive or non-conductive spring connectors to connect two adjacent electrodes 63. The conductive spring connectors may also act as wires or electrical connection 68 to supply voltages to the electrodes 63. The plurality of electrodes 63 are disposed at least partially or fully inside one or more flexible tube or enclosure 67 (also referred to as tube in the present application). The tube or enclosure 67 may not be shown in some drawings of the present disclosure for simplicity of illustration. The tube or enclosure 67 may be made of anti-static material to prevent buildup of charge on the enclosure 67 that may expose inside the ion transfer device 20. This configuration allows the plurality of the electrodes to form one or more curvatures around an axis 66 of the ion transfer device 20, as shown in FIG. 6C and FIG. 6D. The bend radius may be in the range of 0.5" to 50". The enclosure 67 may also limit the bend radius to a value in the range to or to a maximum of 0.5" to 50". The plurality of electrodes 63 each may have one or more electrical connection 68 to apply different voltages, such as RF voltages VRF1 and VRF2, and DC voltages, VDC1 and VDC2. In one or more embodiments, the electrical connection 68 are conductive pads that are part of the electrodes 63. The plurality of electrodes 63 may be made from any metal (stainless steel, nickel, copper, gold, or any other metal with or without coatings), any conductive material such as conductive plastic, or a combination thereof. In one or more embodiments, the plurality of electrodes 63 may be printed circuit board that also include the capacitors 70a-b and resistors 69. The spacing between the electrodes may be different or may be the same and may be a value between 0.1 mm to 10 mm. The thickness of electrodes may be different or may be the same and may be a value between 0.1 mm to 3 mm. The central hole 65 or the plurality of holes 62 (or half-holes) may be metal plated, for example gold-plated, to provide a conductive and/or smooth surface.

Figure 6A:
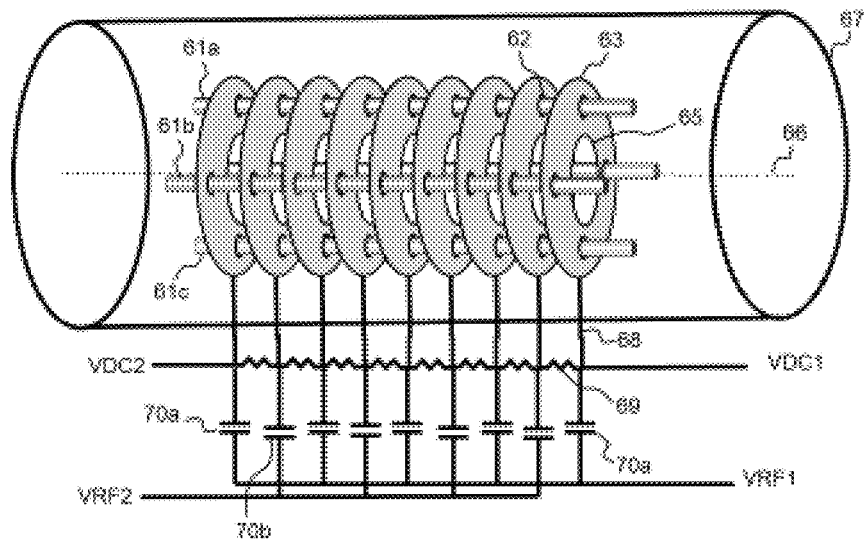
FIG. 6A, FIG. 6B, FIG. 6C, and FIG. 6D show perspective views of flexible or re-configurable ion transfer device in accordance with one or more embodiments of the present disclosure.
Figure 6B:
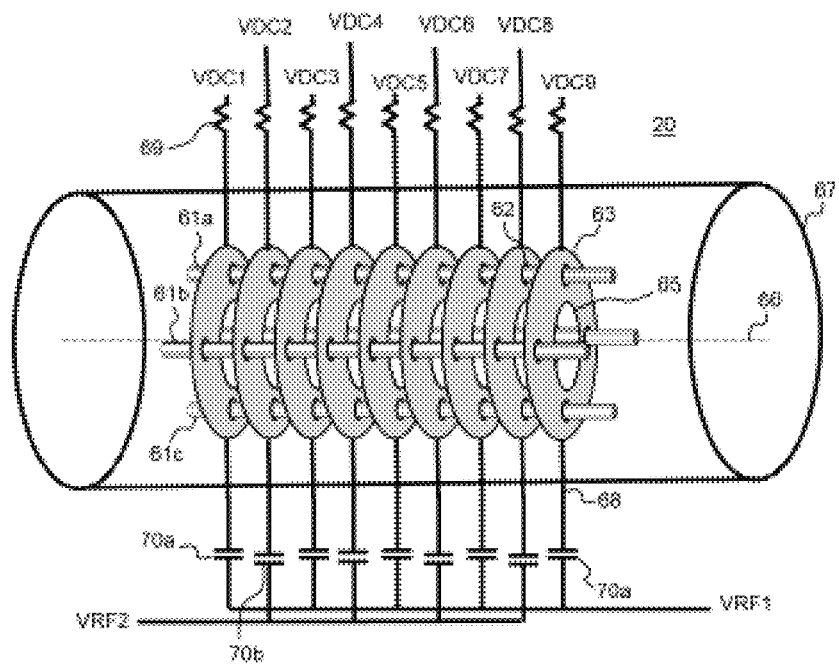
Figure 6C:
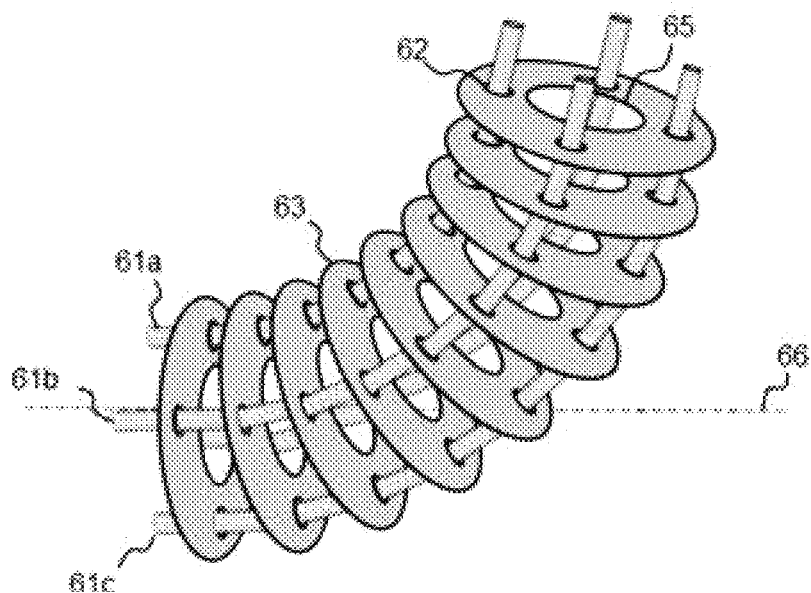
Figure 6D:
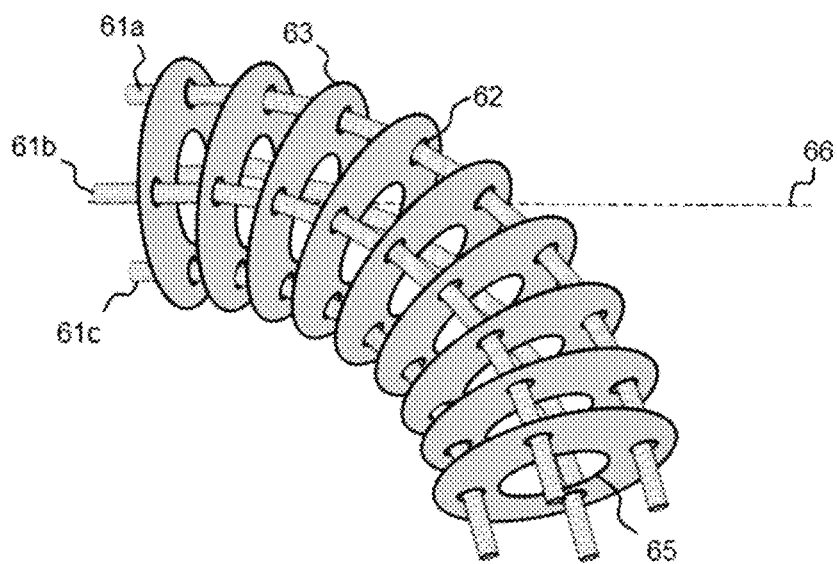

RF voltages may be applied by connecting a plurality of capacitors 70a-b in series to the electrical connections 68, which are connected to electrodes 63, as shown in FIG. 6A and FIG. 6B. The capacitors 70a-b may have a value of 1 to 1000 pF. The DC voltages may be applied by connecting resistors in series with the electrical connections 68, as shown in FIG. 6A. In one or more embodiments, the resistors 69 are connected in series in two parallel resistor series that one of the resistors series are connected to the electrodes 63 having an odd number and the other one of the resistors series are connected to the electrodes 63 having an even number and the two resistor series are connected to each other at the two end. In one or more embodiments not shown here, the odd electrodes and even electrodes are connected to each other with two separate voltage divider resistor networks which are connected at the two ends. The resistor value may be 0.01M to 10M Ohms.

The capacitors 70a-b and resistors 69 may be connected by connectors, soldering, or spot-welding to the electrodes 63 or the electrical connections 68 instead of using the electrical connections 68. Alternatively, the capacitors 70a-b and resistors 69 may be assembled on a flexible or rigid printed circuit board (PCB) and connected to the holes 65 or the electrodes' metal-plated through hole 84, as shown for example, in FIG. 8A, FIG. 8B, and FIG. 8C.

Application of DC voltages may be to the first and last electrodes of the plurality of electrodes 63, as shown in FIG. 6A by annotations VDC1 and VDC2. In one embodiment shown in FIG. 6B, each electrode of the plurality of electrodes 63 in the electrode units 31a-j is connected to a separate controllable and addressable DC voltages (VDC1 to VDC9) to provide different voltages to each of the plurality of electrodes 63. An absolute value of the DC voltages may be any value from 1 to 500 volts or greater than 500V, either positive (for transferring positive ions) or negative (for transferring negative ions). In one or more embodiments, the DC voltages may be varied in time to time-dependent to produce an AC wave in form of a saw-wave or triangle wave, or pulse wave. The RF voltages (for example sinusoidal or pulse or square wave) may be applied as two out-of-phase RF voltages respectively connected to odd and even electrodes (VRF1 and VRF2). The amplitude of the RF voltage may be any value from 1 to 500 volts or greater than 500V. The frequency of the RF voltage may be any frequency from 100 KHz to 20 MHz, for example 500 KHz. Preferably the RF and DC voltages should not cause gas breakdown at a pressure that the ion transfer device 20 is operating at.

In one or more embodiments, the plurality of electrodes 63 are connected to each other as shown in FIG. 6A but instead of using the rods 61a-d (which may be flexible or elastic), a plurality of electrically insulating or conductive structures (for example elastic or rigid Viton or PTFE O-rings or any similar material, or conductive spring connectors) are placed in between each two electrodes of the plurality of electrodes 63, or a combination thereof. In one or more embodiments this is performed similar to the electrically insulating structures shown by annotations 92a-d in FIG. 9A and FIG. 9B). Each of the electrically insulating structures, such as each O-ring, may be glued to one side of each electrode 63 to hold the electrically insulating structures in place. This helps in prevent the electrically insulating structures from moving or being exposed to the ions passing through the ion transfer device 20 (also known as exposed dielectric charging effect). In the flexible ion transfer device 20, the electrically insulating structures are preferably not exposed to the ions to avoid charging effects, which results from accumulation of charged particles on the electrically insulating structures, and may reform the shape of electric fields, and therefore ion trajectories. Therefore, the inner diameters of the electrically insulating structures are larger than the diameter of the holes 65, 72, 83 or 94) so that if charge accumulation occurs (for example on the electrically insulating structures shown by annotations 92a-d in FIG. 9A and FIG. 9B), the charge accumulation does not adversely affect the electric fields inside the ion transfer device 20. In one embodiment, the resistors and capacitors are directly placed and connected to the electrodes 63 without the electrical connections 68, similar to those shown in FIG. 8A, FIG. 8B, and FIG. 8C and the corresponding disclosure in this application.

To assemble the structure, the plurality of electrodes 63 and the electrically insulating structures (which may be optional) may be assembled on a cylindrical holder or jig (not shown), and then after assembly of the electrodes and connecting the necessary electrical connections and components (resistors and capacitors) are completed, the assembly may be inserted into a heat-shrink tube (which is shown by annotation 67 in one or more embodiments) so that by application of heat, the heat-shrink tube 67 to shrink and hold the assembly in place. The jig may be hollow and include punctures to also provide vacuum during heat shrinking process. In one or more embodiments, two or more layers of heat-shrink tubing may be used. Then, the cylindrical holder may be removed. Such an assembly with one or more heat-shrink tubes holds the electrodes in place and also provides flexibility and re-configurability. Further, using heat-shrink tubing may eliminate the need for having electrically insulating structures (for example annotations 92a-d in FIG. 9C) in between the electrodes to keep the electrodes separate as the heat-shrink, upon application of heat and shrinking, holds the electrodes in place and acts like electrically insulating structures to make the electrodes in place while providing the flexibility as disclosed in the present application, as shown in FIG. 9C, in which the heat-shrink tube shrink into the area in between two adjacent electrodes 91.

Figure 7A:
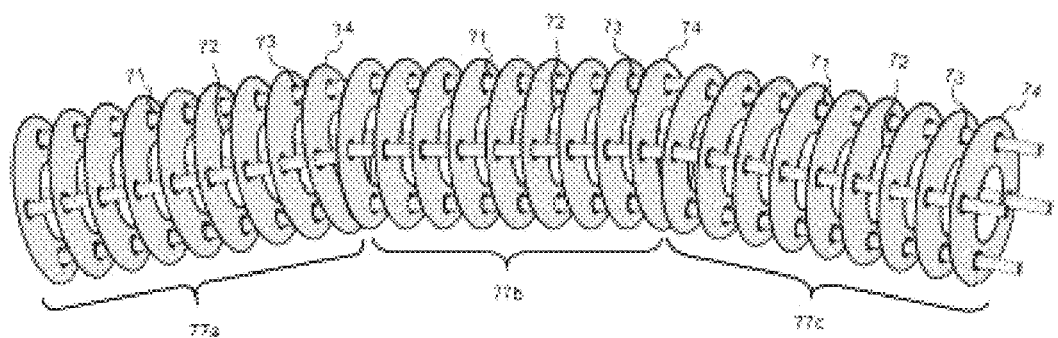
FIG. 7A and FIG. 7B show perspective views of flexible or re-configurable ion transfer device in accordance with one or more embodiments of the present disclosure.
Figure 7B:
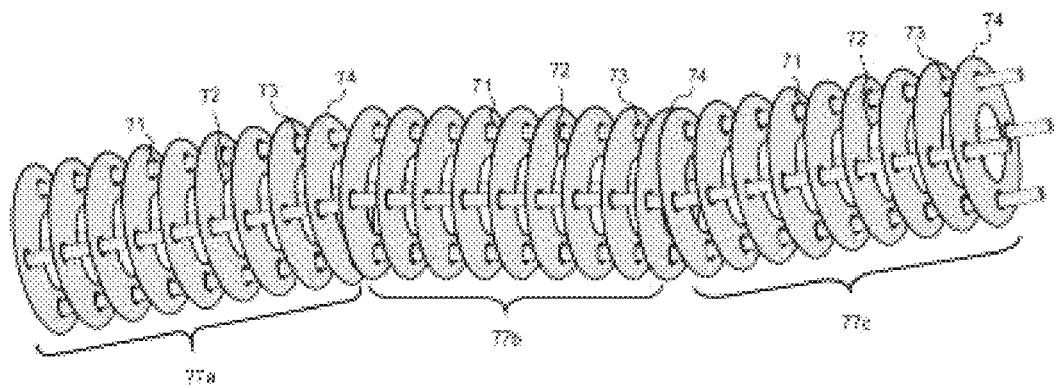

FIG. 7A and FIG. 7B show perspective views of the flexible or re-configurable ion transfer device 20 in accordance with one or more embodiments of the present disclosure. In this exemplary embodiment, instead of having all of the plurality of electrodes flexibly attached to each other (like those embodiments shown in FIG. 6A, FIG. 6B, FIG. 6C, and FIG. 6D), the ion transfer device 20 may include electrode units (or assemblies) 77a, 77b, 77c in which the electrodes 74 are rigidly attached to each other, and the electrode units 77a, 77b, 77c (electrode units are also referred to as electrode assemblies in the present disclosure) are flexibly attached to each other. The plurality of electrodes 74 each having a central hole 72 may be connected to adjacent electrodes using rigid rods 61a-d, which go through a plurality of holes 73 provided on each of the plurality of the electrodes 74. In one or more embodiments, the electrodes 74 may be fixed to each other with glue, epoxy, or screws while maintaining a predetermined spacing in a range of 0.05 mm to 5 mm between the electrodes 74. The electrode assemblies (units) 77a, 77b, 77c are flexibly attached to each other and provide flexibility or re-configurability.

Figure 8A:
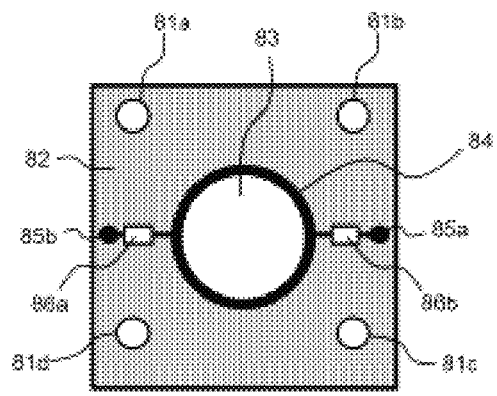
FIG. 8A, FIG. 8B, and FIG. 8C show front views of electrodes of flexible or re-configurable ion transfer device in accordance with one or more embodiments of the present disclosure.
Figure 8B:
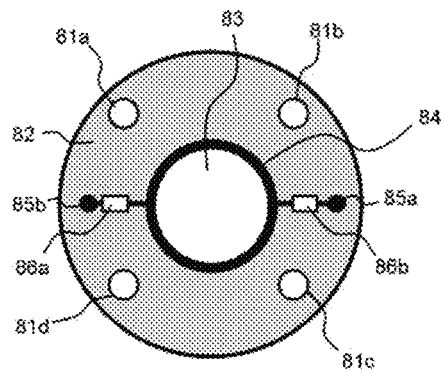
Figure 8C:
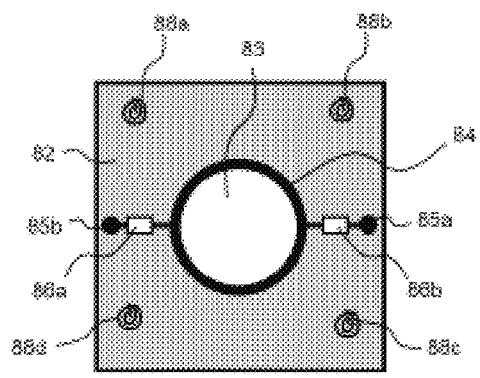

FIG. 8A, FIG. 8B, and FIG. 8C show front views of three embodiments of the electrodes of the flexible or re-configurable ion transfer device 20 in accordance with one or more embodiments of the present disclosure. In one embodiment shown in FIG. 8A, a printed circuit board (PCB) electrode 82 of the plurality of electrodes may be made from PCB. The PCB electrode 82 may include a plurality of holes 81a-d that provide a path for the rods 61a-d. A center hole 83 in the PCB electrode 82 provides a path for ions in the center area of the PCB electrode 82. Around the center hole 83, a metal-plated through hole 84 acts as a conductive electrode for application of voltages to produce electric fields in and around the center hole 83 necessary for transferring ions. The metal-plated through hole 84, which may be copper, metal plating, or gold-immersion plated through hole electrodes used in PCB manufacturing similar to through-hole assemblies well-known in PCB production but with much larger diameter. The diameter of the hole 83 may be a value between 0.2 inches to 10 inches, for example, 0.5". A resistor 86a and a capacitor 86b may be assembled on the PCB electrode 82 to provide the necessary DC voltage and RF voltage, respectively. A plurality of connectors 85a-b connect to adjacent PCB electrode 82 or DC and RF power supplies to provide the required voltages. In one or more embodiments, connectors 85a-b are spring connectors that are soldered to two adjacent electrodes 82 for providing electrical connection between the two adjacent electrodes 82 and also to provide flexibility to the ion transfer device 20. The center holes may be large relative to the interelectrode spacing, for example, to compensate for the axial rf potential wells. The ratio of the diameter of the center boles 94 (or the smallest center hole 94 in case the diameters of center holes are unequal) to the interelectrode spacing may be greater than 1-5 or 5 or more, for example 10. In one or more embodiments, the ratio of the diameter of the center holes 94 (or the smallest center hole 94 in case the diameters of center holes are unequal) to the interelectrode spacing may be equal to or greater than 2, for example in a range of 2-10, 10-100, or more. This provide the advantage that the axial pseudopotential well depth that may hinder transmission of low m/z species is reduced to achieve broad and unbiased m/z transmission via the ion transfer device 20.

In one embodiment shown in FIG. 8B, a PCB electrode 82 of the plurality of electrodes 63 may be circular shape In one or more embodiments, the metal-plated through hole 84 may be square or any arbitrary shape. One of ordinary skill in the art would recognize that the shapes may be made in any arbitrary shape and therefore the drawing is not intended to limit the scope of the present application. In one embodiment shown in FIG. 8C, a PCB electrode 82 of the plurality of electrodes 63, instead of a plurality of holes 81a-d that provide a path for the rods 61a-d (as shown in FIG. 8A with annotations 81a-d), the PCB electrode 82 may include a plurality of electrically insulated or conductive structures 88a-d to flexibly connect two adjacent PCB electrodes 82. The plurality of electrically insulated or conductive structures 88a-d may be made with pogo-pins, spring connectors, or elastic balls, or O-rings attached to the board. In one or more embodiments, the structures 88a-d may be used to provide electrical connection between the two adjacent electrodes 63 for the RF and DC voltages.

Figure 9A:
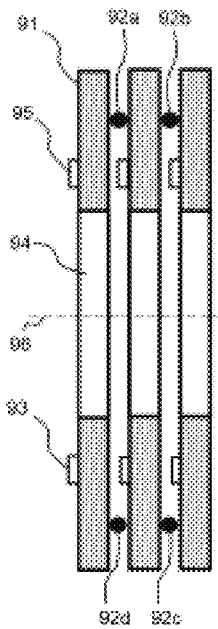
FIG. 9A, FIG. 9B, FIG. 9C, FIG. 9D, and FIG. 9E show cross-section views of electrodes of flexible or re-configurable ion transfer device connected to each other in accordance with one or more embodiments of the present disclosure.
Figure 9B:
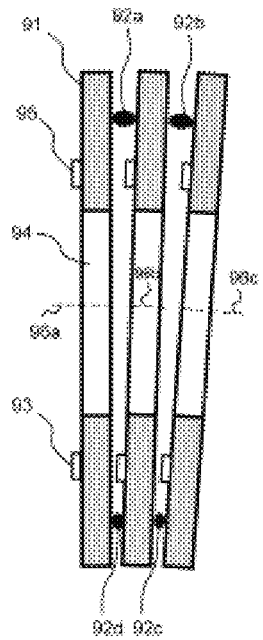
Figure 9C:
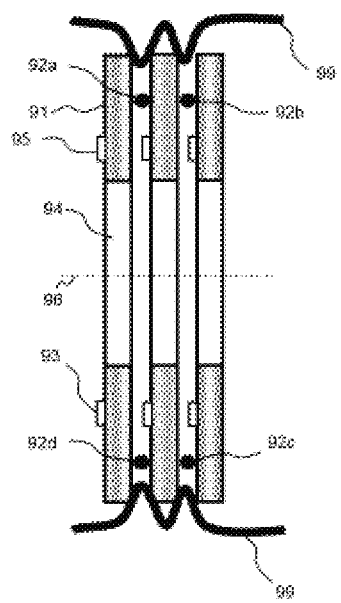

FIG. 9A, FIG. 9B, FIG. 9C, FIG. 9D, and FIG. 9E show cross section views of electrodes 91 of the flexible or re-configurable ion transfer device 20 connected to each other in accordance with one or more embodiments of the present disclosure. The electrodes 91 may be stacked on each other, as shown in FIG. 9A and may be centered around an axis 96, which may cross the centers of holes 94 on electrodes 91. In one or more embodiments, a plurality of spacers 92a-d may be placed in between the electrodes 91 to provide the required spacing between electrodes and also to provide the re-configurability and flexibility. In one or more embodiments, the spacers 92a-d may be spring connectors connected or permanently fixed (for example soldered on two ends or just one end) or temporarily contacted (for example by contacting one end of a spring connector to a pad on an adjacent electrode 91) to the two adjacent electrodes 91 that, in addition to providing the required spacing between electrodes, also provide electrical connection between the electrodes 91. The electrodes 91 may include one or more resistors 95 and one or more capacitors 93. The electrodes 91 each having an electrode axis 96a-c may be flexibly bend around the axis 96. In one or more embodiments, the degree of bending is defined as the angle between the axis 96 and each electrode axis 96a-c corresponding to the plurality of electrodes 91. The degree of bending may be any value between 0.0001 to 10 or more degrees for each electrode 91. In some embodiments, only some of the electrodes 91 may bend around the axis 96. In some embodiments, a heat-shrink tube 99 may keep the electrodes 91 in place (electrically separated from each other) while maintaining flexibility. In one or more embodiments, both the plurality of spacers 92a-d, and heat-shrink tube 99 may keep the electrodes 91 in place while providing flexibility. The heat-shrink tube, which may be one or more tubes added separately, may also serve as the enclosure 21 to maintain the electrodes 91 in reduced pressure as disclosed in the present application. Although FIG. 9C shows only one layer of heat-shrink tube 99, but one or more layers of heat-shrink tube 99 may be provided to adjust flexibility and the pressure inside the ion transfer device 20. In one embodiment, a plurality of wires, which may be disposed in between layers, outside, or inside the enclosure 21 (which may be for example the heat-shrink tube 99) provide required electrical radio frequency RF, or direct current (DC) voltages. The voltages may be provided in triangular, sawtooth, or pulsed waveforms (pulse and square waveforms may be used interchangeable in the present disclosure), with a period of, for example, 0.1, 0.5, 1, 5, 10, 100, or 1000 milliseconds or more or any value in between these numbers. The voltages may be periodic, having a period of 0.01, 0.1, 0.5, 1, or 2 seconds, or more than 2 seconds or any value in between. The max and minimum amplitude voltages may be −500V to 500V. In one or more embodiments, a plurality of heat-shrink tubes may be provided, and the electrical wires may be disposed in between the layers of the heat-shrink tube. In one or more embodiments, when heat-shrink tubing is being heated on the plurality of electrodes 91, vacuum is provided at the area where the plurality of electrodes 91 are located so that the heat-shrink tube 99 gets sucked in between two adjacent electrodes 91 to form a corrugated tube to allow flexibility via forming a corrugated tube form. In one or more embodiments, while heating the heat-shrink tube 99, air flow or cold air flow may be passed through the plurality of center holes 94 of the electrodes 91 to maintain the electrodes at a low temperature to prevent damage by the heat required, for example, melting of solder that may hold the resistors 95, capacitors 93, connectors 92a-d, or other parts of the ion transfer device 20.

Figure 9D:
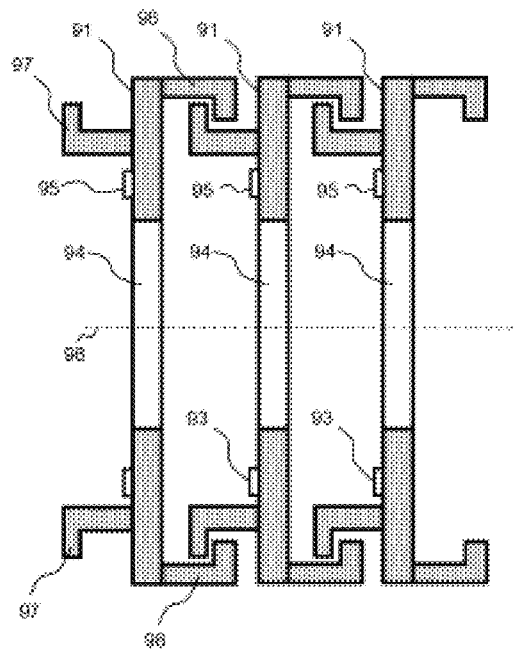
Figure 9E:
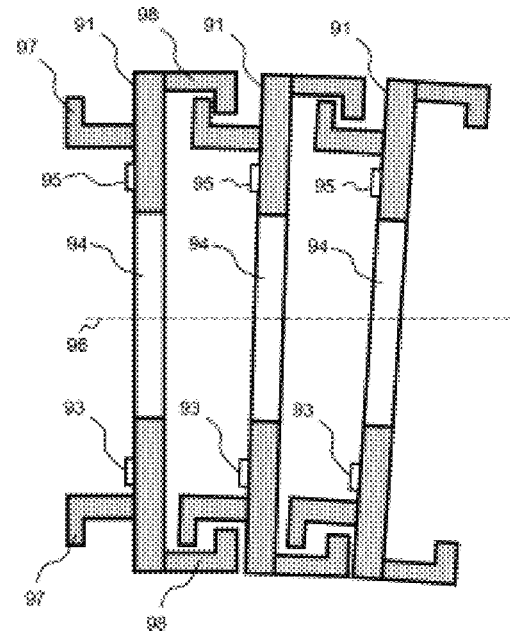
Figure 9F:
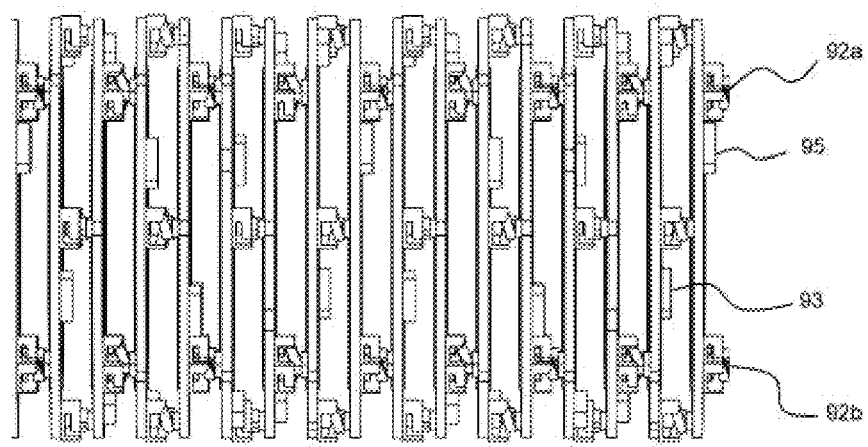
FIG. 9F, FIG. 9G, FIG. 9H, and FIG. 9I show views of the flexible or re-configurable ion transfer device in accordance with one or more embodiments of the present disclosure.
Figure 9G:
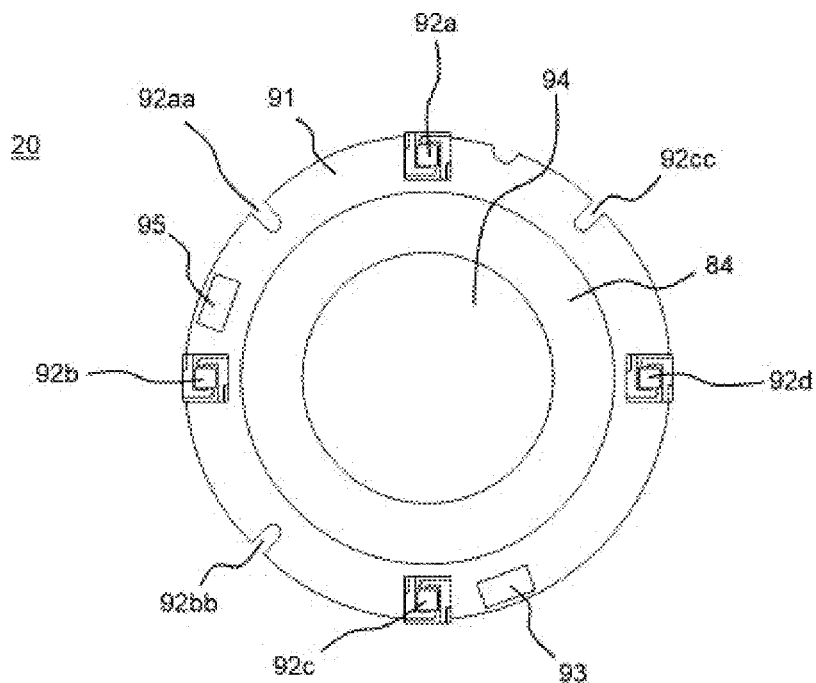
Figure 9H:
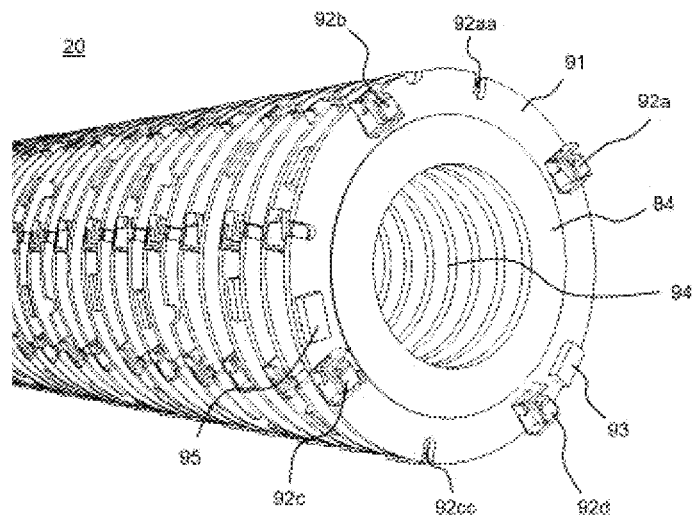

In one or more embodiment shown in FIG. 9D and FIG. 9E, instead of using the plurality of spacers 92a-d (as shown for example in FIG. 9A), the electrodes 91 may have matching extrusions 97, 98 on two sides of the electrode 91 that are engaged with corresponding matching extrusions 97, 98 of adjacent electrodes 91, as shown in FIG. 9D and FIG. 9E, to provide flexibility as disclosed in the present application. One of ordinary skill in the art would recognize that this structure may be manufactured by separate electrodes 91 flexibly connected to each other and having many degrees of freedom such as those found in "snake robots" having many degrees of freedom or may be manufactured by rolling a structure having matching extrusions 97, 98 similar to those used in conventional flexible electrical conduits.

Figure 9I:
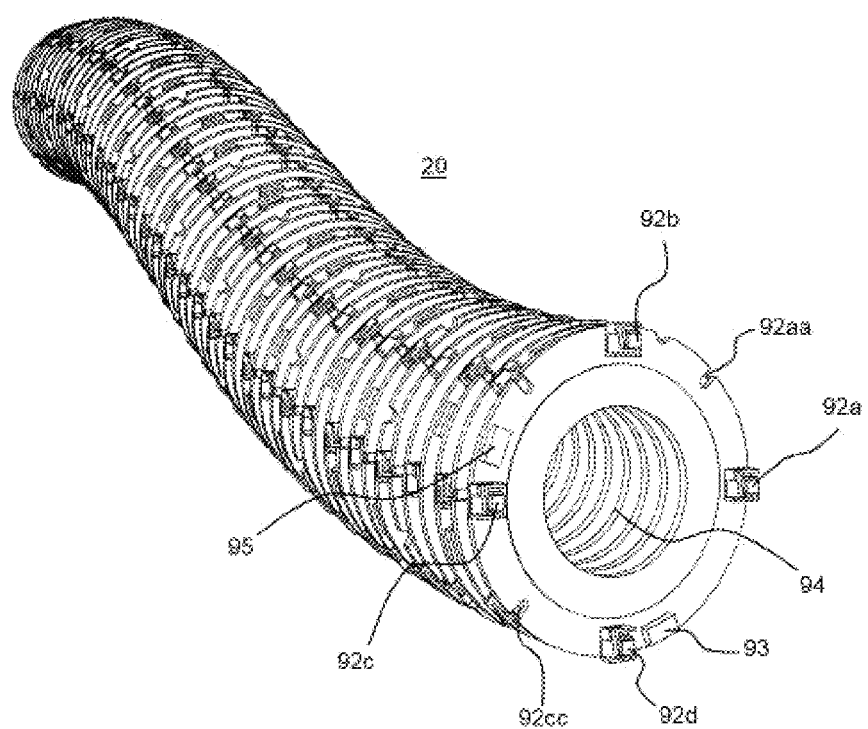
Figure 9J:
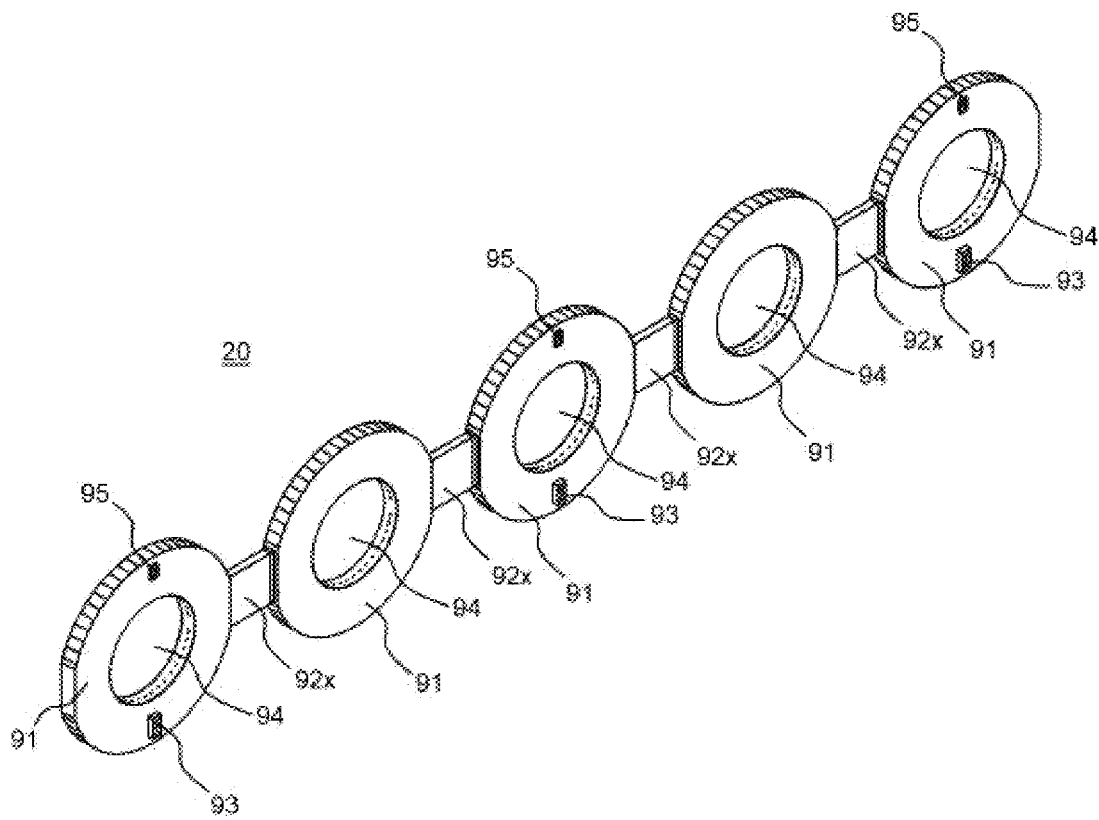
FIG. 9J, FIG. 9K, FIG. 9L, FIG. 9M, FIG. 9N, FIG. 9O, and FIG. 9P show views of electrodes of the flexible or re-configurable ion transfer device connected to each other via flexible PCB connection in accordance with one or more embodiments of the present disclosure.
Figure 9K:
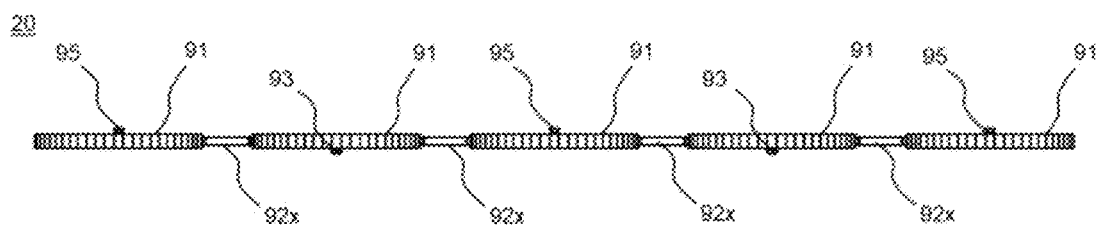
Figure 9L:
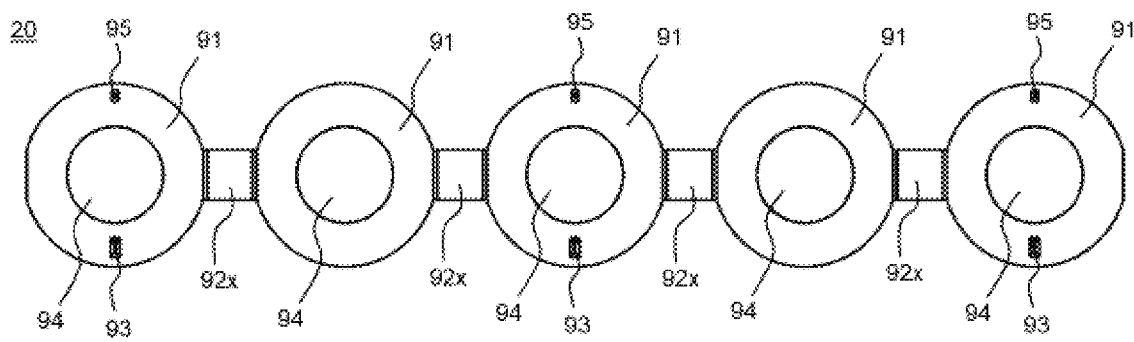
Figure 9M:
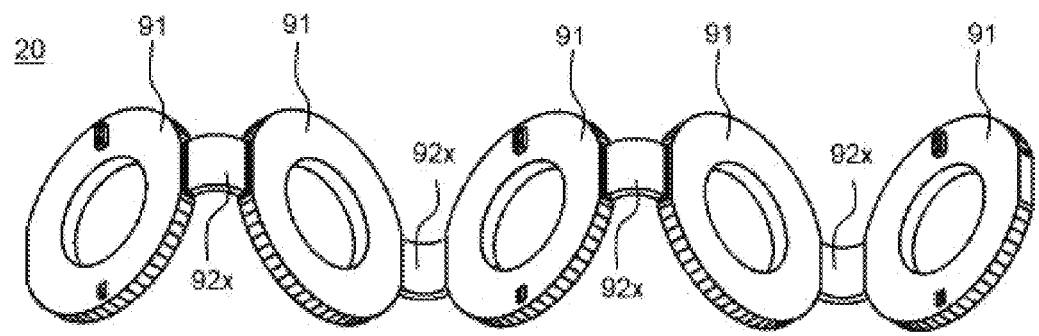
Figure 9N:
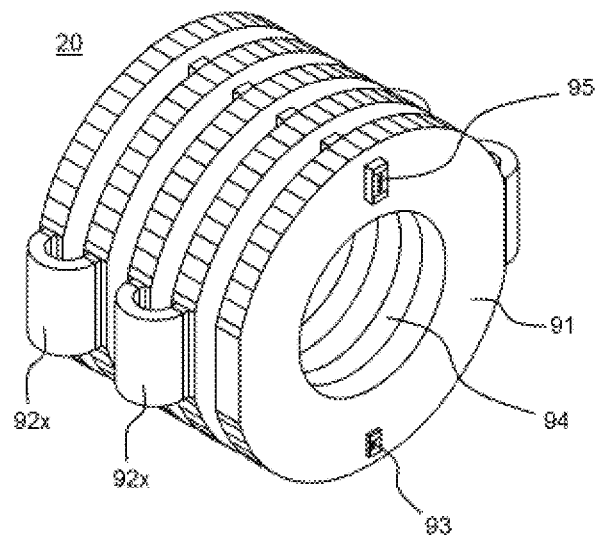
Figure 9O:
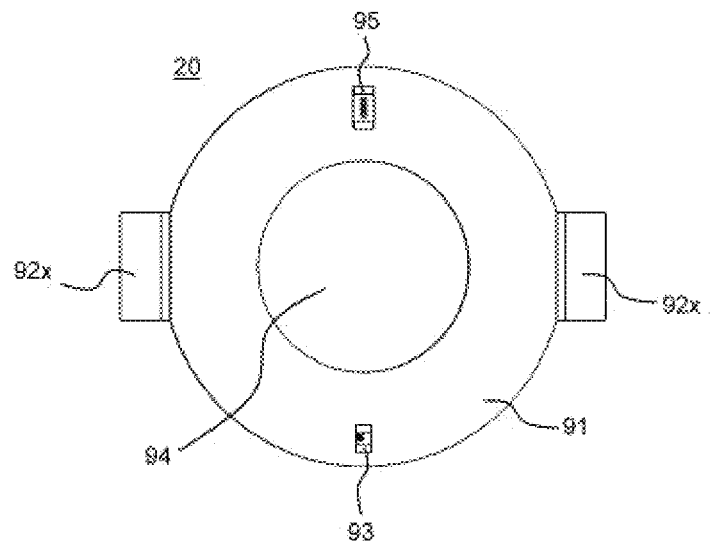

FIG. 9F, FIG. 9G, FIG. 9H, and FIG. 9I show views of electrodes 91 of the flexible or re-configurable ion transfer device 20 connected to each other in accordance with one or more embodiments of the present disclosure. These figures show exemplary embodiments of the flexible or re-configurable ion transfer device 20 that comprises a plurality of electrodes 91. In one exemplary embodiment, each of the electrodes 91 (constructed from PCB having a thickness of 0.2 mm to 2 mm or more) comprises a plurality of metal spring connectors 92a-d, a capacitor 93 and a resistor 95. The center hole 94 is provided by a metal-plated through hole 84. A plurality of plated half-through holes 92aa-cc (also known as plated half-holes or castellated hole in PCB manufacturing) are also provided on each of the electrodes 91. A top portion of the spring connectors 92a-d is aligned with the corresponding plated half-through holes 92aa-cc (the forth plated half-through holes is omitted but may exists in this figure) of the next board and are soldered to make the connection between the two adjacent electrodes 91. The electrodes may have the same electrical layout or may have different electrical layouts. In one or more embodiments, the electrical layout of the odd electrodes is the same and the electrical layout of the even electrodes is the same, but the electrical layout of the odd electrodes is different from the electrical layout of the even electrodes. The ion transfer device 20 may be constructed by stacking these two different electrode designs. As illustrated in FIG. 9I, the spring connectors 92a-d provide flexibility or re-configurability for the ion transfer device 20. The enclosure 99 is omitted in these figures for simplicity of the illustration.

Experimental results from this exemplary embodiment demonstrates that without application of the RF voltage at a pressure of 0.1 to 10 Torr (by only application of DC voltages as disclosed in the present application), almost no ions entering the ion inlet exit from ion outlet. Therefore, both RF voltages and DC voltages are required for operation of ion transfer device 20. The ions are created by electrospray ionization from myoglobin sample and enter the ion transfer device 20 after passing through a capillary inlet. By applying only one of the two out-of-phase RF voltages to the ion transfer device 20, only a portion of ions pass through the ion transfer device 20, yielding to an ion transfer efficiency of <80%. By application of both two out-of-phase RF voltages, the current reading on the ion outlet of the ion transfer device increases and the ion transfer efficiency reaches, for example, >80% up to nearly 100%. The experimental results demonstrated no change in ion current for a 1" bend radius and at 90 degrees bend angle.

Figure 9P:
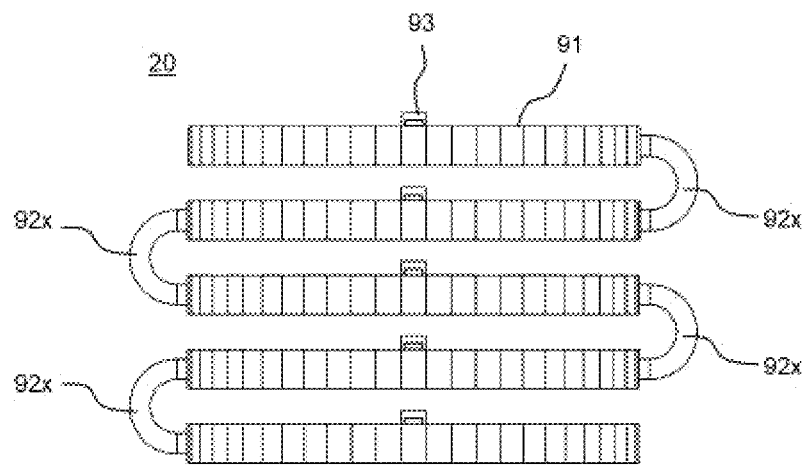

FIG. 9J, FIG. 9K, FIG. 9L, FIG. 9M, FIG. 9N, FIG. 9O, and FIG. 9P show views of electrodes 91 of the flexible or re-configurable ion transfer device 20 connected to each other via flexible PCB connection 92x in accordance with one or more embodiments of the present disclosure. These figures also include the metal-plated through hole 84 on each of the electrodes but they are omitted for simplicity of the illustrations. In this exemplary embodiment, the ion transfer device 20 is manufactured by manufacturing the plurality of electrodes 91 as well as the electrical connections via flexible PCB connections 92x between adjacent electrodes 91 with a process known as flex-rigid manufacturing in which one or more flexible layers (for example polyimide-copper) are sandwiched between two rigid layers (for example FR4-copper). Upon fabrication of the flex-rigid PCB, the electrodes 91 are folded around the flexible PCB connections 92x in order to construct the ion transfer device 20. The ion transfer device having five electrodes (for simplicity of illustration) is shown in FIG. 9P. The electrodes 91 may include a plurality of spacers 92a-d or a plurality of enclosures 99 in from of heat-shrink tubing (not shown in this figure) similar to the embodiment shown in FIG. 9C. The electrical connections for supplying RF and DC voltages to the ion transfer device 20 shown in FIG. 9P may be supplied from the top and/or the bottom electrode 91 (or the first and last electrodes of the electrode units 31a-j as defined in the present disclosure) on the two ends of the ion transfer tube 20 or the electrode units 31a-j. In one or more embodiments, the ion transfer device 20 shown in FIG. 9P may be defined as the electrode units 31a-d disclosed in the present application.

Figure 9Q:
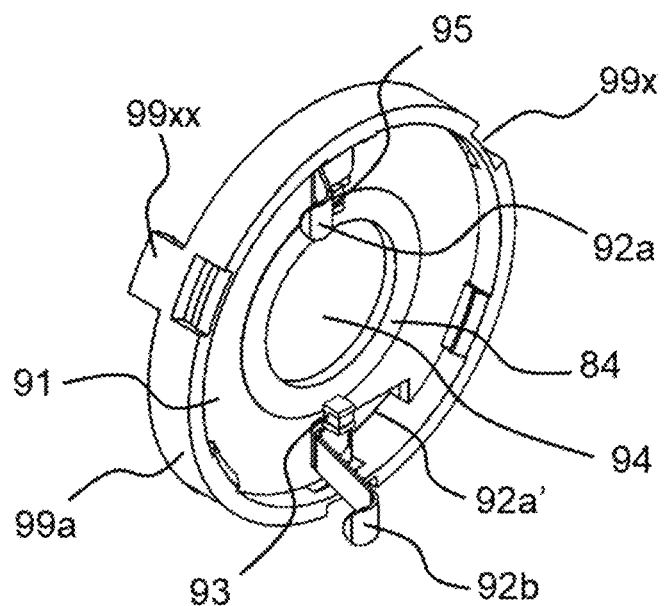
Figure 9T:
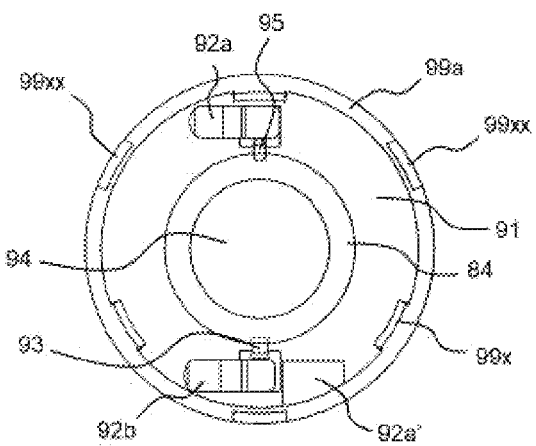
FIG. 9T, FIG. 9U, FIG. 9V show views of the flexible or re-configurable ion transfer device connected to each other in accordance with one or more embodiments of the present disclosure.
Figure 9T:
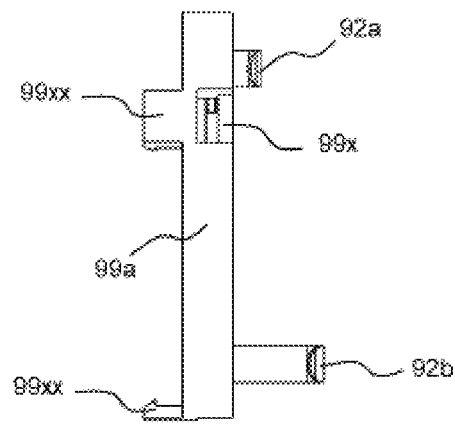
Figure 9T:
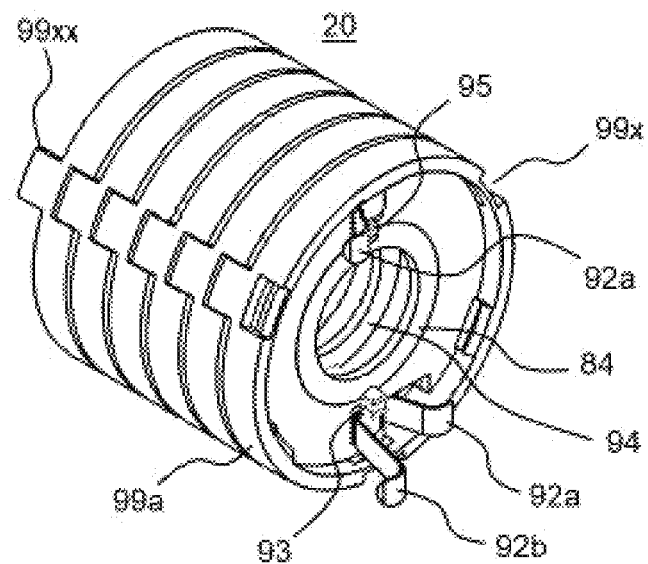
Figure 9U:
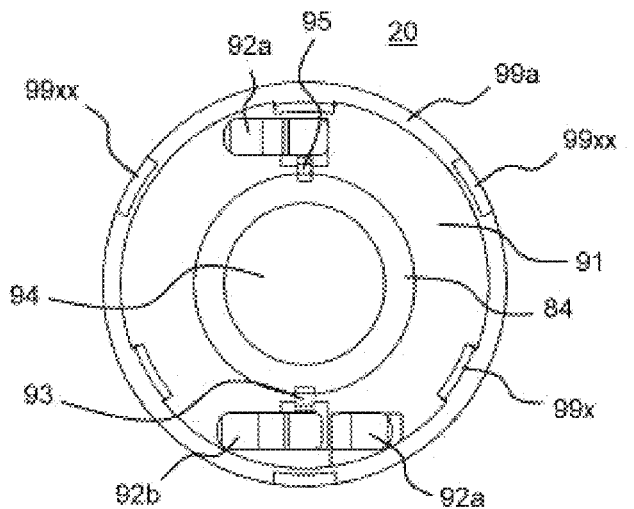
Figure 9V:
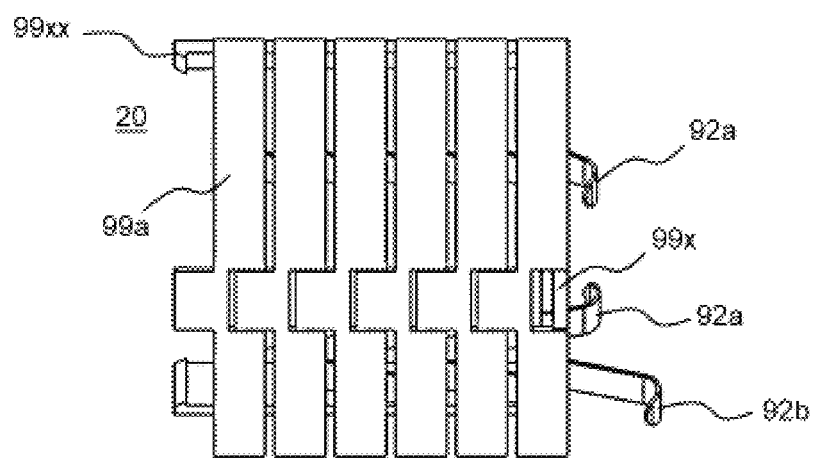
Figure 9W:
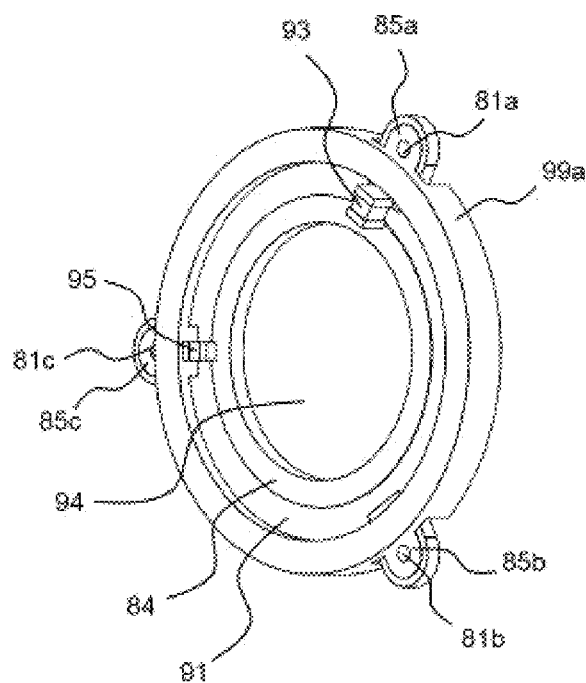
FIG. 9W, FIG. 9X, FIG. 9Y, and FIG. 9Z show views of an electrode of the flexible or re-configurable ion transfer device connected to each other in accordance with one or more embodiments of the present disclosure.
Figure 9X:
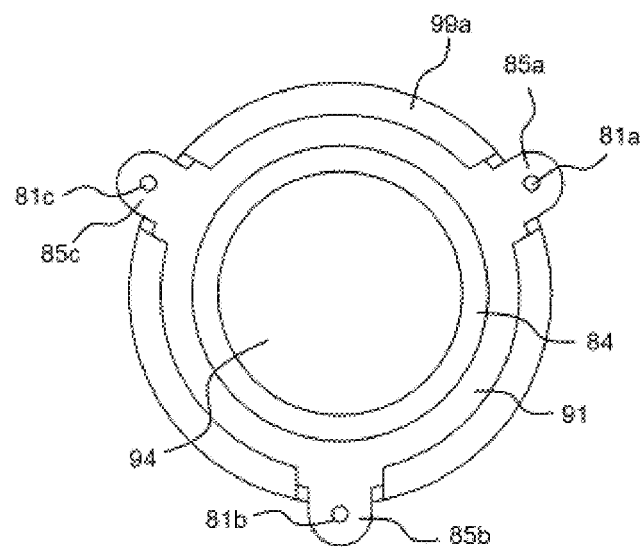
Figure 9Y:
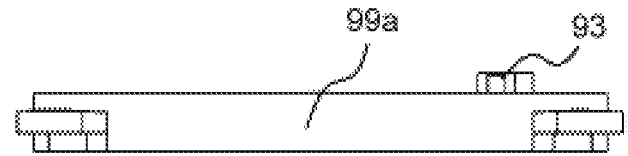

FIG. 9Q, FIG. 9R, and FIG. 9S show views of an electrode 91 of the flexible or re-configurable ion transfer device 20 connected to each other in accordance with one or more embodiments of the present disclosure. FIG. 9T, FIG. 9U, FIG. 9V show views of the flexible or re-configurable ion transfer device 20 connected to each other in accordance with one or more embodiments of the present disclosure. In this exemplary embodiment, each of the electrodes 91 includes two spring connectors 92a-b one of which is shorter for connection to an adjacent electrodes 91 and one them 92b is longer for connection to the electrode 91 that is located as the next electrode to the adjacent electrode 91 through an opening 92a' of in the adjacent electrode without making connections to the adjacent electrode. In one embodiment, the electrode is placed in a housing 99a. The housing may have a plurality of pins 99xx and a plurality of pin receptors 99x for snap-in connection. In one or more embodiments, an enclosure may be used in form of heat-shrink tubing to enclosure the structures shown in these figures including the housing 99a.

FIG. 9W, FIG. 9X, FIG. 9Y, and FIG. 9Z show views of an electrode 91 of the flexible or re-configurable ion transfer device 20 connected to each other in accordance with one or more embodiments of the present disclosure. In this exemplary embodiment, each electrode 91 is placed in a housing 99a such that a plurality of tabs 85a-c are extrude from the housing 99a for making the required electrical connections as disclosed in the present application. A plurality of holes 81a-c are provided on the tabs 85a-c that may be used to hold the electrodes 91 of the ion transfer device 20 together, for example, using an elastic string or similar methods disclosed as wires or rods 61a-d in relation to FIGS. 6C and 6D for example. The rods 61a-d are omitted in FIG. 9Z for simplicity of illustration. In one or more embodiments, the wires or rods 61a-d may be wires that also make electrical connection to different electrodes 91. For example, the holes 81a-c on the two electrodes may be connected to each other by a short wire In one or more embodiments, the electrodes 91 made of PCB in the ion transfer device 20 may be rotated with respect to each other, for example, 10, 20, 45, 90 degrees. The electrodes may have the same electrical layout or may have different electrical layouts. In one or more embodiments, the electrical layout of the odd electrodes is the same and the electrical layout of the even electrodes is the same, but the electrical layout of the odd electrodes is different from the electrical layout of the even electrodes.

Figure 10A:
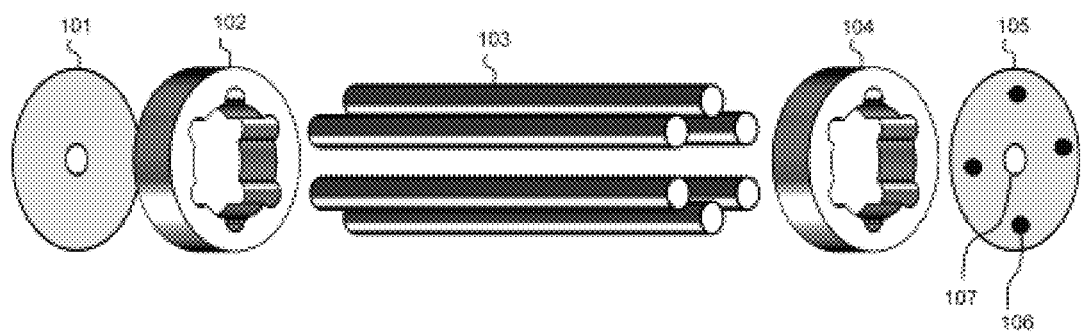
FIG. 10A and FIG. 10B show perspective views of electrode structure of flexible or re-configurable ion transfer device in accordance with one or more embodiments of the present disclosure.
Figure 10B:
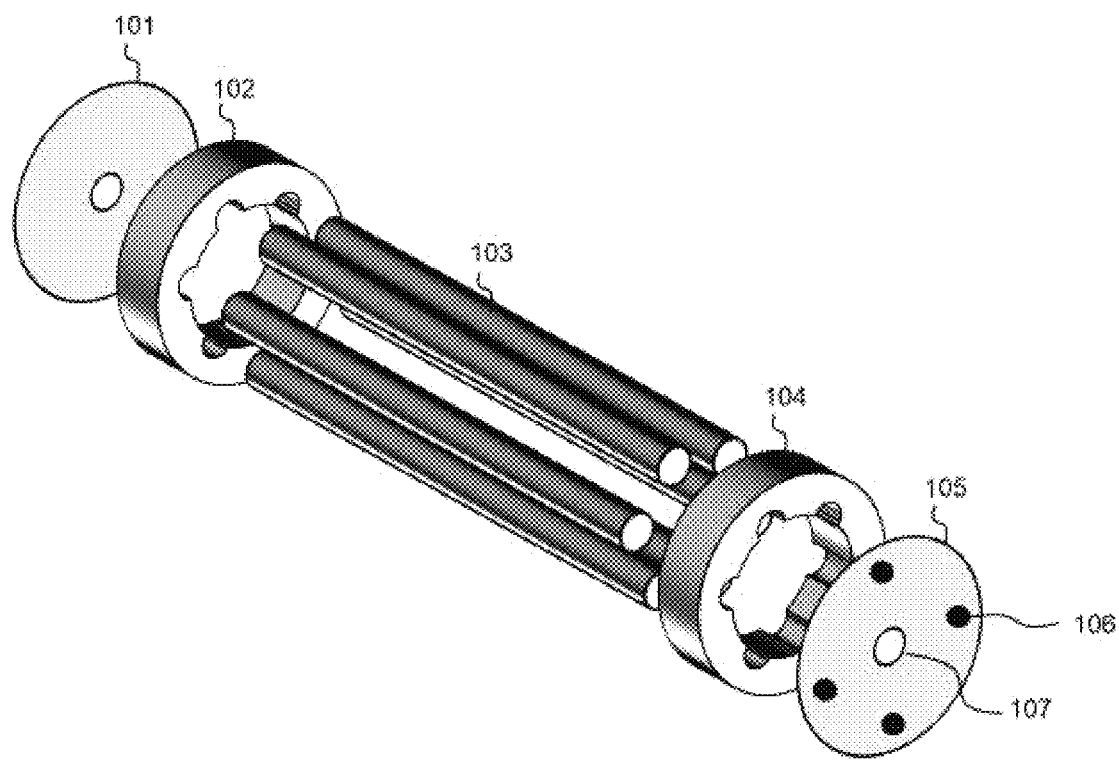

FIG. 10A and FIG. 10B show perspective views of individual electrodes of the flexible or re-configurable ion transfer device 20 in accordance with one or more embodiments of the present disclosure. For simplicity of illustration, the enclosure 21 is not shown in these figures. FIG. 10A and FIG. 10B show a multipole ion guide that includes a plurality of rods 103 connected to DC and/or RF voltages. Multiple ion guides may have any even number of rods, such as four, six, eight, etc. that are hold in place with a plurality of rod holders 102, 104, and may have flat electrodes similar to those illustrated in FIGS. 14C and 15B. Two conductance limiting plates 101, 105 (may be made of PCB) having an orifice 107 (may be in form of a plated through hole) may be attached at the two ends to the rod holders 102, 104. The conductance limiting plates 101, 105 may be connected to DC or RF voltages (for example at a frequency of 0.1 MHz to 10 MHz). A plurality of electrically insulating or conducting pieces 106 (which may be made by elastic materials such as Viton or conductive metal spring connectors) may be connected to the conductance limiting orifices 107 to provide flexibility or to provide the electrical connection between two adjacent electrode units. The odd and even numbers of the plurality of rods 103 are respectively connected to two out-of-phase RF voltages. A DC offset voltage may be added to the RF voltages by coupling capacitors.

Figure 11A:
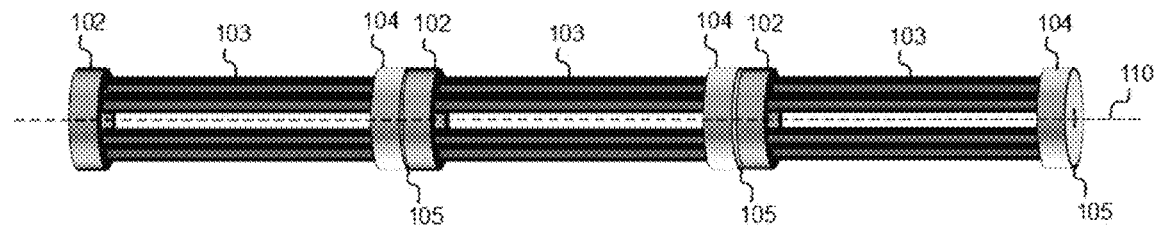
FIG. 11A, FIG. 11B, and FIG. 11C show perspective views of flexible or re-configurable ion transfer device including three electrode structures connected to each other in accordance with one or more embodiments of the present disclosure.
Figure 11B:
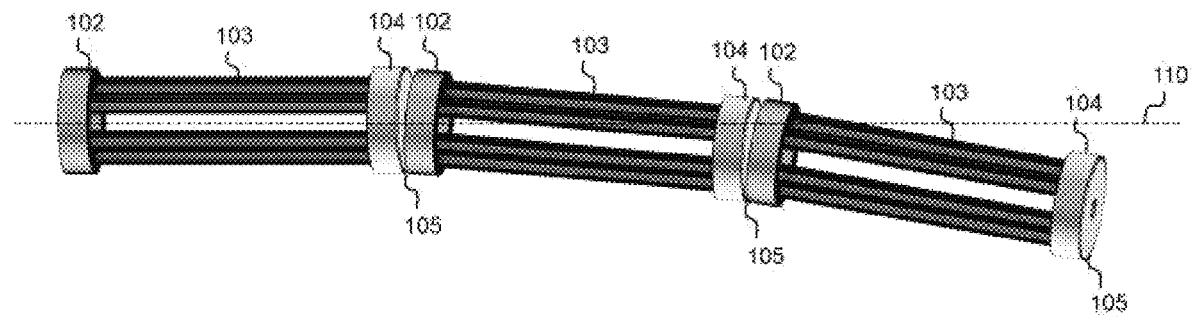
Figure 11C:
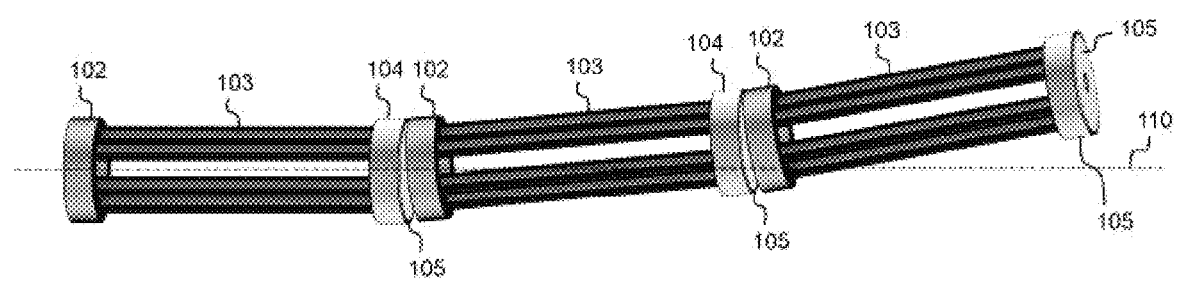

FIG. 11A, FIG. 11B, and FIG. 11C show perspective views of three electrodes of the flexible or re-configurable ion transfer device 20 connected to each other in accordance with one or more embodiments of the present disclosure. In one embodiment, the ion transfer device 20 may be constructed with multipole ion guides (each acting as one electrode unit) flexibly attached to each other. A plurality of individual electrode units (each electrode including the components as shown in FIG. 10A and FIG. 10B) may be connected to each other as shown in FIG. 11A, FIG. 11B, and FIG. 11C to provide a flexible ion transfer device 20. The two conductance limiting plates 105 on two adjacent electrodes are connected to each other with the plurality of the electrically insulating or conductive pieces 106 placed in between to provide flexibility. In one or more embodiment, the two electrodes or multipole ion guide structures may be connected to each other with the structure shown in FIG. 9A and FIG. 9B to provide flexibility. Heat-shrink tubes may also be used as the enclosure 21 and are not shown for simplicity of illustration.

Figure 12A:
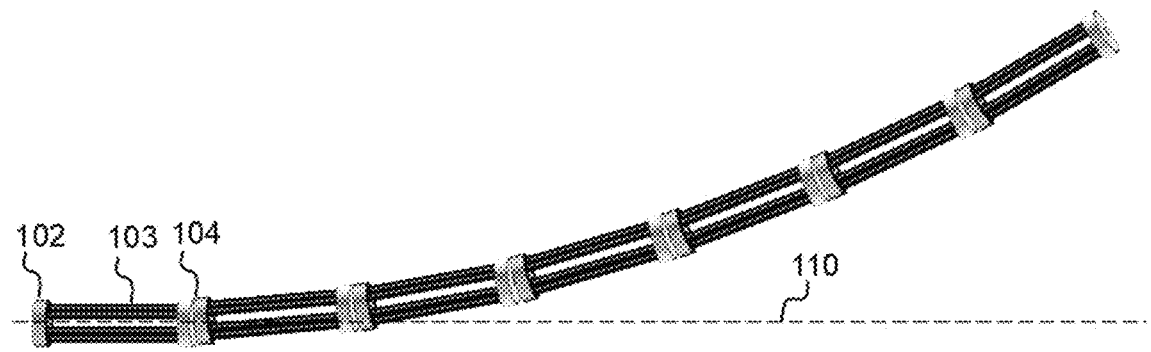
FIG. 12A and FIG. 12B show perspective views of flexible or re-configurable ion transfer device including seven electrode structures connected to each other in accordance with one or more embodiments of the present disclosure.
Figure 12B:
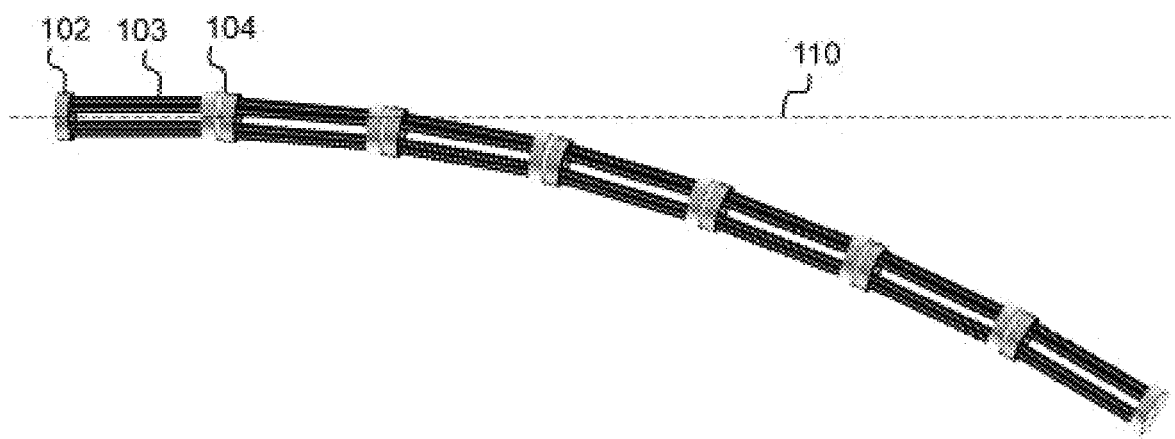

FIG. 12A and FIG. 12B show perspective views of seven electrodes of the flexible or re-configurable ion transfer device 20 connected to each other in accordance with one or more embodiments of the present disclosure. In one embodiment, the electrodes may have a plurality of curvatures or bends around an axis 110 of the ion transfer device 20. The enclosure is not shown in this figure for simplicity of illustration. The flexibility of this structure may be similar to those shown in FIG. 7A and FIG. 7B and the assembly illustrated in these figures may be bold together by one or more heat-shrink tubes.

Figure 13:
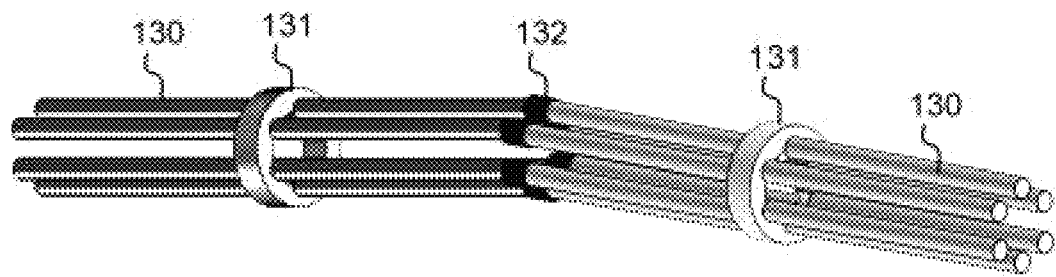
FIG. 13 shows a perspective view of flexible or re-configurable ion transfer device including two electrode structures connected to each other accordance with one or more embodiments of the present disclosure.

FIG. 13 shows a perspective view of two electrodes of the flexible or re-configurable ion transfer device 20 connected to each other in accordance with one or more embodiments of the present disclosure. In one embodiment, the multipole ion guides may include a plurality of rods 130 that are hold in place with a rod holder 131. To provide flexibility, the rods 130 of the two adjacent electrodes are connected flexibly to each other as shown in FIG. 13 with a plurality of connecting pieces 132. The plurality of conducting pieces connect two corresponding rods 130 to each other. The plurality of connecting pieces 132 may be conductive or electrically insulating, which may be made by, for example, connecting the rods with flexible epoxy. In one or more embodiment, the plurality of rods 130 may be flexible while maintaining a constant or semi-constant distance between two adjacent rods in an electrode assembly to provide a flexible ion transfer device 20.

Figure 14A:
FIG. 14A, FIG. 14B, and FIG. 14C show perspective views of enclosure and electrode geometries of flexible or re-configurable ion transfer device in accordance with one or more embodiments of the present disclosure.
Figure 14B:
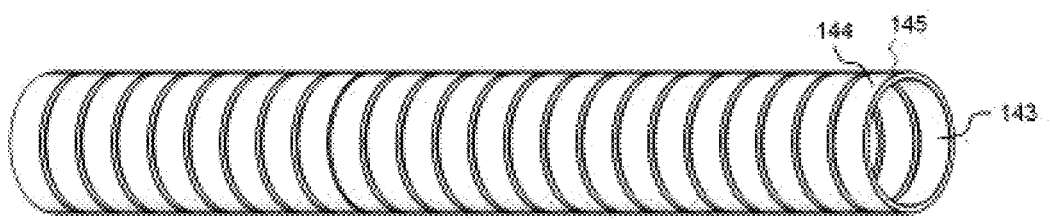
Figure 14C:
Figure 15A:
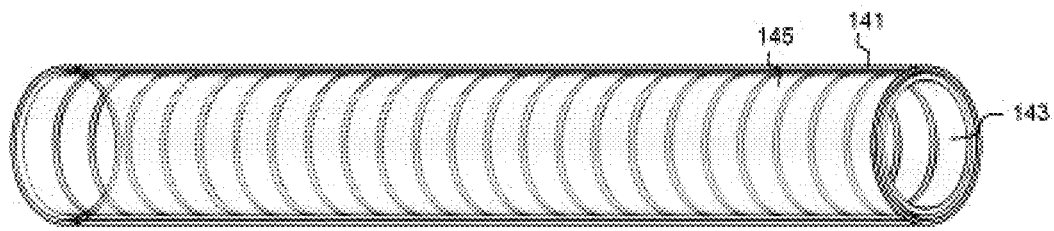
FIG. 15A, FIG. 15B, and FIG. 15C show perspective views of flexible or re-configurable ion transfer devices in accordance with one or more embodiments of the present disclosure.
Figure 15B:
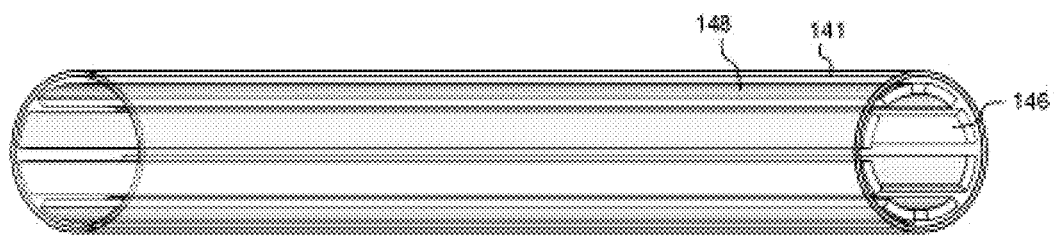
Figure 15C:
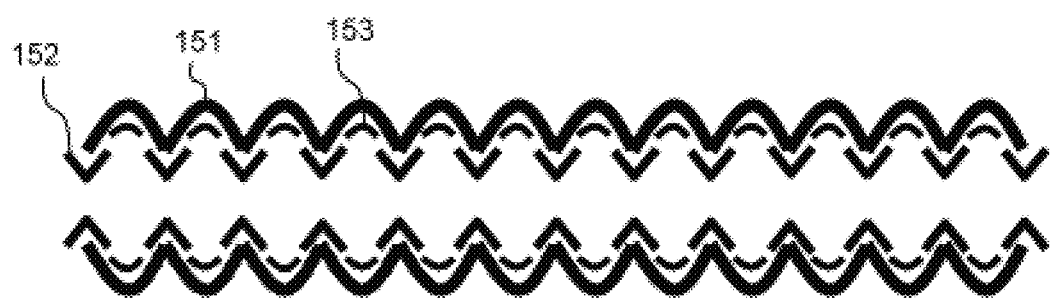

FIG. 14A, FIG. 14B, and FIG. 14C show perspective views of an enclosure and two different electrode geometries of the flexible or re-configurable ion transfer device 20 in accordance with one or more embodiments of the present disclosure. FIG. 15A, FIG. 15B, and FIG. 15C show perspective views of three embodiments of the flexible or re-configurable ion transfer device 20 in accordance with one or more embodiments of the present disclosure. In one embodiment, the enclosure may be made of a flexible tube 141 having an inner surface 142 as shown in FIG. 14A. A plurality of ring electrodes 145, as shown in FIG. 14B, are connected to a plurality of DC and RF voltages (not shown for simplicity of illustration) may be disposed inside the flexible tube 141 to provide the ion transfer device 20. Each of the plurality of ring electrodes 145 may include an inner surface 143 and an outer surface 144. The outer surface 144 may be disposed on the inner surface 142 of the flexible tube 141 to provide an ion transfer device 20 as shown in FIG. 15A. In one or more embodiments, a plurality of elongated electrodes 148 (any even number of electrodes) having an outer surface 147 and an inner surface 146 may be disposed in the flexible tube 141. FIG. 15B shows an example of the ion transfer device 20 according to this exemplary embodiment. The ring electrodes 145 and the elongated electrodes 148 are flexible and may bend when the flexible 141 tube bends. The flexible tube 141 may be made with a heat-shrink tube that has a sticky inner surface 142 for sticking to the outer surface 144 of the ring electrodes 145 or the outer surface 147 of the plurality of elongated electrodes 148 to the inner surface 142 of the flexible tube 141. FIG. 15C show a cross section of one or more embodiments of a flexible ion transfer device 20 which may be made with bellow tube 151 and a plurality of electrodes 152 may be place inside the bellow tube 151. In this embodiment, a plurality of ground electrodes 153 prevent ions from charged build-up on the bellow tube 151. Although these embodiments are shown in straight form, one of ordinary skill in the art, in view of the present disclosure, would understand and appreciate that these structures provide flexibility and may be bent to any form or shape similar to a conventional hose.

Figure 16:
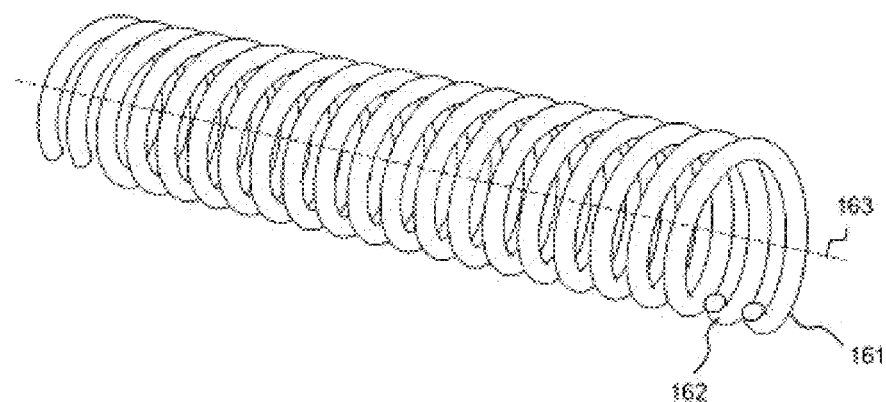
FIG. 16 shows a perspective view of electrode geometry of flexible or re-configurable ion transfer device in accordance with one or more embodiments of the present disclosure.

FIG. 16 shows a perspective view of electrode geometry in an embodiment of the flexible or re-configurable ion transfer device 20 in accordance with one or more embodiments of the present disclosure. The flexible ion transfer tube 20 may be constructed with two wires 161, 162 (or a plurality of the two wires 161, 162) that are wound around an axis 163 into helix structures having a diameter with any value in the range of 0.2 to 6 inches. The two wires are connected to RF voltages at a frequency of 0.05 to 10 MHz and amplitudes of, for example, 50V. The amplitude may be any value between 1 to 1000V. The enclosure is not shown in FIG. 16 for simplicity of illustration but similar flexible tubes, or heat-shrink tubes disclosed earlier in the present application may be used. The ion transfer device 20 made with the electrodes shown in FIG. 16 is flexible and may have several curvatures along the length of the ion transfer device 20. As noted above, the pressure of the ion transfer tube may be in the range of, for example, 0.001 to 760 Torr.

Figure 17A:
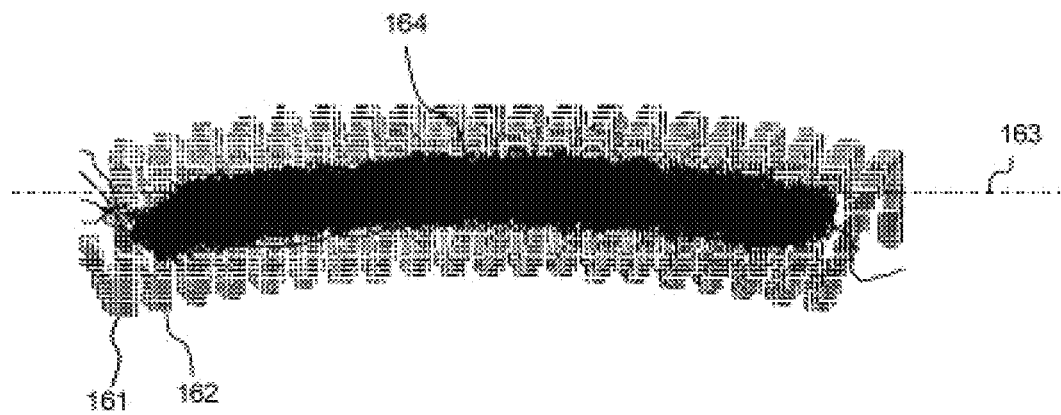
FIG. 17A and FIG. 17B show two side views of ion trajectory simulation in flexible or re-configurable ion transfer device in accordance with one or more embodiments of the present disclosure.
Figure 17B:
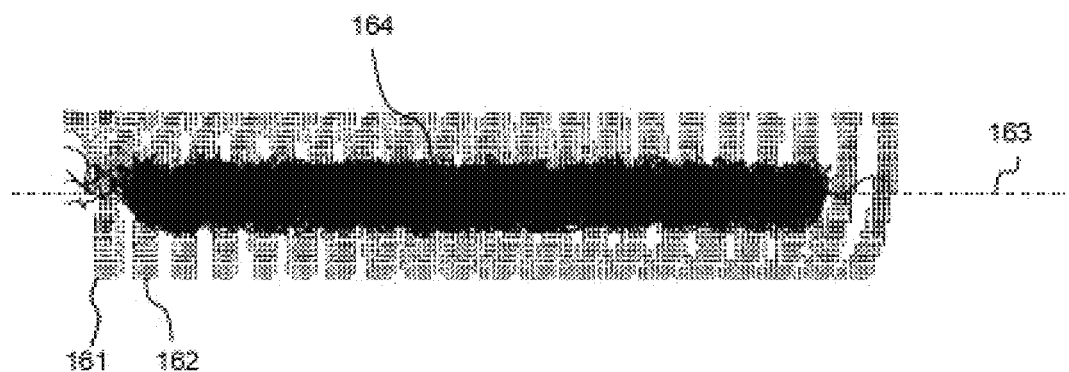

FIG. 17A and FIG. 17B show two side views of ion trajectory simulation in an embodiment of the flexible or re-configurable ion transfer device 20 in accordance with one or more embodiments of the present disclosure. Ion trajectory simulations were performed with SIMION® software and the results are shown in FIG. 17A (side view) and FIG. 17B (top view). The simulations were performed in a pressure of 1 Torr and the simulation results demonstrated that the electrodes effectively trap the ions, producing an ion cloud 164, for a long period of time. The simulations were performed in a bent structure of FIG. 16 around an axis 163. No DC voltages are applied and only RF voltages are used in the simulations. A variety of RF voltages were applied at different frequencies and voltages and the structure was functional in a wide range of parameters (voltage and amplitude of the RF voltage) and pressures (0.01 to 30 Torr).

Figure 18:
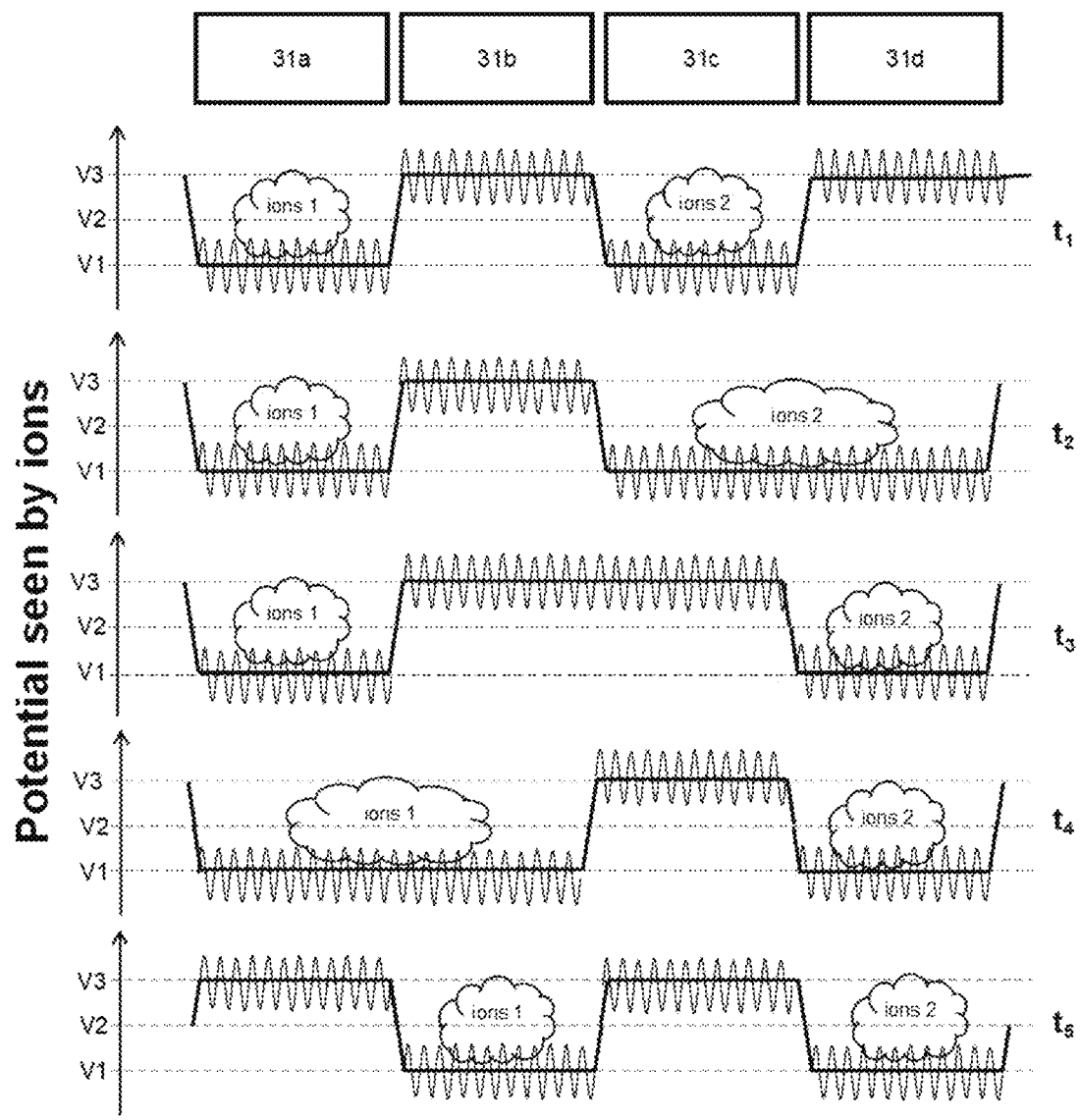
FIG. 18 shows RF and DC voltage waveforms for flexible or re-configurable ion transfer device in accordance with one or more embodiments of the present disclosure.

FIG. 18 shows RF and DC voltage waveforms applied to the electrodes of the flexible or re-configurable ion transfer device 20 in accordance with one or more embodiments of the present disclosure. In the five sequential graphs shown in FIG. 18, the times are shown by t1 to t5, t1 graph being the first waveform of the sequence and t5 being the last waveform of the sequence. The time period between each graph may be the same or different. For example, the time difference between t1 and t2 may be in the order of milliseconds (ms) or seconds (s), and may be any value between 0.01 ms to 10 s.

The electrode units 31a-d may comprise any electrode configuration, geometry, shape, or form, or a combination of them disclosed in the present application. The plurality of electrode units 31a-d may be those disclosed in FIG. 6A or FIG. 9A-Z, in which even and odd electrode are connected to two out-of-phase RF voltages (having 180 or ~180 phase shift) respectively. Two out-of-phase RF voltages are applied to two adjacent electrodes. For example, in a multipole ion guide, one of the two out-of-phase RF voltages is applied to every other electrode and the other of the two out-of-phase RF voltages is applied to the remaining electrodes. RF voltages of the ion transfer device 20 pushes the ions radially toward the centerline or an axis of the ion transfer device 20 as disclosed and shown above in exemplary embodiments, and as for example shown in the simulation results of FIG. 17A and FIG. 17B, which is an RF only simulation. The radial force is provided via an effective potential from RF voltages or waveforms on the electrodes. The RF waveforms effectively keep ions off the plates. The DC voltages push ions axially toward the two ends of the ion transfer device 20. The applied RF voltages trap ions around an axis and inside the ion transfer device 20.

In FIG. 18, DC voltages are illustrated with solid lines and the RF voltages are illustrated with a sine or zigzag waveform. Although the DC and RF voltages are illustrated separately for simplicity of illustration, one of ordinary skill in the art would understand that these two waveforms may be combined, superimposed, or added by application of the RF voltages via a capacitor to the DC voltages. The DC voltage sources providing the DC voltages may require RF chokes to prevent the RF voltage from penetrating into the DC power supply. The DC voltages may also be regarded as the DC offset voltage applied to the RF voltage. The RF voltage (two out-of-phase sin waveform applied for radially pushing the ions towards a center of the ion transfer device 20) may always be present in the electrodes of the ion transfer device 20. Alternatively, the RF voltage may only be present when ions exist in the related electrodes of the ion transfer device 20.

The term "electrode unit" in the present application is defined as a number of electrodes that contain an ion packet, for example ion 1 or ion 2 as shown in FIG. 18. Each of the electrode units 31a-d is an electrode unit that may contain any number of electrodes but trap and contain an ion packet as described earlier in the present application.

In t1, two packet of ions, ions 1 and ions 2, trapped by the RF voltages, are held in DC potential wells created in electrode units 31a and 31c at V1 voltage, meaning they are not able to travel forward in the ion transfer device 20. The ions 1 and ions 2 may be from the same ionization source or from different ionization sources. Also, the ions 1 and ions 2 may contain the same or different types of ions obtained from the same or different samples by the ionization source. The DC voltage at electrode unit 31b and 31d are at V3, which is greater than V1. Therefore, the DC voltages of the electrode units 31b and 31d act as a potential barrier and prevent the two ions packets (which may be in the form of ion clouds or ion population) from mixing with each other. The values of DC voltages may be any positive value in a range from 0.1V to 1000V for positive ions. For negative ions, the voltages are negative voltages in the same range.

In t2, the DC voltage of the electrode unit 31d is reduced from V3 to V1, thus allowing the ions 2 to axially expand to the adjacent electrode unit 31d (the ions are still radially contained with the RF voltages—in fact, the ions 1 and ions 2 are always contained in the centerline by RF voltages as described above). The potential well of the electrode 31b prevents the ions 1 and ions 2 from mixing with each other.

In t3, the DC voltage on electrode unit 31c is increased from V1 to V3 thus forcing or pushing the ions 2 into the electrode unit 31d. Therefore, the ions 2 are shifted one electrode unit to the right.

In t4, the DC voltage of the electrode unit 31b is reduced from V3 to V1, thus allowing the ions 1 to axially expand to 31b electrodes. The potential well of the electrode 31c prevents the ions 1 and ions 2 from mixing with each other.

In t5, the DC voltage on electrode unit 31a is increased from V1 to V3 thus pushing the ions 1 into the electrode 31b. Therefore, the ions 1 are also shifted one electrode unit to the right (where the ion outlet of the ion transfer device 20 is located in this exemplary embodiment).

During the sequences from t1 to t5, two separate ion packets, ions 1 and ions 2 are shifted one electrode unit from the ion inlet side of the ion transfer device 20 (on the left) to the ion outlet side of the ion transfer device 20 (on the right). Therefore, this sequence enables sequentially packing and efficiently transferring the ions or ion clouds via the flexible ion transfer device 20 without these ion packets being mixed. The ion transfer may be performed in a sequential manner and the ions, in the form of ion packets, may be transferred from the inlet to the outlet of the ion transfer device 20 sequentially. Further, this sequence also allows arrangement of ions produced from different ionization sources or produced from the same ionization source but from different sample or produced during scanning/imaging mass spectrometry into ion packets. Although in each time frame of t1 to t5 of FIG. 18 the DC voltage values V1 and V3 are used but each electrode 31a-d may have a different voltage value and they do not need to be necessarily the same.

Figure 19:
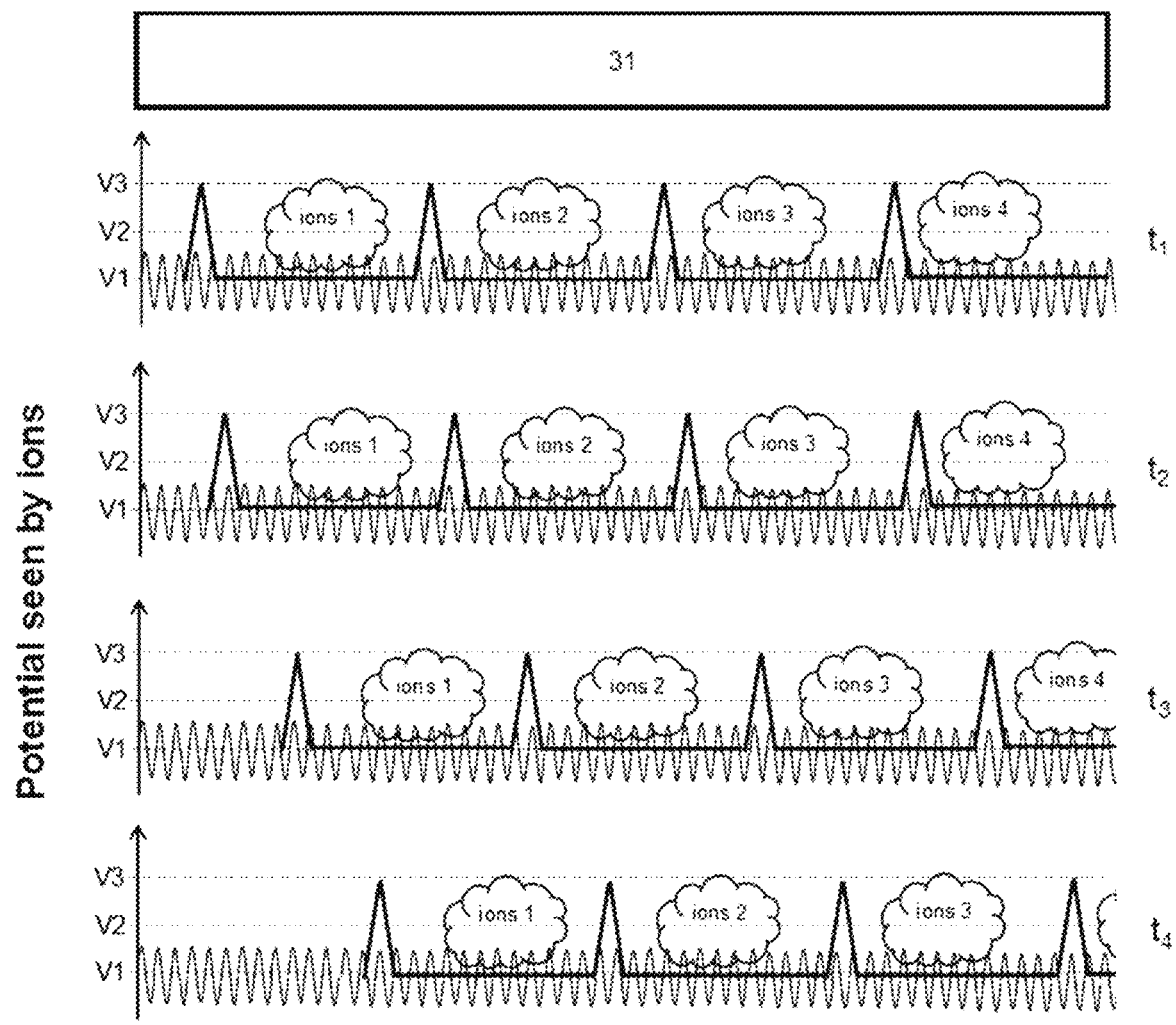
FIG. 19 shows RF and DC voltage waveforms for flexible or re-configurable ion transfer device in accordance with one or more embodiments of the present disclosure.

FIG. 19 shows RF and DC voltage waveforms applied to the electrode unit 31 of the flexible or re-configurable ion transfer device 20 in accordance with one or more embodiments of the present disclosure. The RF and DC voltages are described in detail with respect to FIG. 18, and the same description is applicable to FIG. 19. The electrode 31 may comprise of a plurality of ring electrodes similar to those shown in FIG. 6A, FIG. 6B, FIG. 6C or FIG. 9A-Z. In exemplary embodiment shown in FIG. 19, DC voltages are individually controlled and applied to each electrode of the electrode unit 31. In the following, the applications and shifting of ion packets are disclosed for the electrode unit 31 with ring electrodes similar to those shown in FIG. 6A but one of ordinary skill in the art would understand and appreciate that the shifting of ion packets may also be realized with other electrode geometries of the ion transfer device 20 as disclosed in the present application. Further, one of ordinary skill in the art would understand and appreciate such waveform may enable ion mobility separation of the ions when ions move along the ion transfer device.

In this exemplary embodiment, each electrode unit is one electrode, for example one ring electrode (shown in FIG.

6A) is one electrode unit, and the shifting of the ion packets are performed in one electrode unit at each time period (t1 to t5).

In t1, four packet of ions, ions 1, ions 2, ions 3, and ions 4 (in the form of ion packets), are trapped separately by DC potential wells created in electrode unit 31 created by application of V3 to four of the ring electrodes which are spatially separate (first group of ring electrodes of the electrode unit 31). In FIG. 19 and at t1, first group of ring electrodes are held at DC voltage V3 and the remaining electrodes are at held at V1.

In t2, the ring electrodes adjacent and to the right of the first group of ring electrodes (second group of electrodes) are switched to V3 from V1, and shortly after, the first group of electrodes are switched to V1.

In t3, the ring electrodes adjacent and to the right of the second group of ring electrodes (third group of electrodes) are switched to V3 from V1, and shortly after, the second group of electrodes are switched to V1.

In t4, the ring electrodes adjacent and to the right of the third group of ring electrodes (fourth group of electrodes) are switched to V3 from V1, and shortly after (for example tens of microseconds to milliseconds or seconds), the second group of electrodes are switched to V1.

As a result, the ion packets move sequentially in the ion transfer device 20 from left (the ion inlet) to the right (the ion outlet) while keeping the ion packets separate, for example by a traveling DC voltage pulse while the RF voltages maintain the ions around an axis of the ion transfer device 20.

The waveform of FIG. 19 is similar to the waveform of FIG. 18 with the difference that each electrode is individually connected to addressable DC voltages in FIG. 19. In FIG. 18, a group of electrodes are connected to the same DC voltage. Therefore, sequential transfer of ions according to FIG. 18 may require smaller number of individually addressable DC voltages compared to that described in FIG. 19, as in the embodiment of FIG. 19, all individual electrodes must be individually connected to controllable DC voltages.

The sequential transfer of ion packets in the ion transfer device enables introduction of calibration ion packets to a mass spectrometer. For example, the Ions 2 in FIG. 19, may be ions produced from a calibration sample with labeled or unlabeled molecules that is introduced into the ion packets as used for calibration. In one embodiment, the Ion 2 may a separator have distinct ions that is not found in a sample under test.

Figure 20:
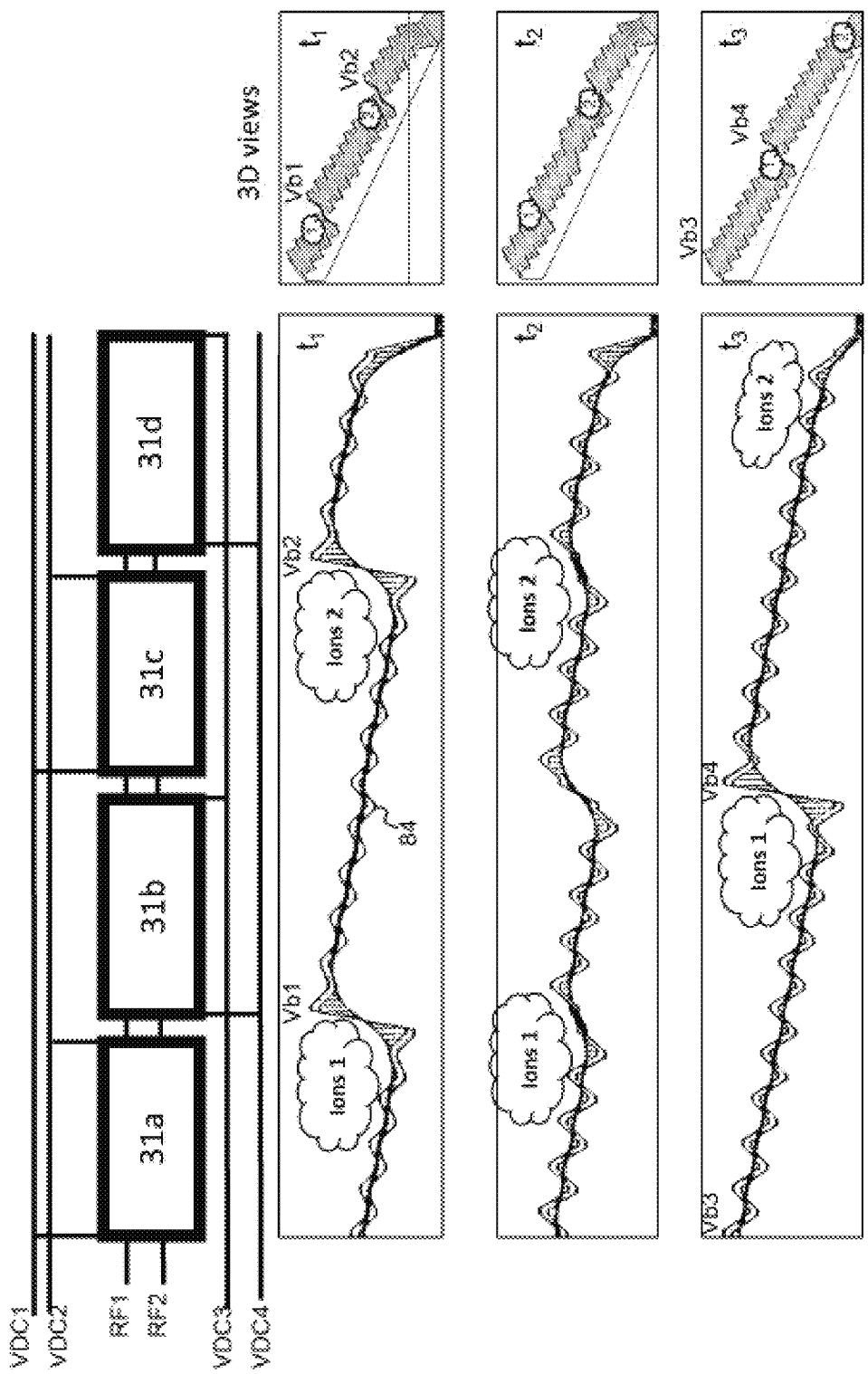
FIG. 20 shows RF and DC voltage waveforms applied to the electrodes of the flexible or re-configurable ion transfer device 20 in accordance with one or more embodiments of the present disclosure.

FIG. 20 shows RF and DC voltage waveforms applied to the electrodes of the flexible or re-configurable ion transfer device in accordance with one or more embodiments of the present disclosure. In the three sequential side-view and 3D views shown in FIG. 18 produced by SIMION® software, the times are shown by t1 to t3, t1 graph being the first waveform of the sequence and t3 being the last waveform of the sequence. The time period between each graph (t2–t1 or t3–t1) may be the same or different. For example, the time difference between t1 and t2 may be in the order of milliseconds (ms) or seconds (s), and may be any value between 0.01 ms to 10 s.

Figure 9Z:
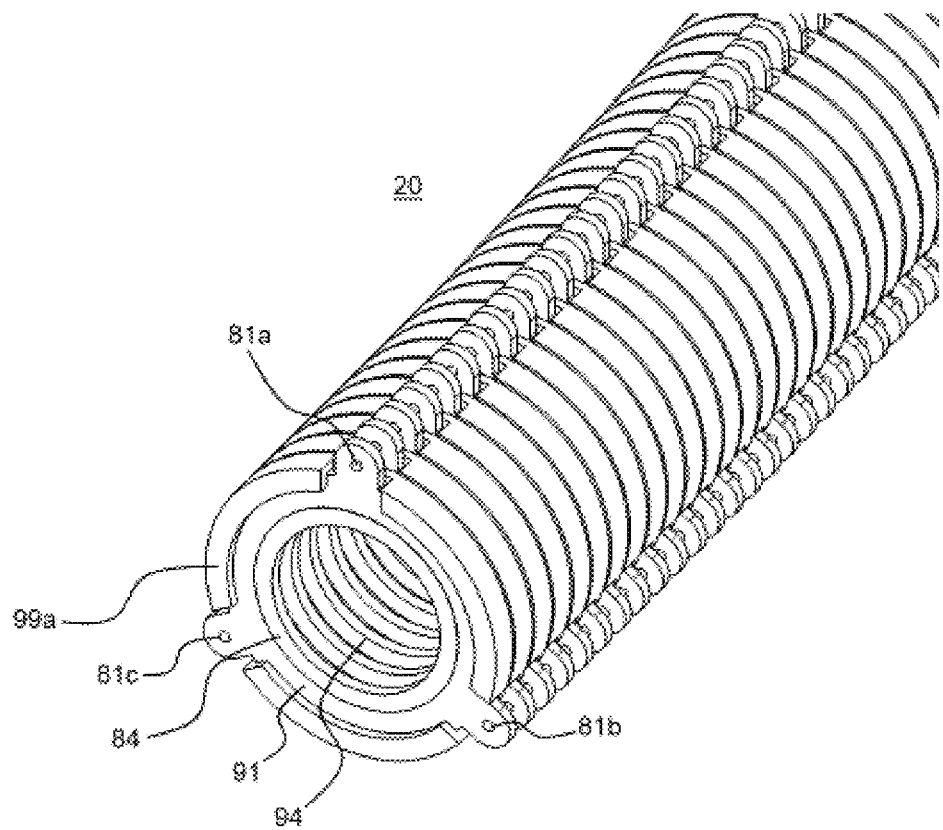

The electrode units 31a-d may comprise any electrode configuration, geometry, shape, or form, or a combination of them disclosed in the present application, for example, the embodiments shown in FIGS. 9A-Z. The plurality of electrode units 31a-d may be those disclosed in FIG. 6A-B or FIG. 9A-Z, in which even and odd electrode are connected to two out-of-phase RF voltages (having 180 or ~180 degrees phase shift) respectively. Two out-of-phase RF voltages (illustrated as RF1 and RF2 also disclosed as VRF1 and VRF2) are applied to two adjacent electrodes 84. RF voltages of the ion transfer device 20 pushes or forces the ions, or causes the ions to diffuse radially toward the centerline or an axis of the ion transfer device 20 as disclosed and shown above in exemplary embodiments, and as for example, shown in the simulation results of FIG. 17A and FIG. 17B, which is an RF only simulation. DC voltages may be added to the RF voltages on each of the electrodes 91 or each electrode unit 31a-d, for example, by means of capacitor coupling the RF voltages to the DC voltages.

Figure 21:
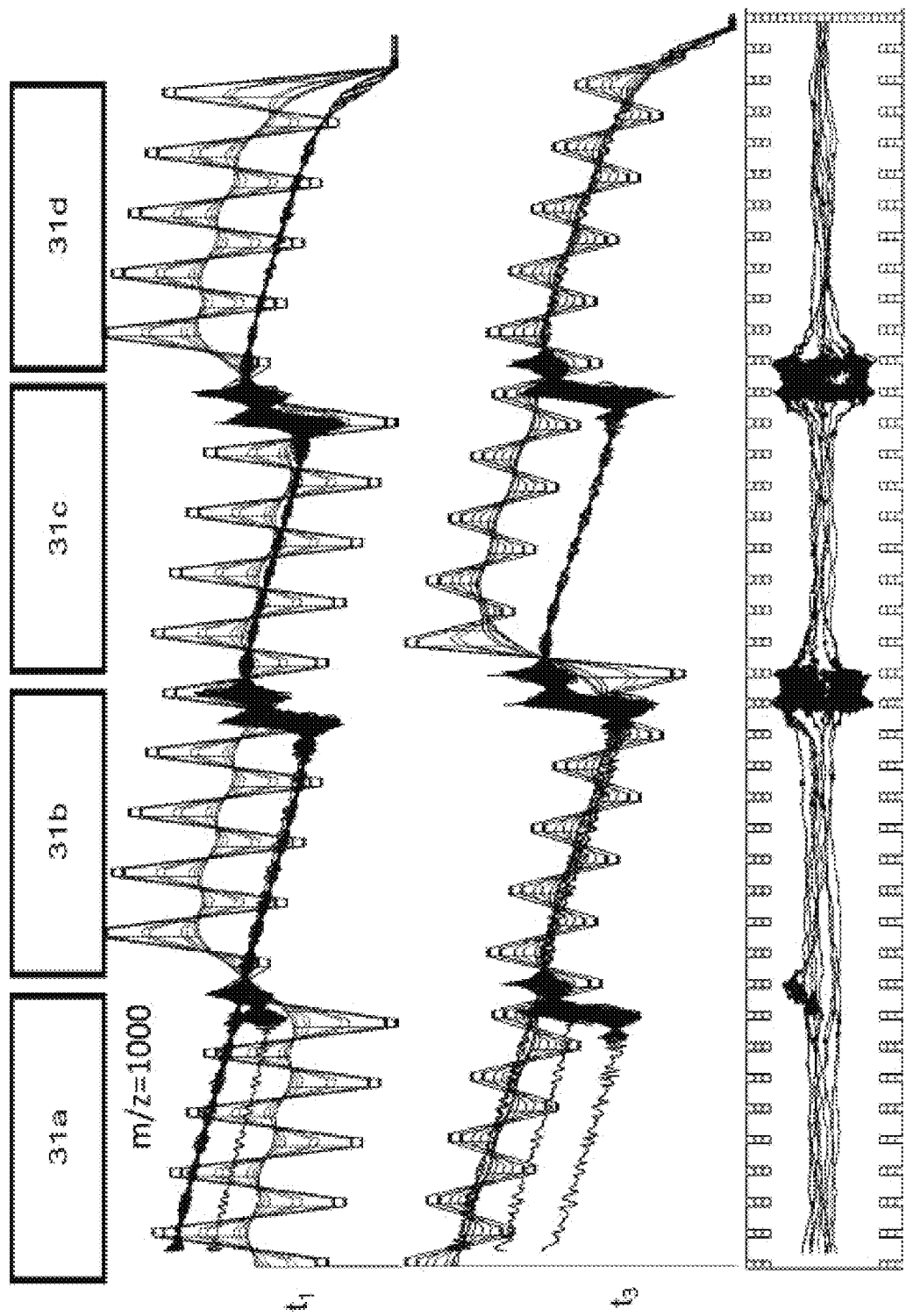
FIG. 21 shows RF and DC voltage waveforms applied to the electrodes of the flexible or re-configurable ion transfer device along with simulation results of ion trajectories in accordance with one or more embodiments of the present disclosure.
Figure 23:
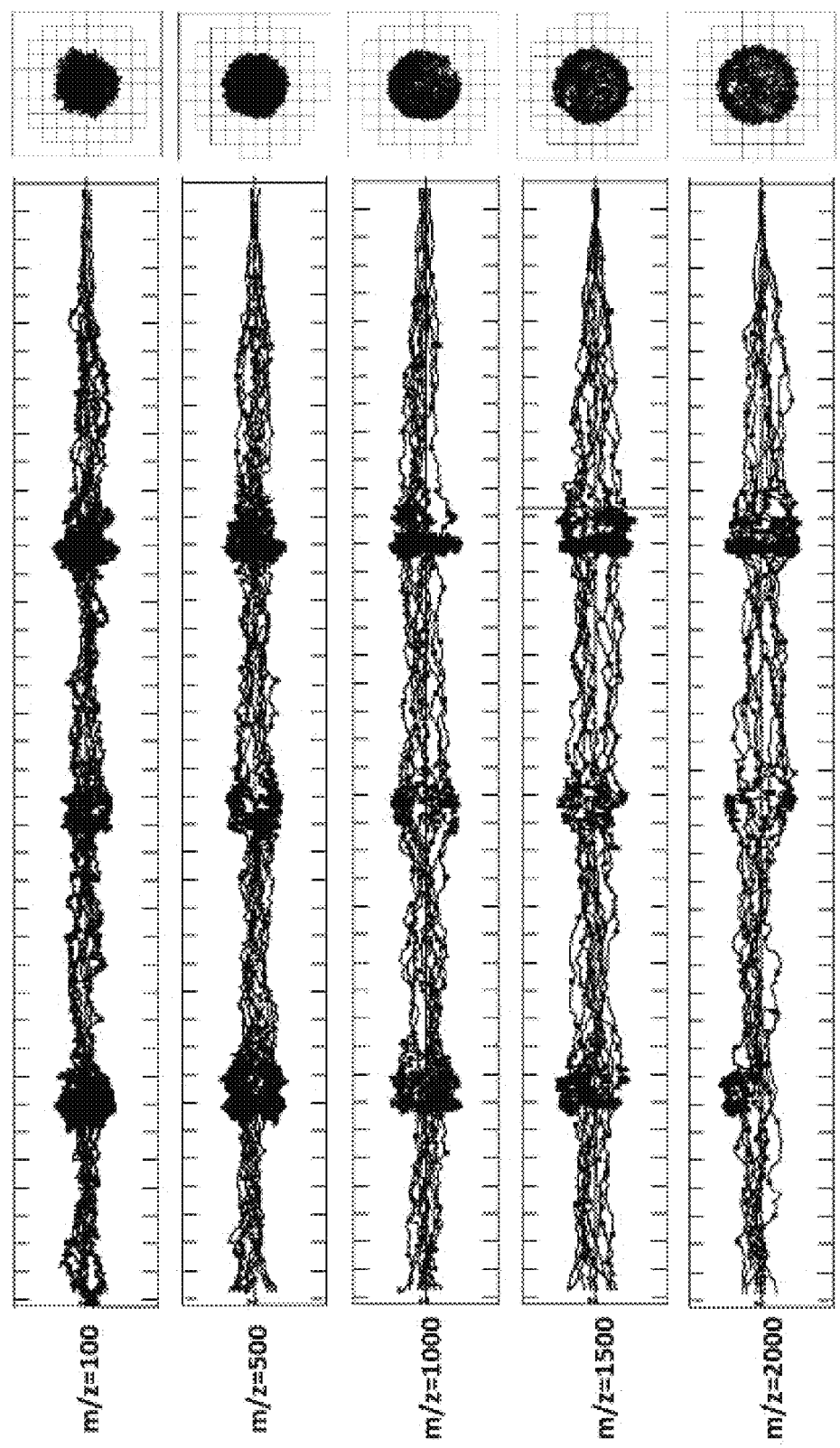
FIG. 23 shows side view and front view of simulation results of trajectory for ions having with m/z of 100, 500, 1500, and 2000 in accordance with one or more embodiments of the present disclosure.

In one or more embodiments, for some mass to charge (m/z) ratios, the ions may form a donut or torus shape around the central axis (for example, as illustrated in FIG. 21 and FIG. 23 at m/z of 1000, 1500 and 2000) or a hollow cylinder or hollow cylindrical shape (not shown). The radial force is provided via an effective potential from RF voltages or waveforms on the electrodes. The RF waveforms effectively keep ions off the plates by creating an effective potential (also called pseudo-potential) that radially confines ions inside the ion transfer device 20. The DC voltages push ions axially toward the two ends of the ion transfer device 20. The applied RF voltages maintain or trap ions around an axis and inside the ion transfer device 20.

In FIG. 20, each electrode unit 31a-d has ten electrodes 91. DC voltages, VDC1, VDC2, VDC3, and VDC4, which are shown in FIG. 20 connected via wires to electrode units 31a-d, create sawtooth voltage gradient along electrode units 31a-d with negative ramp. The negative ramp is defined by VDC1, VDC2, VDC3, and VDC4 and a length of each electrode unit 31a-d. The VDC1 and VDC2 (creating a first voltage slope in each of the electrode units 31a and 31c) are applied to the first and last electrodes 91 of the electrode units 31a and 31c; and the VDC3 and VDC4 (creating a second voltage slope in each of the electrode units 31b and 31d) are applied to the first and last electrodes 91 of the electrode units 31b and 31d, respectively. The DC voltages for electrodes 91 (or 84) in between the first and last electrodes 91 of the electrode units 31a-d are provided with the resistor network disclosed in the present application. The VDC1 and VDC2 are simultaneously moved up and down via a first time-varying offset voltage, for example, that has a triangle, square, or pulse form, and the VDC3 and VDC4 are simultaneously moved up and down via a second time-varying offset voltage, for example, that has a triangle, square or pulse form too. That is, the VDC1=VDC1constant +VDC1time-varying, such that the VDC1 constant is the component that is not time dependent (remains constant) and the VDC1time-varyingis the component that is time dependent (it goes up and down in a triangle, square, or pulse wave form). The same applies to VDC2-4. If ion transfer device includes only one electrode unit, then VDC1time-varying may be zero.

The first and the second time-varying offset voltages may be triangle form or square form or pulse form having a frequency of 0.01 to 100 KHz or higher. This frequency and the VDC1, VDC2, VDC3, and VDC4 may be adjusted to allow enough time and/or provide a predetermined voltage gradient slope along each electrode unit 31a-j to empty an electrode unit 31a-d from an ion packet ("Ions 1" or "Ions 2" for example) but prevent the ion packet from passing the next or adjacent electrode unit. The first and the second time-varying offset voltages may be applied such than when the VDC1 and VDC2 is moving up the VDC3 and VDC4 move down; and when the VDC1 and VDC2 is moving down the VDC3 and VDC4 move up. The first and the second time-varying offset voltages may have the same waveform or wave-shape but with a phase shift or difference, for example, 180-degree phase shift or difference. In one or more embodiments, VDC3 and VDC4 may be produced by adding two extra resistors, for example adjustable resistors, connected to ground, therefore, only using two VDC1 and VDC4 is sufficient for the ion transfer device 20. The extra resistor may be adjusted to tune voltages that appears at the electrodes connected to VDC3 and VDC4.

In one or more embodiments, the value of VDC2 that is connected to the exit electrode 91 of the electrode unit 31a and 31c is greater or equal or close to the value of VDC4 that is connected to the entrance electrode 91 of 31b and 31d when the first time-varying offset voltage (time-varying offset voltage of VDC1 and VDC2) is at maximum and the second time-varying offset voltage (time-varying offset voltage of VDC3 and VDC4) is at minimum. This reduces the potential barrier to be less than zero or zero or nearly zero to allow the ions to travel from one electrode unit to the next electrode unit (for example as shown in t3 of FIG. 20). Similarly, the value of VDC3 that is connected to the exit electrode 91 of the electrode unit 31b and 31d is greater or equal or close to the value of VDC1 that is connected to the entrance electrode 91 of 31a and 31c when the first time-varying offset voltage is at minimum and the second time-varying offset voltage is at maximum. This reduces the potential barrier to be less than zero or zero or nearly zero to allow the ions to pass through the voltage barrier and travel from one electrode unit to the next electrode unit. (shown in t1 of FIG. 20). Application of voltages as disclosed above causes the ions entering the ion transfer device 20 to form ion packets 1 (Ions 1) and packet 2 (Ions 2) that move as shown in FIG. 20. That is, in t1, the ions entering the ion transfer device 20 are trapped in electrode unit 31a (shown as "Ions 1" in FIG. 20) because the voltage potential barrier (Vb1) produced by the first electrode 91 of the electrode unit 31b prevents ions (Ions 1) from moving forward to the next electrode unit 31b. Also, the first slope of electrode unit 31a, maintains or traps the ions (Ion 1 or illustrated as "1" in 3D views in FIG. 20) via RF voltages at the end of electrode unit 31a next to the exit electrode 91 of the electrode unit 31a. Similarly, in t1, "Ions 2" (illustrated as "2" in 3D views in FIG. 20) in the ion transfer device 20 are trapped, via RF voltages, in electrode unit 31c because the voltage potential barrier (Vb2) produced by the first electrode 91 in the electrode unit 31d prevents ions from moving forward. Also, the first slope of electrode unit 31c maintains the ions (Ion 2) at the end of electrode unit 31c at a proximity of the exit electrode 91 of the electrode unit 31c.

In t2, the first time-varying offset voltage causes the potentials in electrode units 31a,c to increase (either abruptly or gradually within a predetermined time period of 0.01 to 10 s) while the second time-varying offset voltage causes the potentials in electrode units 31b,d to decrease (either abruptly or gradually within a predetermined time period of 0.01 to 10 s synchronized with the first time-varying offset voltage), thus reducing the potential barriers Vb1 and Vb2 so that "Ions 1" and "Ions 2" may move forward to electrode unit 31b and 31d, respectively.

In t3, the first time-varying offset voltage reaches or creates potential barrier Vb3 in electrode unit 31a and reaches or creates the potential barrier Vb4 in electrode unit 31c, and therefore, cause the potentials in the entrance electrode of the electrode units 31a,c to reach the maximum values of potential barriers Vb3 and Vb4 (Vb3 and Vb4 may be the same or different). Similarly, the second time-varying offset voltage causes the potentials in electrode units 31b and 31d to decrease, thus allowing the "Ions 1" and "Ions 2" to move forward to electrode unit 31b and 31d, respectively.

Through this algorithm or method of controlling the VDC1, VDC2, VDC3, and VDC4, the ions may enter and sequentially packed and transferred in the ion transfer device 20. Although FIG. 20 shows that the voltages "VDC1 and VDC2" and "VDC3 and VDC4" are applied to 31a,c and 31b, d, but these voltages may be independently controlled for each of the electrode units 31a-d. A length of each electrode unit 31a-d may be equal or different. The number of electrodes 91 in each electrode unit 31a-d may be the same or different and may be 1 to 10, 10 to 100, 100 to 1000, or more. The maximum and minimum voltages of VDC1, VDC2, VDC3, and VDC4 are positive for positive ions and negative for negative ions. Absolute value of VDC1, VDC2, VDC3, and VDC4 may be any value above zero potential, for example, 1V to 100V, or 100 to 500V. The absolute value of the first and second slope may be any value in the range of 0 to 100V per ring or per cm or per inch of the ion transfer device 20.

In addition, the first electrode unit 31a and the last electrode unit 31d may have additional electrodes 91 with independently-controlled voltages to act as entrance and exit electrodes (or gates) for the ion transfer device 20 on two ends, for example, by decreasing the entrance and exit electrode voltages to allow ions enter or exit the ion transfer device 20, or by increasing the entrance and exit electrode voltages to prevent ions from entering or exiting the ion transfer device 20. This may be necessary when synchronizing the ion transfer device with a pulsed ion source, for example, a laser-based ion source, or when synchronizing the ion transfer device with the ion guide 13 section of a mass spectrometer, or when receiving ions from different ionization sources, or when receiving calibrations ions as disclosed earlier.

The DC voltage sources providing the DC voltages may require RF chokes to prevent the RF voltage from penetrating into the DC power supply. The DC voltages may also be regarded as the DC offset voltage applied to the RF voltage. The RF voltage (two out-of-phase sine waveform applied for radially pushing and maintaining the ions towards a center of the ion transfer device 20) may always be present or may be present during operation of the ion transfer device 20 in the electrodes 91 of the ion transfer device 20. Alternatively, the RF voltage may only be present in the electrodes that hold ions trapped to reduce the power burden on the electronics producing the RF voltages.

FIG. 21 shows RF and DC voltage waveforms applied to the electrodes of the flexible or re-configurable ion transfer device along with simulation results of ion trajectories in accordance with one or more embodiments of the present disclosure. In this figure, an exemplary simulation results for ion trajectories and the ion transfer mechanism disclosed with respect to FIG. 20 is provided at time t1 and t3. Ions with m/z of 1000 are simulated to enter and travel in the ion transfer device 20 at the entrance electrode of the electrode unit 31a. Ions form "nodes" when getting trapped by potential barriers at the end of each of the electrode units 31a-d. A node is defined as one or more ion staying in a trapped state over a period of time in the present disclosure.

Figure 22:
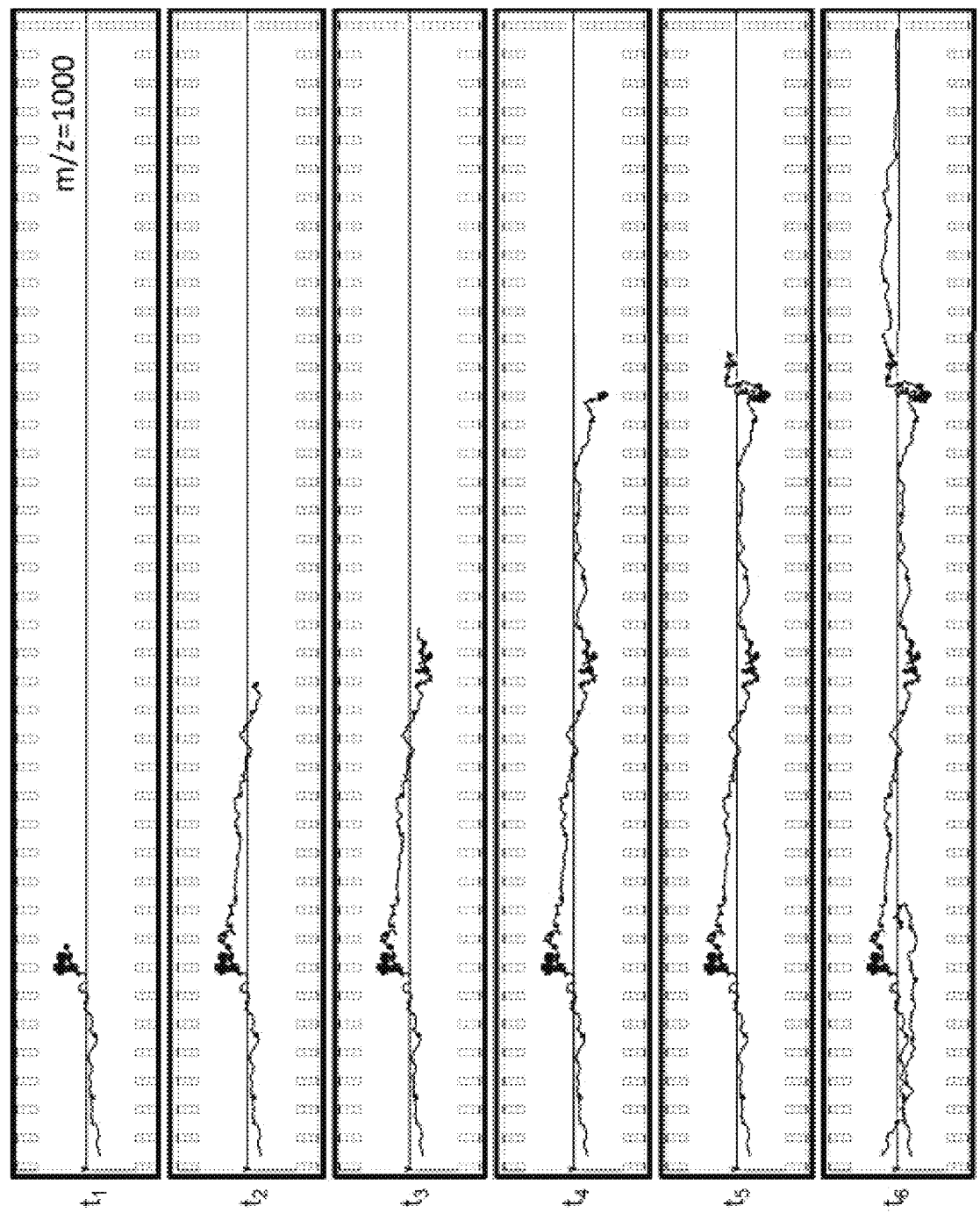
FIG. 22 shows simulation results of trajectory for a single ion with m/z of 1000 in accordance with one or more embodiments of the present disclosure.

FIG. 22 shows simulation results of trajectory for a single ion with m/z of 1000 in accordance with one or more embodiments of the present disclosure. In this figure, an exemplary simulation results for the trajectory and the ion transfer mechanism disclosed with respect to FIG. 20 is provided. Times t1-5 are not necessarily the same as those shown in FIGS. 20 and 21. As noted with respect to FIG. 21, the ion in the ion transfer device 20 forms nodes at the end of each of the electrode units 31a-d.

FIG. 23 shows side view and front view of simulation results of trajectory for ions having with m/z of 100, 500, 1500, and 2000 in accordance with one or more embodiments of the present disclosure. In this figure, an exemplary simulation results for the trajectory and the ion transfer mechanism disclosed with respect to FIG. 20 is provided in both side view and front views. The simulation results show that the ions are transferred in the ion transfer device 20 without any ion loss, resulting in 100% ion transmission. As noted with respect to FIG. 21, the ions in the ion transfer device 20 form nodes at the end of each of the electrode units 31a-d. As the ions' mass to charge (m/z) ratios increase, the ions may form a donut or torus shape around the central axis at the nodes (for example, as illustrated in FIG. 21 and FIG. 23 at m/z of 1500 and 2000) or a hollow cylinder or hollow cylindrical shape (not shown).

The disclosed methods of transferring the ions in the ion transfer device 20 provides the advantage that the ions from samples may be collected very fast, for example, with the frequency of the variable DC voltage as disclosed for moving ions forward in discrete or separate or isolated "ion packets" that may be produced by, for example, one or more than one laser pulse. This enables conducting imaging mass spectrometry much faster than those achievable by conventional mass spectrometry imaging systems and methods that require 5 to 10 seconds for analysis of each spot.

Figure 24:
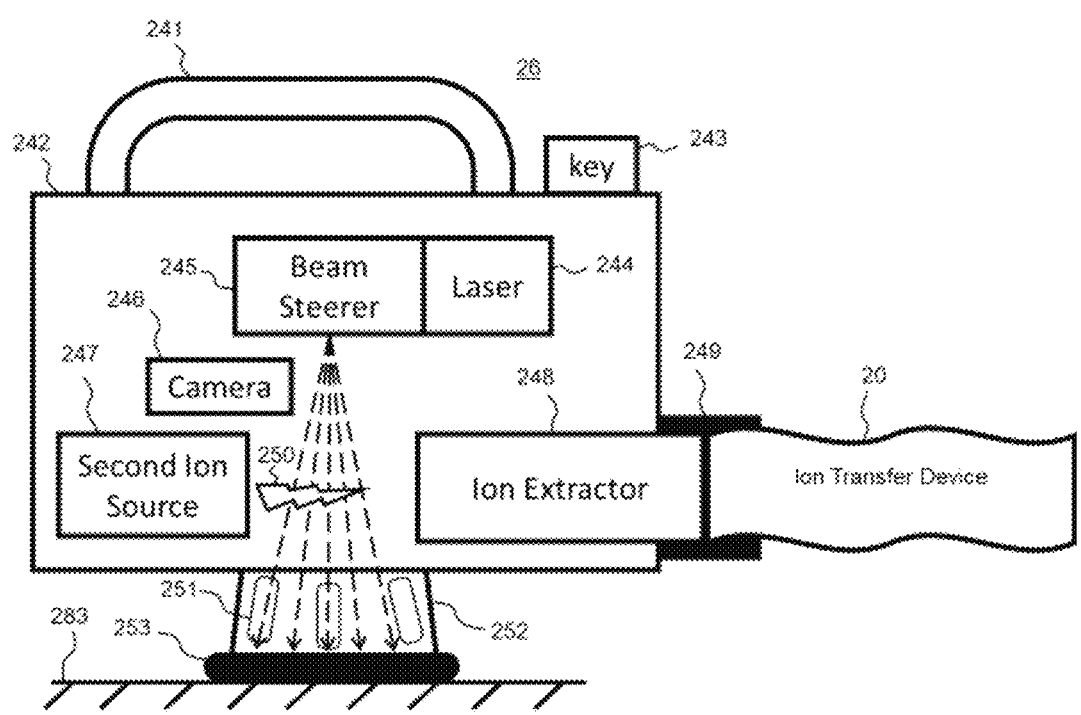
FIG. 24, FIG. 25, and FIG. 26 show block diagrams of one or more embodiments of ionization source probes detached from the mass spectrometer such that ions produced in an ionization probe are efficiently transferred to a mass spectrometer via a flexible or re-configurable ion transfer device in accordance with one or more embodiments of the present disclosure.
Figure 25:
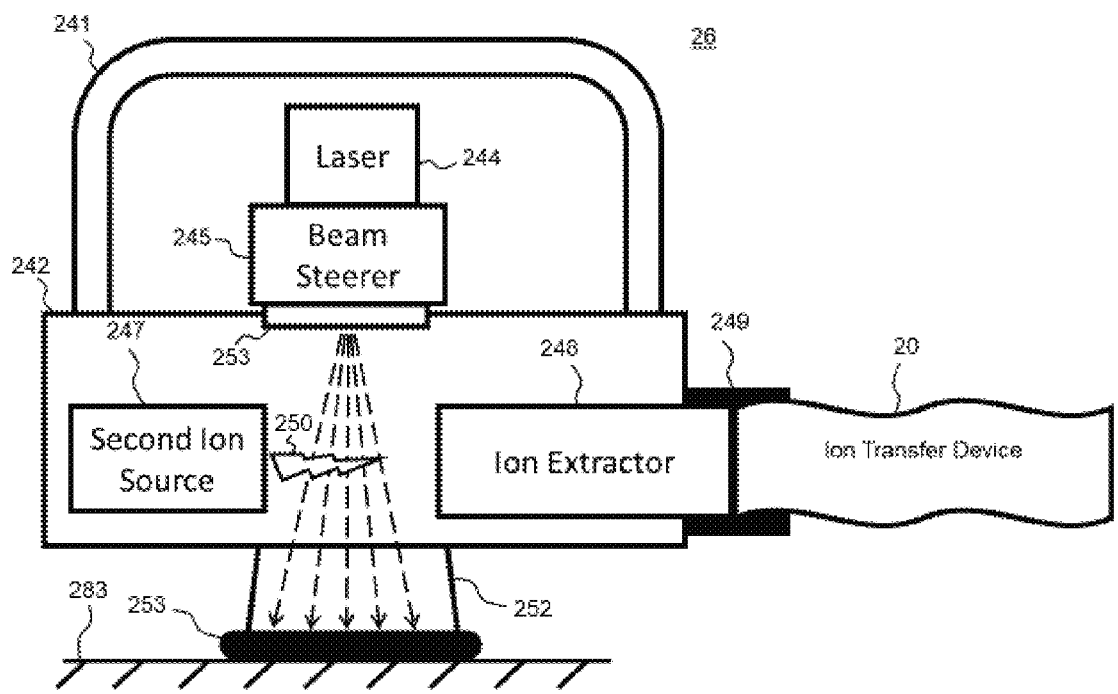
Figure 26:
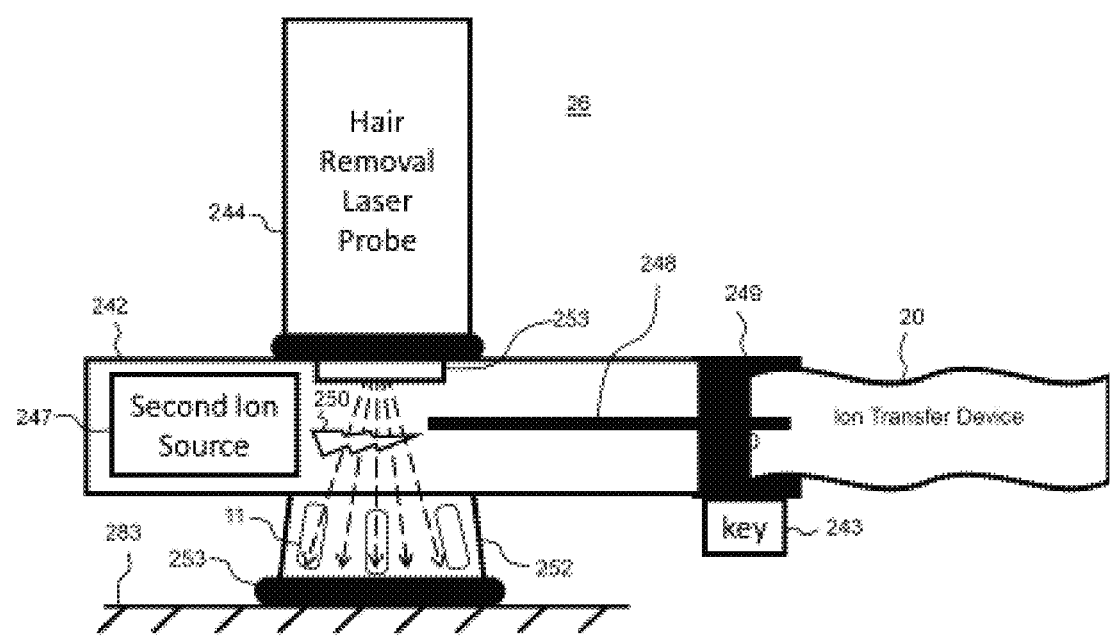

FIG. 24, FIG. 25, and FIG. 26 show block diagrams of one or more embodiments of ionization source probes detached from the mass spectrometer such that ions produced in an ionization probe are efficiently transferred to a mass spectrometer via a flexible or re-configurable ion transfer device in accordance with one or more embodiments of the present disclosure. In FIG. 24, the ionization source probe 26 may include a housing 242, a handle 241, one or more keys 243, a sample interface 252, a sample interface sealing part 253, a plurality of interface openings 251, at least one laser 244, a laser beam steerer 245, a camera 246, a second ionization source 247 that produces one or more ionization mechanism 250. The ionization mechanism 250 may be laser-, chemical ionization-, photoionization-, electrospray-based ionization mechanism. The ionization source probe 26 is put in contact with or placed on a surface under test 283. The surface under test 283 may be biological tissue, a human or animal body organ, or may be any other surface that is being tested and the scope of the present disclosure does not limit the surfaces that may be analyzed with one or more embodiments disclosed. The sample interface 252 and the sample interface sealing part 253 may maintain the focal point of the laser 244 constant if the probe is removed to different areas of the surface 283. The sealing part 253 may seal and create vacuum/reduced pressure (in a range of 0.0001 to 750 Torr) right above the sample and may provide a soft contact between the probe 26 and the surface 283, for example, when the surface is a delicate sample such as biological tissue. Additional wires, tubes for liquid and gas, and optical fibers may be included along the ion transfer device 20 in case, for example, the laser source 244 and a power supply for the secondary ion source 247 are not provided on the probe 26. The laser may be a pulsed laser or a continuous mode laser that may be operated in pulsed mode at UV, VIS, IR, or NIR wavelength.

The operator that may be a human user or a robot, may position the probe 26 on the surface under test 283. During positioning, the camera 246 may produce images that aid and determine a location or a point of interest, for example for molecular profiling, on the surface under test 283. The camera 246 may be a simple microscopic camera or may provide spectroscopic images, for example medical video cameras, in-vivo laparoscopic camera, bioluminescence and/or fluorescence imaging systems, a near-infrared (NIR) fluorescence imaging system, confocal laser endomicroscopy, fiberscopes, or other medical imaging cameras. In one or more embodiments, the camera provides in vivo cellular imaging of the tissue or surface. The camera may include illumination system, such as light emitting diodes or optical fibers that guide light for illumination. The probe may also include tracking system to track a location that the probe is pointing at or sampling from.

After finding right location on the surface 283, then a user (a human or a robot) may press or activate the key 243 to start the sampling and ionization process. The key 243 may be alternatively provided on a footswitch. In one or more embodiments, the laser 244 is a pulsed laser. Each laser pulse produces a plume of desorbed or ablated materials from a point of interest on the surface under test 283. The plume may include both neutrals and ions. In one or more embodiments of the present application, ions are provided next or in a proximity of (for example in range of 0.1 to 10 mm or 10 to 50 mm from the sample) to the sample under test with ambient ionization techniques or reduced pressure ionization techniques, providing the advantage that collecting and guiding the produced ions to a mass spectrometer may be achieved with a higher efficiency compared to neutrals, thus improving the sensitivity. One of ordinary skill in the art would understand that the neutral species produced from the sample that are not ionized by the by ionization sources in a proximity of the sample, are not transferred and analyzed, and only the produced ions from the sample is transferred for analysis. The laser 244 or the beam steerer 245 may optionally have a lens that may be used to focus or de-focus the laser on the surface 283 or to adjust the area that laser interacts with the surface 283, thus adjusting the laser fluence and the area being sampled and analyzed by each laser pulse. Plume of desorbed or ablated materials from a point of interest on the surface under test 283 may contain ions and/or neutrals. The ions in the plume may be extracted by the ion extractor 248, for example by a heated or non-heated capillary inlet that may be floated at a voltage (the extraction mechanism may be based on either gas flow or electric field, or a combination of both) and enter the ion transfer device 20 to be transferred to a mass spectrometer. An adapter 249 may connect the ion transfer device 20 to the probe 26. The plume may also interact with one or more ionization sources at the probe, such as electrospray, plasma, glow discharge, or other ionization methods and techniques disclosed in the present application. In one or more embodiments, the secondary ion source 247 may be, for example, desorption electrospray ionization, that desorbs and ionizes molecules from the surface 283 without the laser beam from the laser 244. The plurality of interface openings 251 maintain the sampling and ionization at a desired pressure, for example in a range of 0.1 to 760 Torr or more. One or more gas flows, such as nitrogen or any other gas, from the plurality of interface openings 251 may be provided for surface cooling or aiding the collection and extraction of ions and neutrals. In one or more embodiments of the present disclosure, the probe 26 may include one or more heating or cooling elements to heat or cool the sample under test to achieve a desired temperature, for example, in the range of −50C to 200C before or after sampling or ionization. FIG. 25 shows one or more embodiment of the probe 26 such that the sampling and ionization is performed at reduced pressure. Therefore, the plurality of interface openings 251 are eliminated or replaced with a leak valve and pressure sensors (located inside the housing 242) that monitors the pressure at which the sampling and ionization take place. The pressure may be lower (0.0001 to 750 Torr) than atmospheric pressure of ~760 Torr. In one or more embodiments, the pressure is maintained at a pressure of the ion transfer device 20. Ionization and sampling at reduced pressure provides the advantage that ion manipulation for collection and extraction may be easier due to reduced collisions with background gas molecules and more control with application of electric fields. In this exemplary embodiment, the sealing part 253 may provide sealing to maintain reduced pressure in the sample interface 252 and inside the probe 26 to improves ion collection and extraction efficiencies. The sealing part 253 may also include a firm mesh to prevent a sample surface 283 that is soft to get sucked into the housing 242. The laser system 244 and the beam steerer 245 (to conduct mass spectrometry imaging to produce molecular profiling maps and images) may include two mirrors controlled with motors may be placed outside of the housing 242 and the laser beam may enter the housing maintained at reduced pressure through a window 253.

FIG. 26 show one or more embodiment of the probe 26 that is similar to FIG. 24 with the difference that a commercial laser 244, such as a commercial or medical laser, for example a hair removal laser probe, is used for producing ions. The key 243 may be used to operate the laser 244 or may be used to control the pressure level (for example in a range of 0.0001 to 750 Torr) in the housing if the housing 242 is maintained at reduced pressure. In one or more embodiment, the ion extractor 248 may be a capillary inlet with an inner diameter of 50 to 1000 micrometers and a length of 1 to 50 cm, or 50 to 100 cm. In one or more embodiment, the ion extractor 248 may be a number of concentric capillaries or tubes such as those shown in FIG. 29B, FIG. 29C, or FIG. 29E. In one or more embodiment, the ion extractor 248 may be a double cone differentially pumped skimmer sampler assembly. In one or more embodiment, the ion extractor 248 may be an ion funnel.

Figure 27:
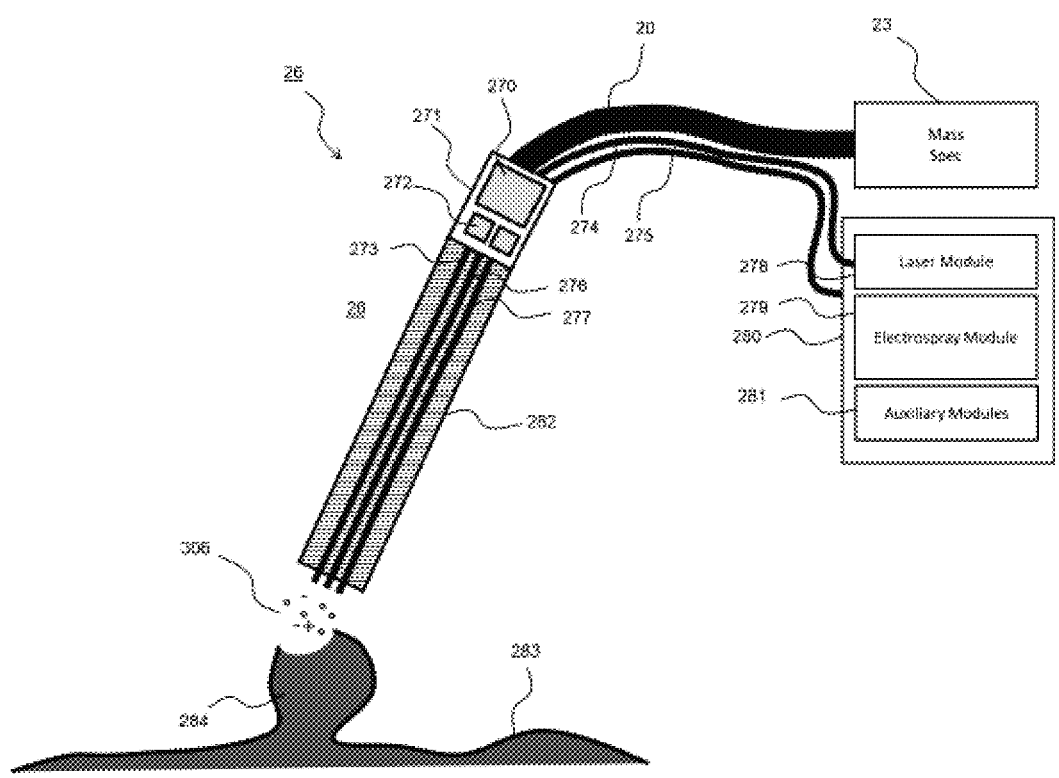
FIG. 27 shows block diagrams of one or more embodiments of mass spectrometry systems and platforms comprising ionization source probes detached from the mass spectrometer such that ions produced in an ionization probe are efficiently transferred to a mass spectrometer via a flexible or re-configurable ion transfer device in accordance with one or more embodiments of the present disclosure.

FIG. 27 shows a block diagram of an embodiment of mass spectrometry system and platform including ionization source probes detached from the mass spectrometer such that ions produced in an ionization probe are efficiently transferred to a mass spectrometer via a flexible or re-configurable ion transfer device in accordance with one or more embodiments of the present disclosure. In FIG. 27, the probe 26 may include a user interface portion 271 and an elongated portion 282 (or body). The user interface portion 271 may include one or more displays 270 that may be a touchscreen display and for example show a user an image, such as chemical or biological composition image, of the surface under test or other instrument control options and menus. The user interface portion 271 may include one or more keys 272 to allow a user to control the probe 26 or control probe parameters for producing ions. The elongated portion 282 may be an endoscope or a catheter (for example a multi-lumen tube having a dimeter of less than 10 mm or less than 5 mm) and may house one or more needles 273, one or more capillary tubing 276, or one or more optical fibers 277. The housing and holding of these may be in a removable or unremovable manner. The elongated portion 282 may include the one or more needles 273, one or more capillary tubing 276, or one or more optical fibers 277 that are disposable and may be removed and disposed after use, for example, after surgery and a new and sterile elongated portion 282 including the one or more needles 273, one or more capillary tubing 276, or optical fibers 277 may be attached to the probe 26. The needles 273, capillary tubings 276, or optical fibers 277 may be removably attached, for example as a cartridge, to the elongated portion 282. The elongated portion 282 may be a catheter or an endoscopy catheter, for example, a medical catheter with multiple lumen that becomes in contact or is inserted, through an incision for example in laparoscopic procedures, into a living human or animal body or tissue for biopsy. Sampling and ionization happen at an end of the elongated portion 282 that comes in close contact with the sample surface 283 and an area of interest 284 to produce ions 306. The ions are produced in a proximity of the sample surface 283. The proximity may be 0.1 to 10 mm, 10 mm to 50 mm, or 50 to 100 mm. The area of interest 284 may be a body organ or a cancer tumor on the surface 283 that may be on or inside human or animal tissue.

The probe 26 may be connected to a mass spectrometer 23 (or ion mobility analyzer) and a probe power and control system 280. The probe power and control system 280 may include a laser module system 278 to support one or more lasers, a second ionization system 279, such as an electrospray module, and/or auxiliary modules 281 that provide power and control systems to the ion transfer device 20 and the probe 26. The auxiliary modules 281 may also include fiberscopes and lighting to observe the area of interest 284. A plurality of tubes 274 and 275 may be used as housing to bring wires for control and power supplies, optical fibers, or liquid and gas to the probe 26. The plurality of lines or tubes 274 and 275 may be bundled with the ion transfer device 20 or may be separately routed to the probe. In one or more embodiments of the present disclosure, the probe 26 may include one or more heating or cooling elements to heat or cool the sample under test to achieve a desired temperature, for example, in the range of −50C to 200C before or after ionization.

The one or more needles 273 and capillary tubing 276 may provide suction or suck in the air (or gas such as nitrogen gas or carbon dioxide in case of laparoscopic surgeries) that may include ions and neutrals 306 produced from the area of interest 284. The tip of the probe where it is next to the produced ions and neutrals 306 are preferably made of conductive material to prevent dielectric charging by produced ions. The one or more needles 273 are metal or conductive to prevent dielectric charging effect. The one or more needles 273 may be a plurality of concentric tubes inserted into each other, plastic, or metal tubes, similar to those shown in FIG. 29B, 29C, or 29E. The one or more optical fibers 277 may have a small lens at the end to focus the laser beam on the area of interest 284. The diameter of the one or more needles 273, capillary tubing 276, or optical fibers 277 may be 0.05 to 5 mm or more. A housing 285 that contains the one or more needles 273, one or more capillary tubings 276, or one or more optical fibers 277 may have a diameter of 2 mm to 20 mm and may be a single channel or multi lumen catheter for example a medical or non-medical endoscope.

Figure 28A:
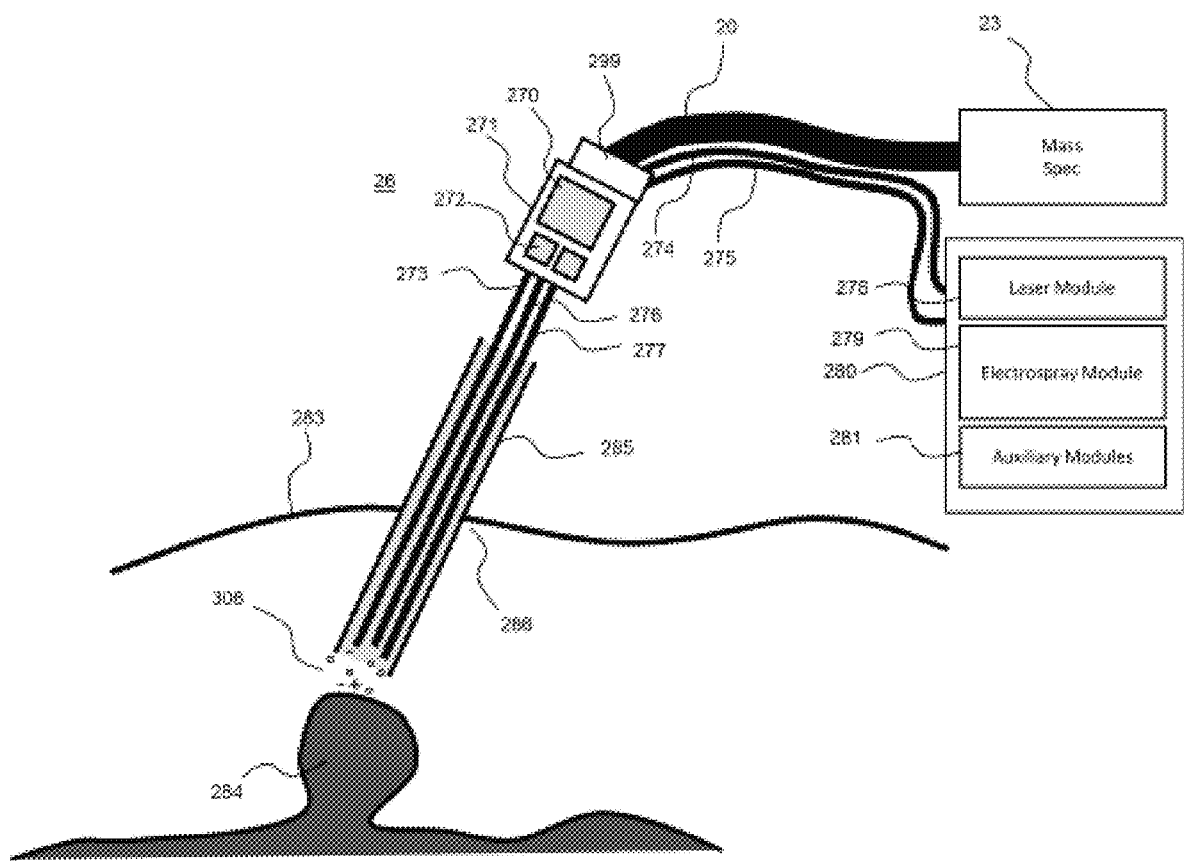
FIG. 28A, FIG. 28B and FIG. 28C show block diagrams of one or more embodiments of mass spectrometry systems and platforms comprising ionization source probes detached from the mass spectrometer such that ions produced in an ionization probe inside the body are efficiently collected and transferred to a mass spectrometer via an endoscopic ion source and a flexible or re-configurable ion transfer device in accordance with one or more embodiments of the present disclosure.

In FIG. 28A, the probe 26 is illustrated as being inserted into a tissue to perform mass spectrometry based in vivo biopsy via an incision 286 by producing ions and neutrals 306 from the area (or sample) of interest 284 that is located beneath the sample surface 283 or inside the body. In one or more embodiments, the term in vivo is defined as any experiments carried out inside of a living system, the smallest unit being a living cell. In one or more embodiments, the term in vivo is defined as in situ. In one or more embodiments, the term in vivo is defined as tests done in an organism (animal or human). In one or more embodiments, the term in vivo is defined as within the cell or cells of an organism. In one or more embodiments, the in vivo analysis tools and methods provided in the present disclosure reduce batch effects, which in ex vivo or in vitro analysis due to a change in nature of the samples by lapse of time. Batch effects occur because measurements are affected by laboratory conditions, reagent lots, and personnel differences.

The probe may have an interface 299 to be connected or removed from the ion transfer device 20 and tubes 274 and 275. The incision 286 may be a natural body orifice (such as ear, nose, rectum, or mouth, etc.) or a small incision (i.e., arthroscopy). Any type of endoscopic procedures that are named for the organ or body area to be visualized and/or treated may be biopsied with one or more embodiments of the present disclosure. For example, the endoscope may be inserted into the gastrointestinal tract (alimentary tract endoscopy), bladder (cystoscopy), abdominal cavity (laparoscopy), joint cavity (arthroscopy), mid-portion of the chest (mediastinoscopy), or trachea and bronchial system (laryngoscopy and bronchoscopy).

Figure 28B:
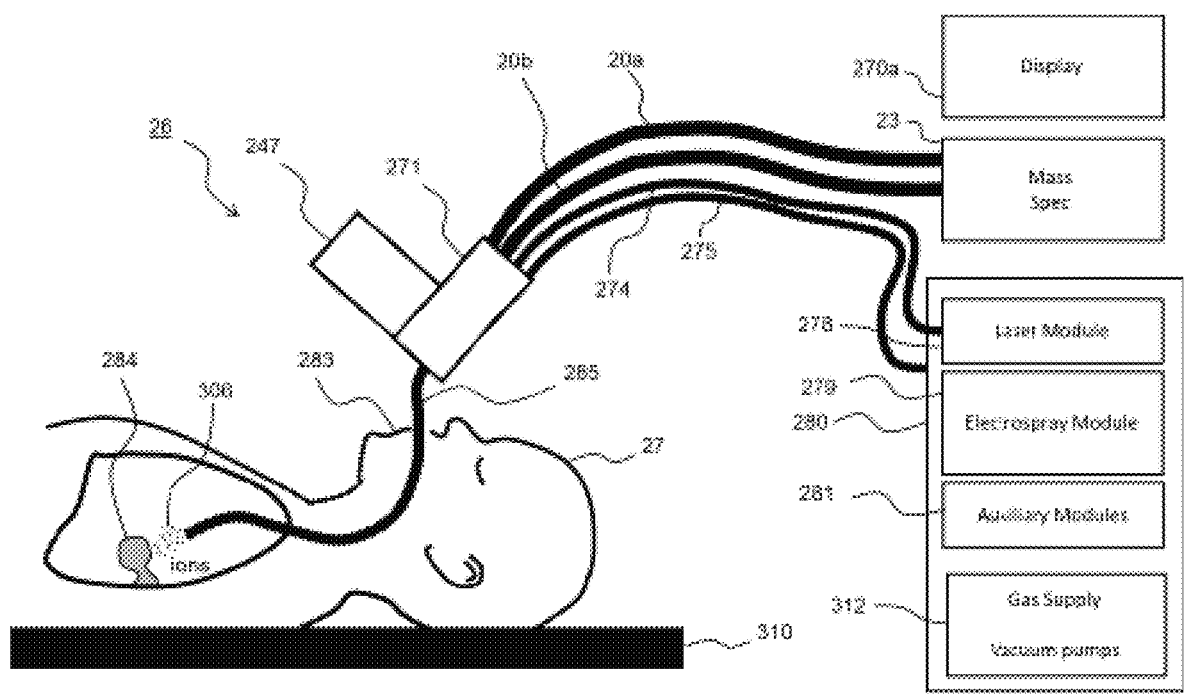

FIG. 28B shows an embodiment of the probe 26 inserted via the mouth of a person's body 27 on a bed 310 into an internal organ to examine molecular profile of the area of interest 284 on f a tumor tissue to perform mass spectrometry based in vivo biopsy by producing ions and neutrals 306 from the area of interest 284 that is located beneath the sample surface 283, which is in this case a human. The probe may include the second ionization source 247. The probe power and control system 280 may further include gas supplies (such as nitrogen, argon, air, oxygen, helium, or any other non-toxic gas) and/or a plurality of air pumps, gas flow pumps, or vacuum pumps 312. A display 270a may be provided to project the view of the end of the probe 26 from the location ions are produced and/or may provide analysis results, prognosis or diagnosis results, spectrometric data and/or information about molecular profiles for the area of interest 284. One or more ion transfer devices 20a-b may be used to transfer the produced ions 306 to the mass spectrometer 23, for example from two or more different locations on the area of interest 284.

Figure 28C:
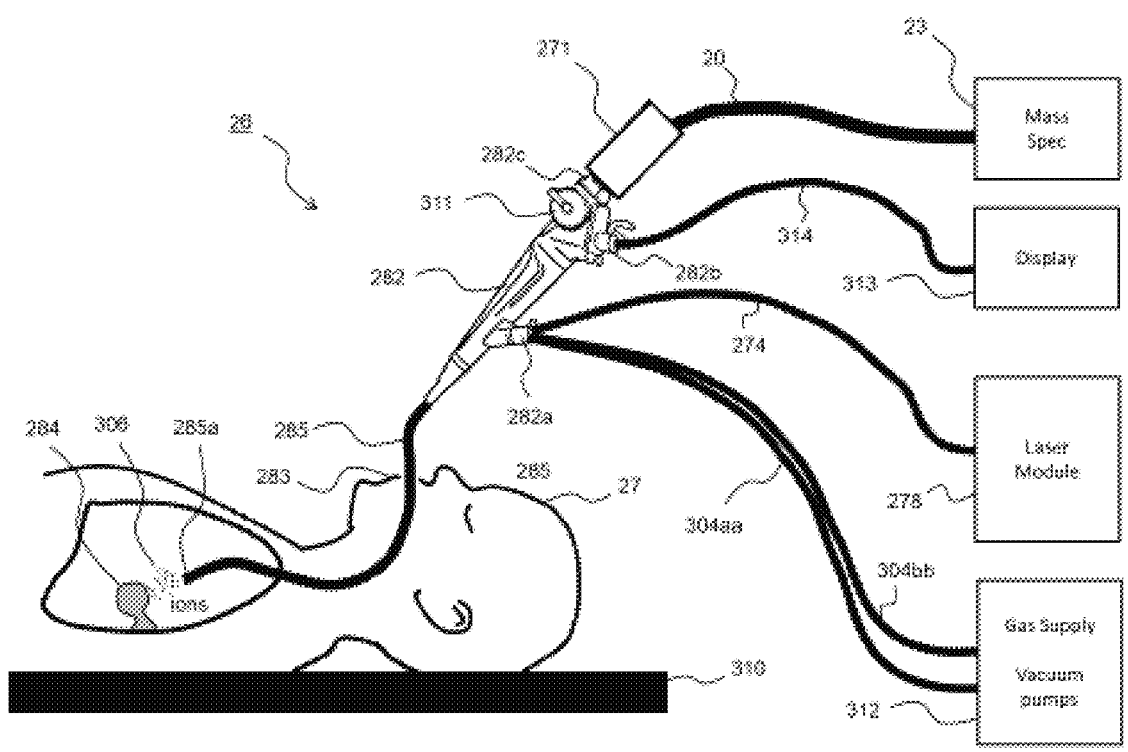

FIG. 28C shows an embodiment of the probe 26 inserted via the mouth of a person's body 27 on a bed 310 into an internal organ to examine molecular profile of the area of interest 284 on f a tumor tissue to perform mass spectrometry based in vivo biopsy by producing ions and neutrals 306 from the area of interest 284 that is located beneath the sample surface 283, which is in this exemplary illustration is a human 27. The probe may include an elongated portion 282 that may be a conventional endoscope with a light source and a fiber optic video camera at the tip such that images of the inside of the body 27 are displayed on an external screen 313 where photos can be taken, or the procedure recorded. The elongated portion 282 that may be the conventional endoscope may include wheels 311 that control position of the endoscope tip for navigation inside the body 27. The elongated portion 282 is extended into and inside the body 27 through a housing 285 that may be a catheter or an endoscope. The elongated portion 282 (which may be the conventional endoscope) may include one or more channels 282a-b. The one or more channels may be used as instrument ports for inserting one or more endoscopic forceps, tubes carrying water, saline, air and/or vacuum, for example, for cleaning or extracting produced ions 306, or for taking endoscopic biopsy samples from the sample of interest 284. The endoscope may include an endoscope interface 282c to connect to an interface portion 271 of the ion transfer device 20. A laser module system 278 may providing laser beams or pulses to one or more optical fibers to reach the sample of interest 284. The gas supply and vacuum pumps module 312 may provide the gas flow and vacuum suction to maintain the tip of the endoscope at a constant pressure, for example at atmospheric pressure.

In an exemplary operation, an operator, for example, a surgeon or a surgical robot first inserts the housing 285 via mouth of the body 27 to reach an internal organ and the area of interest 284 such as a tumor or a cancer tumor or a tissue. The operator uses one or more wheels 311 to bend the tip of the endoscope to navigate inside the body 27 while observing the camera view of internal pathway. Upon reaching the tumor, the operator then may insert one tool via the one or more channels 282a-b. Depending on the intended operation, the operator may take out and insert a new tool via the one or more channels 282a-b. For example, to perform in vivo biopsy in accordance with one or more embodiments of the present application, an operator may insert one or more optical fibers 274, one or more metal or plastic tubing 304aa-bb via the one or more channels 282a-b. The produced ions 306 then are sucked back to the interface portion 271 (neutrals may be ionized by one or more ion sources in the probe 26) and transferred to the mass spectrometer 23 for analysis. The mass spectrometer then analyzes the ions and separates them based on mass to charge ratio and provides one or more spectrum. The spectrum then is analyzed by a computer and the identified molecules are compared to a data base and prognosis or diagnosis are provided to the operator, for example, based on verification of biomarkers corresponding to a specific disease or medical condition. Severity, grade, stage, presence or absence of a disease or medical condition in one of more regions of the sample may be determined.

Endoscopy may be performed by insertion of a long, housing 285 in form of thin or elongated tube directly into the body 27 to observe an internal organ or tissue 284. Endoscopy may be used to carry out other tasks including imaging and minor surgery. The endoscopy may be used to investigate many systems within the human body; these areas include: Gastrointestinal tract: esophagus, stomach, and duodenum (esophagogastroduodenoscopy), small intestine (enteroscopy), large intestine/colon (colonoscopy, sigmoidoscopy), bile duct, rectum (rectoscopy), and anus (anoscopy); Respiratory tract: Nose (rhinoscopy), lower respiratory tract (bronchoscopy); Ear: Otoscopy Urinary tract: Cystoscopy Female reproductive tract (gynoscopy): Cervix (colposcopy), uterus (hysteroscopy), fallopian tubes (falloposcopy); Through a small incision: Abdominal or pelvic cavity (laparoscopy), interior of a joint (arthroscopy), organs of the chest (thoracoscopy and mediastinoscopy).

Figure 29A:
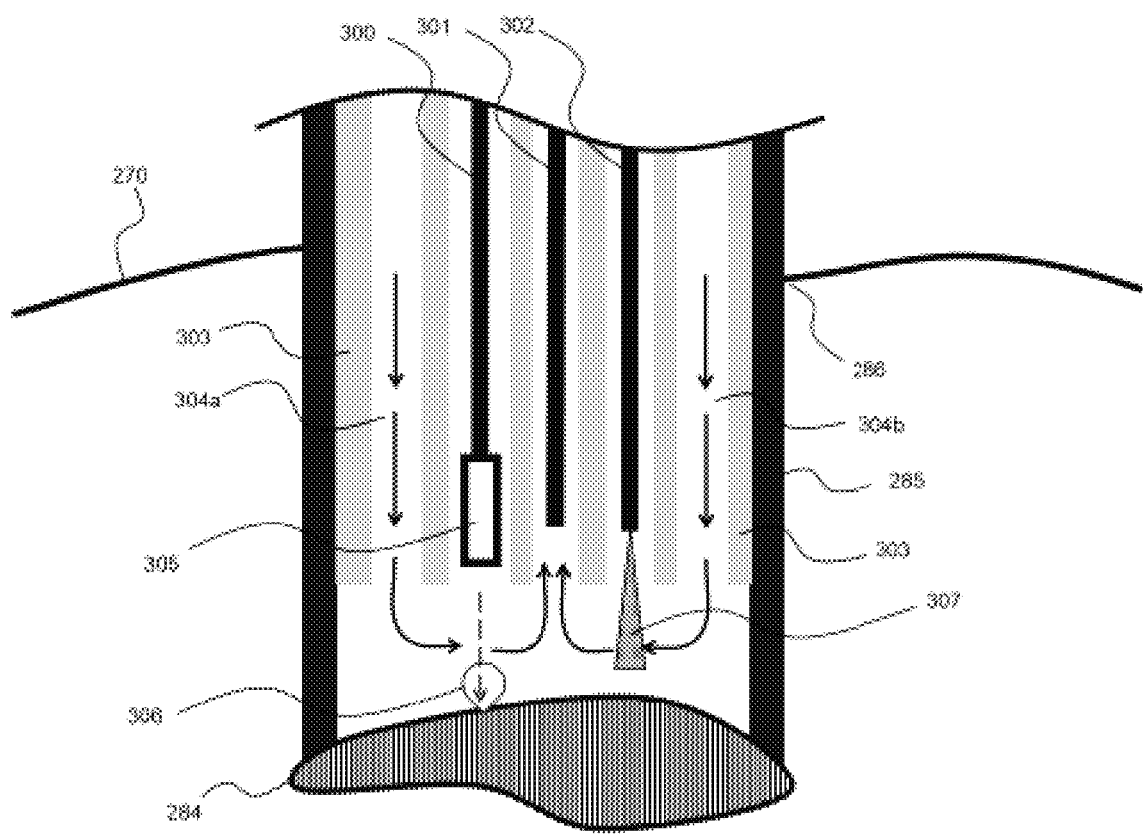
FIG. 29A, FIG. 29B, FIG. 29C, FIG. 29D, FIG. 29E, FIG. 29F, FIG. 29G, FIG. 29H, FIG. 29I, and FIG. 29J show close-up views of one or more embodiments of endoscopic probe tips of ionization source probe of a mass spectrometry system and platform inserted into tissue or body for in vivo ionization and biopsy through an incisional or non-incisional endoscopy procedure in accordance with one or more embodiments of the present disclosure.

FIG. 29A-J show one or more embodiments of probe and probe tips of ionization source probe of a mass spectrometry system and platform inserted into tissue for in vivo ionization and mass spectrometry in accordance with one or more embodiments of the present disclosure. The incision 286 may be a natural body orifice (such as rectum or mouth) or a small incision (such as arthroscopy). FIG. 29A-J show close-up views of one or more embodiments of portions of FIG. 28A-C. FIG. 29A shows only the end of the probe 26 that meets the sample of interest 284 and the cut-off portion on the top part of this figure extends and connects to the probe 26 at the interface portion 271. The probe tip may include a multi lumen catheter 303. An optical fiber 300 including a focusing laser head or integrated lens 305, a capillary inlet 301 (for example including one or more concentric tubes) and an electrospray needle 302 producing a spray 307 may be inserted in the different lumens of the catheter 303. The different lumens may be accessed via the one or more channels 282a-b. In one or more embodiments, the catheter 303 is inserted from one of one or more channels 282a-b of the probe. In one or more embodiments, the one or more optical fibers 300, the one or more capillary inlets 301, and the one or more electrospray needle 302 are inserted through different channels of the one or more channels 282a-b. The focusing laser head or integrated lens 305 may be fabricated by post processing an optical fiber by creating a curvature that acts as a lens at the end of the optical fiber 300. In one or more embodiments, a grin lens may be included at the end of optical fiber for focusing the laser beam (which may be pulsed beam) on tissue. The catheter 303 may also include two or more channels or lumens 304a-b to provide a channel for gas flow that may be pressure-controlled or flow-controlled. One or more laser pulses desorb or ablate a portion of the sample of interest 284 and create a plume 306. The plume may include ions and/or neutrals. The plume 306 then interacts with a second ionization source to go through a second ionization process. The second ionization process may ionize the neutrals, may further ionize the ions to a higher charge state (charge state is defined by the amount of positive or negative charge a charged particle has), and/or may fragment the neutrals and ionic species to produce one or more fragment ions. The second ionization process may be applied, for example by an electrospray source with the spray 307 from the electrospray needle 302. The spray 307 interacts with the plume 306 that is moving towards the capillary inlet 301 by suction and the neutrals are mixed with the spray 307 composed of charged droplets. Then all the ions and neutrals mix with charged particles of spray 307 and get sucked into the capillary needle 301 and transferred to ion transfer device 20, and then the mass spectrometer 23 via the ion transfer tube 20. The second ionization source may for example be a UV laser or a UV ionizing lamp or LED, a gas discharge, etc. that is applied after the ablating laser, that is usually IR, NIR, MIDIR lasers that ablates or/desorbs particles from the sample surface 284. The pressure in the region at the tip of the probe may be regulated by controlling the gas flow in airways 304a-b and the suction from the capillary 301. In one or more embodiments, the electrospray may be located at the interface 271 and the ablated plume interact with the spray 307 inside the probe 26. Although FIG. 29A shows that the optical fiber 300, the capillary inlet 301 and the electrospray needle 302 are at the same distance and perpendicular to the surface under test 284, but the distance between each of these parts may be different from the surface under test 284. Also, the angles that these parts are positioned with respect to each other may be different.

One of ordinary skill in the art would recognize and appreciate that obtaining optimal conditions may be performed by observing the produced signal from the surface under test 284 and adjusting the parameter. The tip of catheter 303 may be tapered or may have one or more covers to isolate the tip of catheter form bodily fluids.

It is important to note that the present disclosure creates ions from the sample of interest 284 in a proximity of the sample of interest 284 that is located at a distance (for example 0.5 m to 100 m) from a mass spectrometer. The proximity may be defined as a distance between 0.1 to 100 mm. It is also important to note that transfer of ions to the mass spectrometer at a distance is much more efficient using the ion transfer device 20 than the transfer of neutrals with a bare tube or the ion transfer device 20. Therefore, in one or more embodiments of the present disclosure, the produced neutrals (product of ablation/desorption process that includes aerosols, vapor, particles, and clusters, etc.) from sample is ionized at the proximity of the sample of interest 284, for example by a secondary ionization source as disclosed in the present application, before entering the transfer tube 20 for efficient transfer to the mass spectrometer. Such secondary ionization does not need to be at the molecular level; for example, the aerosols, particles, and clusters produced by one or more laser ablation/desorption processes (defined as ablation and desorption, ablation or desorption, or ablation and/or desorption) may be ionized to form ionized or charged aerosols, ionized or charged particles, and ionized or charged clusters. It is further important to note that it is an object of the present disclosure to eliminate the need for ionization at the mass spectrometer which is located at a distance from the sample and provide ionization at a distance from a mass spectrometer in a proximity of the sample of interest 284 (in other words to decouple an ion source from a mass spectrometer). This is an important consideration because transfer of ions may be achieved with high efficiency with the ion transfer tube 20 as disclosed in the present application. This may be described similar to containing and transferring photons in an optical fiber. One ordinary skill in the art understands that if smoke is produced from a sample, the produced smoke from a sample mostly includes carbon clusters and molecular information is lost if smoke is produced.

Such an efficient mechanism for transferring neutrals is not available mainly because the only mechanism to control the flow of neutrals from a sample at a distance to a mass spectrometer is gas flow. Significant technical challenges exist for efficient transfer of low abundance gas phase analyte neutrals of interest from a proximity of a sample at a distance into ion analysis system over a long distance. The main mechanism of neutral (and also ion) losses with long tubing (if transfer is performed only with assistance of gas flow) are radial diffusion to the walls, and in case of plastic tubing is the adhesion of the ions and neutrals to the inner walls of the tubing. This results in charge build up, cross-contamination, and loss of important analyte molecules. All of this results in loss of analytical performance and sensitivity. In contrast, ions and charged particles may be transferred inside the ion transfer device 20 with aid of electrical fields as disclosed in the present application, and therefore, a high level of ion transfer efficiency from sample to a mass spectrometer at a distance is achieved. Such a high level of transfer efficiency is particularly important in analytical and medical biopsy applications for improving sensitivity while providing in vivo analysis.

The one or more lasers as disclosed in the present application may be CO2 lasers, used to cut, vaporize, ablate and photo-coagulate soft tissue; diode lasers; dye lasers; excimer lasers; fiber lasers; gas lasers; free electron lasers; or semiconductor diode lasers. Further, the laser may be any one of the lasers used in many types of surgical procedures. Some examples include lasers used in: cosmetic surgery (to remove tattoos, scars, stretch marks, sunspots, wrinkles, birthmarks, spider veins or hair); refractive eye surgery (to reshape the cornea in order to correct or improve vision as in LASIK or PRK); dental procedures (such as endodontic/periodontic procedures, tooth whitening, and oral surgery); or general surgery (such as tumor removal, cataract removal, breast surgery, or plastic surgery). In one or more embodiments, the laser may be thulium fiber laser (TFL) or holmium: YAG (Ho: YAG) laser that may be used in laser lithotripsy procedures. Holmium laser emits at a wavelength of 2100 nm which is highly absorbed by water and biological tissue. The TFL may have several potential advantages, including a four times lower ablation threshold, a near single-mode beam profile, and higher pulse rates, resulting in up to several times as fast ablation rates and faster procedural times. The laser may be coupled to fiber diameters of 1-2000 microns, for example, fiber diameters of 200-550 microns. The laser may have a wavelength 200 nm to 2.1 µm or 300 nm to 3 µm, the average power of the laser may be 0.1 to 500 W, for example, 20 W, 40 W, or 60 W, the repetition rate of the laser may be 0.001 to 2000 Hz, or may be up to several KHz. The energy per pulse may be 0.001 mJ to up to 50 J. The pulse duration may be in the range of 1 to 1000 femtoseconds, 1 to 1000 picoseconds, 1 to 1000 nanoseconds, 1-1000 microseconds, or 1-1000 milliseconds. The laser beam delivery may be performed by using flexible silica fibers, quartz fibers, disposable fibers, single-use, liquid-cooled fibers, and/or medical fibers. The one or more lasers may be activated by a single or double footswitch. The laser may be a class 3 or 4 laser. A coaxial flow of gas or liquid may be transmitted around the fiber and out through the distal tip. The fiber tip may be ball-shaped or may include focusing elements such as a grin lens. The fiber may be a photonic-crystal fiber.

The one or more embodiments disclosed in this application may be used in minimally invasive procedures or minimally invasive surgeries and encompass surgical techniques that limit the size of incisions needed to lessen wound healing time, associated pain and risk of infection. The one or more embodiments may be used in open surgery, in which incisions made leave large wounds that are painful and take a long time to heal. The one or more embodiments may be used in imaging surgical techniques where interventional instruments are directed throughout the body by a radiologist by way of catheters instead of large incisions needed in traditional surgery (for example, in image guided surgeries). The one or more embodiments disclosed in this application may be used in diagnostic techniques or may be combined with diagnostic techniques that do not involve the puncturing of the skin or incision, or the introduction into the body of foreign objects or materials, known as non-invasive or minimally invasive procedures. An example is monitoring skin cells or tumors on a skin. The one or more embodiments disclosed in this application may be used with laparoscopic devices and remote-control manipulation of instruments with indirect observation of the surgical field through an endoscope or large-scale display panel and may be carried out through the skin or through a body cavity or anatomical opening. The one or more embodiments disclosed in this application provide real-time biopsy results when used in minimally invasive procedures such that a patient may require only an adhesive bandage on the incision, rather than multiple stitches or staples to close a large incision, resulting in less infection, a quicker recovery time and shorter hospital stays, or allow outpatient treatment.

Figure 29B:
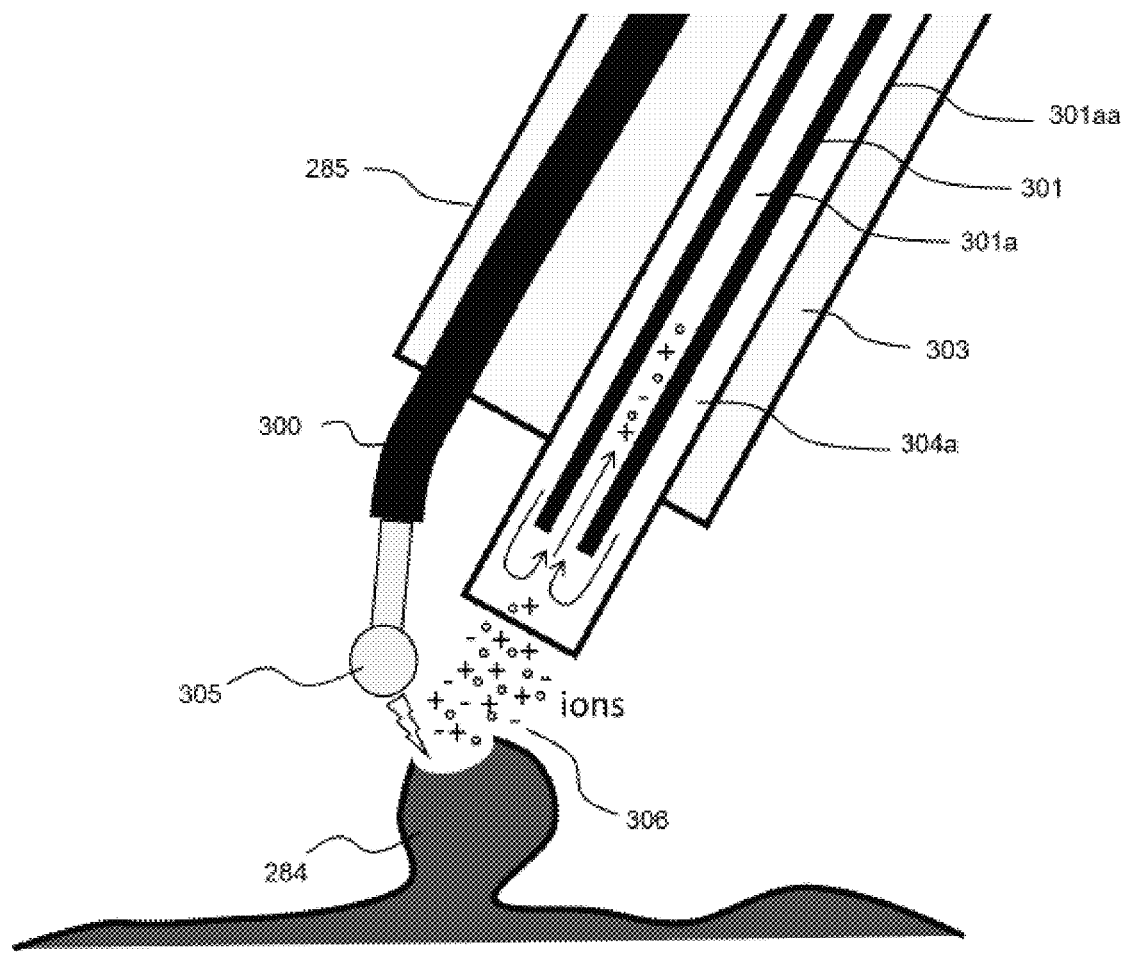

FIG. 29B shows the end of the probe 26 that meets the sample of interest 284. The housing 285 may include a multi lumen catheter 303. The following may be inserted in the different lumens of the catheter 303: an optical fiber 300 including a focusing laser head or integrated lens 305, a capillary inlet 301 inserted inside 304a of second capillary tubing 301aa and hold in the central portion of the second capillary inlet 301aa. The capillary inlet 301 sucks the ions 306 produced by the laser pulse and guides it into the ion transfer device 20. Gas flow (shown by arrows) may be provided from the inside 304a of the second capillary tubing 301aa to act as sheet or curtain gas, and/or to keep the tip of the probe at a constant pressure, for example at atmo-spheric pressure while providing a directed gas flow to efficiently extract the ions from an area above the sample. In one or more embodiment, curtain gas flow or other independent gas stream may carry a portion of calibrant ions and droplets to the sampling inlet.

The focusing laser head or integrated lens 305 may be fabricated by post processing an optical fiber by creating a curvature that acts as a lens at the end of the optical fiber 300. In one or more embodiments, a grin lens may be included for focusing the laser beam on tissue. The catheter 303 may also include two or more concentric channels or lumens 301a and 304a to provide a passage for gas flow that may be pressure-controlled or flow-controlled or both. One or more laser pulses desorb or ablate a portion of the sample of interest 284 and creates a plume and ions and neutrals 306. The plume may include ions and/or neutrals. The plume 306 then get sucked into a channel 301a interact with a second ionization source upstream the channel 301a (not shown in FIG. 29B) to go through a second ionization process. The second ionization process may be optionally applied, for example by an electrospray source upstream the channel 301a (not shown). The second ionization source may for example be a UV laser or a UV ionizing lamp or LED, a gas discharge, etc. that is applied upstream the channel 301a (not shown). The pressure in the region at the tip of the probe may be regulated by controlling the suction from channel 301a or the gas flow in channel 304a, or both. Also, the angles that these parts are positioned with respect to each other may be different. One of ordinary skill in the art would recognize and appreciate that obtaining optimal conditions may be performed by observing the produced signal from the surface under test 284. The tip of catheter 303 may be tapered or may have one or more covers to isolate the tip of catheter from bodily fluids.

Figure 29C:
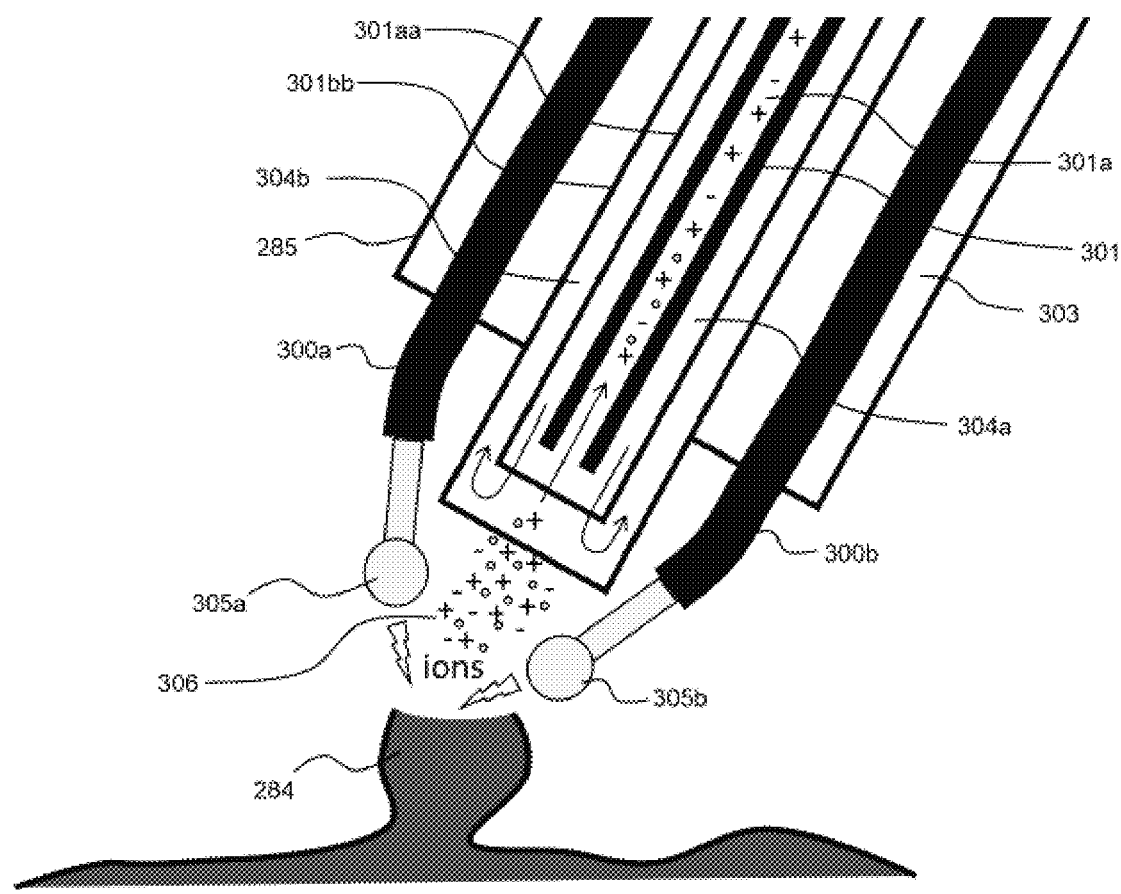

FIG. 29C shows the end of the probe 26 in one exemplary embodiment that meets the sample of interest 284. This exemplary embodiment includes two or more optical fibers 305a-b. Each of the two or more optical fibers 305a-b may be of a different wavelength and pulse energy produced by two or more different laser sources (not shown). For example, an IR laser (IR laser may be 700 nanometers (nm) to 1 millimeter (mm) of the spectrum) may ablate the sample to produce a plume and then a second UV laser may ionize the ablated plume 306. Also, FIG. 29C shows an exemplary channel configuration for suction of produced ions with curtain gas configuration. In this configuration three different channels 301a, 304a-b are provided for vacuum and gas flow. The gas flow is shown by the arrows. The gas travels to the tip via channel 304a and gets sucked in back to the tip via channels 301a and 304b, thus creating a curtain gas for efficient extraction of the plume 306 that results in improved sensitivity.

Figure 29D:
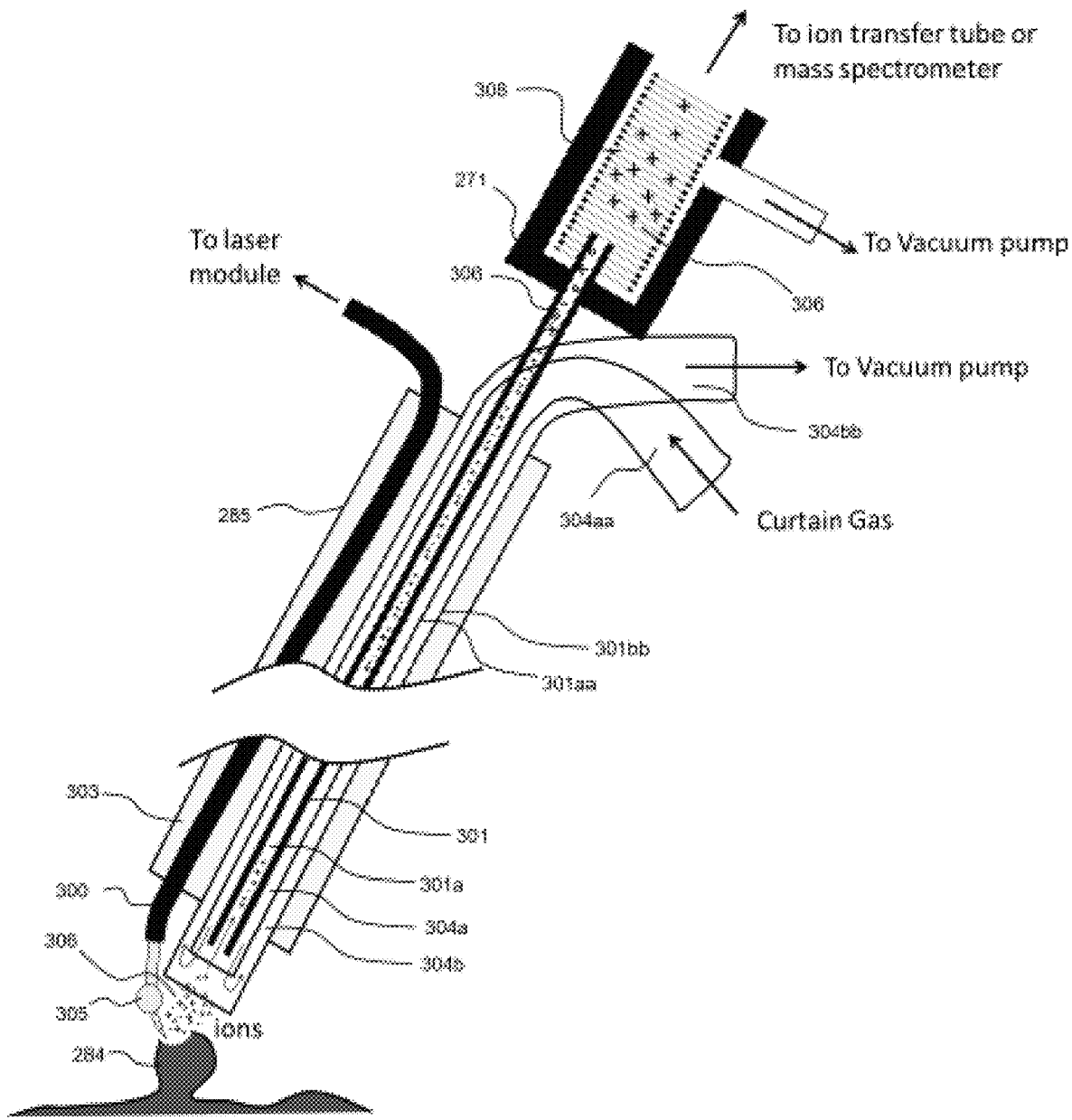

FIG. 29D shows the tip or end of the probe 26 as well as the interface portion in one exemplary embodiment. The plume 306 travels through the channel 301a and exits the end of the capillary tubing 301 and enters the user interface portion 271. The interface portion 271 may be in form of an ion funnel. Depending on the voltages applied to the ion funnel, either positive or negative charges are extracted by the funnel and transferred to the ion transfer tube 20. FIG. 29D shows positive ion mode. The remaining negative ions and neutrals are lost or pumped out. One or more vacuum pumps may provide vacuum to via channel 304aa or the channel shown on the interface portion 271. In one or more embodiments, the vacuum inside the user interface portion 271 may be provided by the first vacuum stage of the mass spectrometer located at a distance. One or more channels 304*aa* provide a controlled gas flow.

Figure 29E:
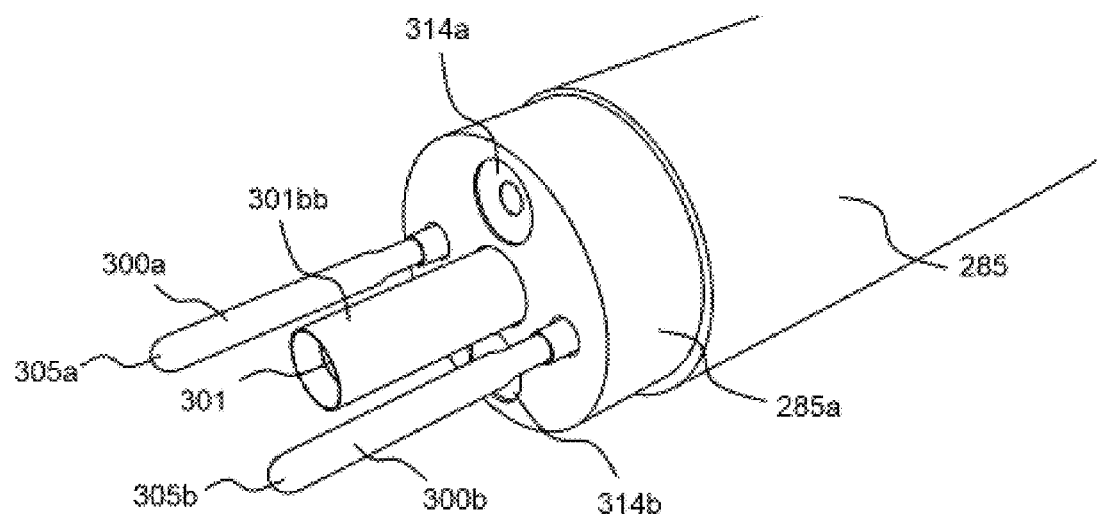
Figure 29F:
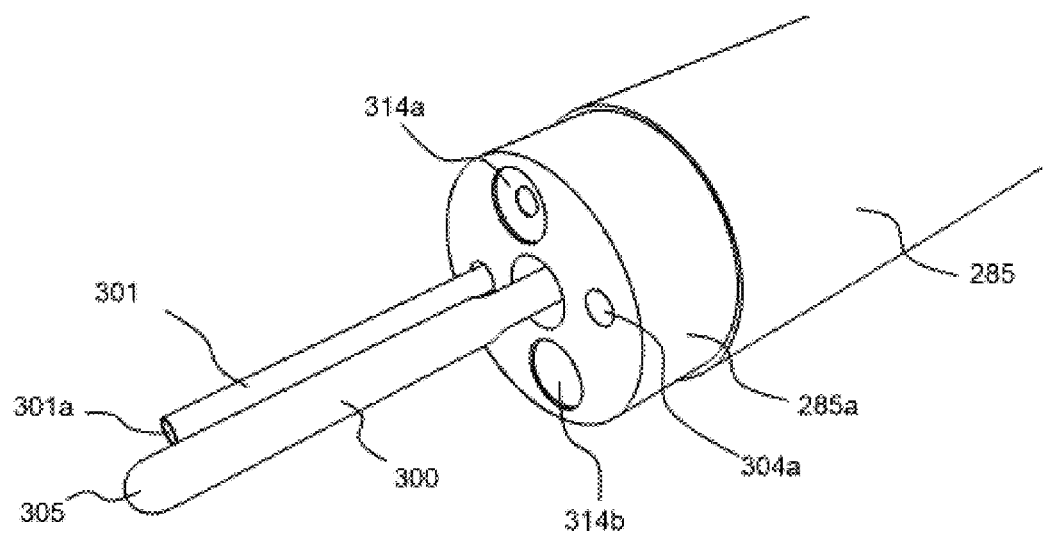
Figure 29G:
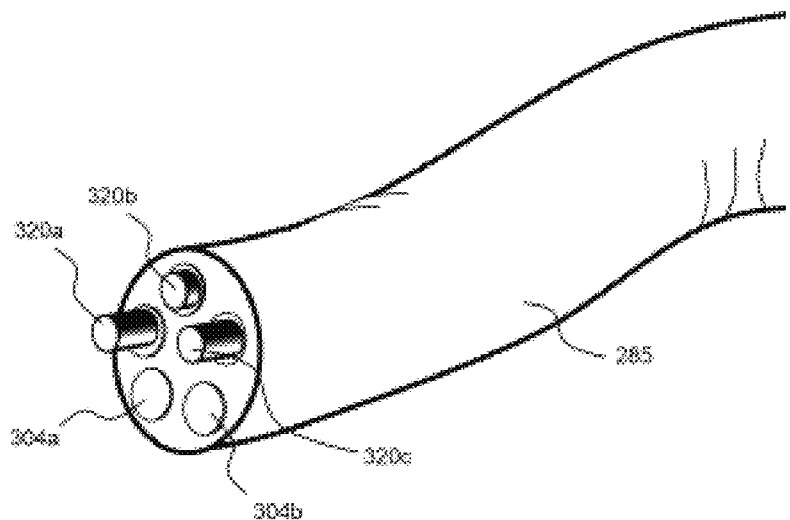
Figure 29H:
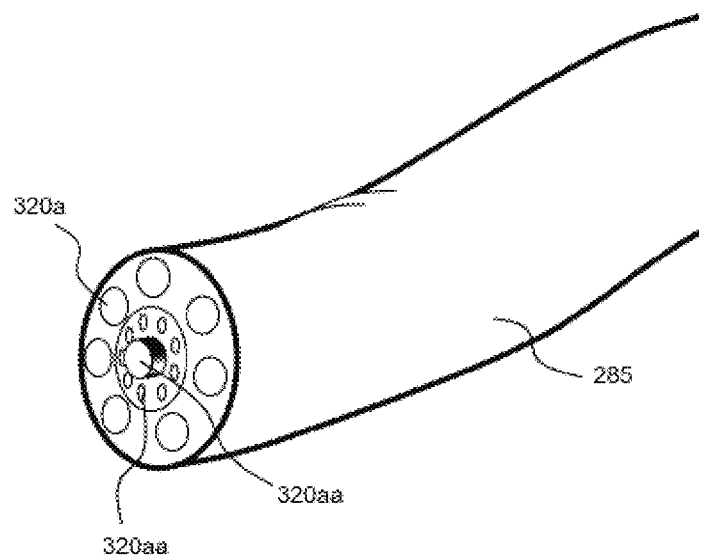
Figure 29I:
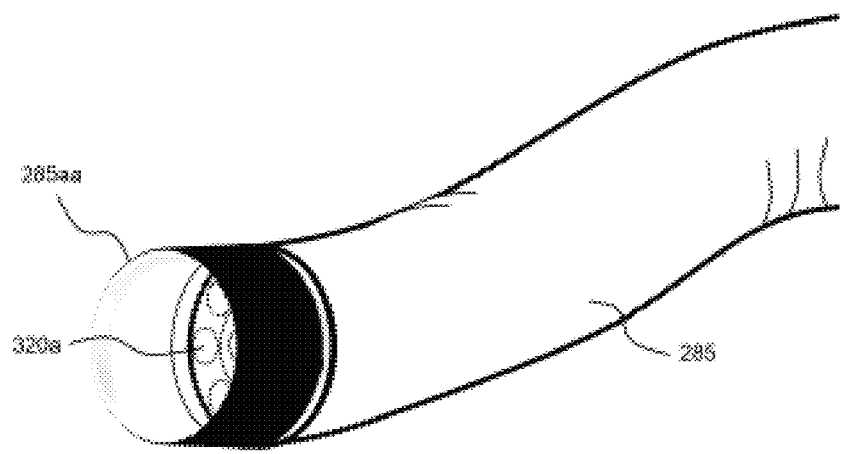
Figure 29J:
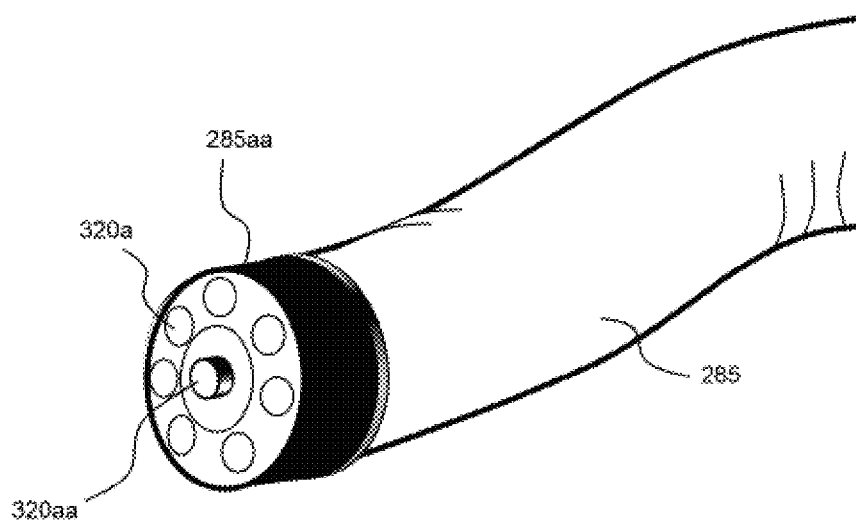

FIGS. 29E and 29F show the end of an endoscopic probe housing 285 in one or more exemplary embodiments. The endoscopic probe housing 285 may include a probe tip 285*a* having a camera 314*a*, a light 314*b* such as LED light, and one or more optical fibers 300, 300*a-b* having focusing lenses 305 and 305*a-b*, one or more capillary suction tubing 301, 301*bb* having a plurality of channels 301*a* for ion suction and gas flow. One or more channels 304*a* may be further provided to be used for additional endoscopic tools, for example for heating or cooling endoscopic inserts to treat the sample before or after each laser pulse or to clean the area from bodily fluids before laser pulses or clean the potential bleeding after laser pulse or use other endoscopic tools or other ionization sources as disclosed in the present application. FIG. 29E shows an embodiment that includes two or more optical fibers 305*a-b*. Each of the two or more optical fibers 305*a-b* may be of a different wavelength and pulse energy produced by two or more different laser sources (not shown). For example, an IR laser may ablate the sample to produce a plume and then a second UV laser may ionize the ablated plume 306 in a two-step ionization process.

FIGS. 29G-J show one or more embodiments of the endoscopic probe housing 285 in accordance with the present disclosure. A plurality of ionization sources 320*a-c* may be provided at the end of endoscopic probe housing 285 for production of ions. The tip of endoscopic probe housing 285 may be further included as a protective cover 285*aa* at the end of the endoscopic probe housing 285. One or more channels 320*aa* may provide passage for gas flow or channels for suction of ions.

Figure 30A:
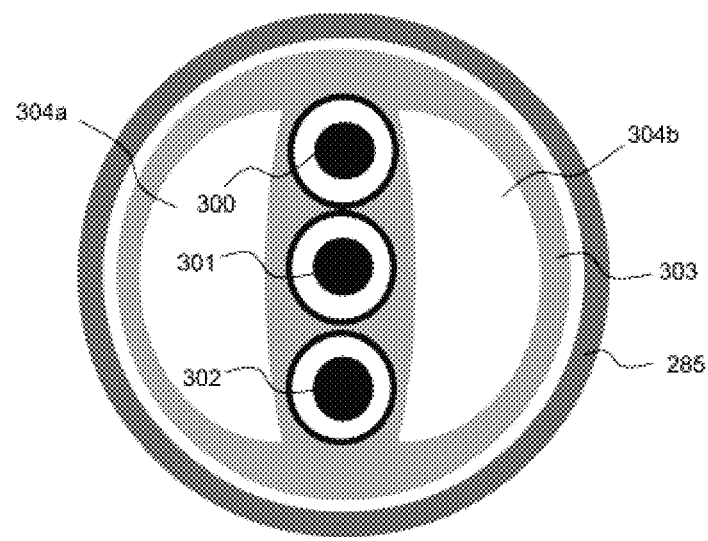
FIG. 30A and FIG. 30B show exemplary embodiments of endoscopic ionization probes for mass spectrometry based in vivo biopsy through incisional or non-incisional procedure in accordance with one or more embodiments of the present disclosure.

FIG. 30A shows a cross-section view of a surgical catheter tubing for use with a probe tip of ionization source probe of a mass spectrometry system and platform inserted into tissue for in vivo ionization in accordance with one or more embodiments of the present disclosure. A multi-lumen (or multi-channel) catheter 303 may include one or more channels for optical fiber 300, one or more capillaries 301, one or more optical fibers or one or more electrospray needles 302, and one or more channels for air flow 304*a-b*. The catheter 303 may be inserted into a housing 285, for example, a single channel catheter that is inserted into the body through the incision 286 during surgery. The one or more optical fiber 300, one or more capillaries 301, one or more electrospray needles 302 may have additional tubing for further electrical isolation of voltages, grounding at the end of electrospray needle, or to provide a slippery surface.

Figure 30B:
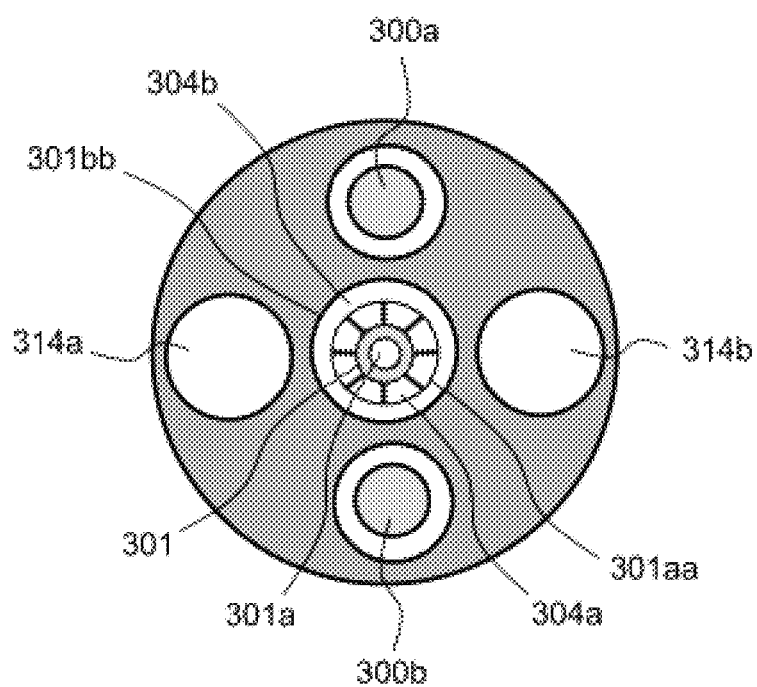

FIG. 30B shows a cross-section view of a surgical catheter tubing for use with a probe tip of ionization source probe of a mass spectrometry system and platform inserted into tissue for in vivo ionization through an incision in accordance with one or more embodiments of the present disclosure. A cross-section of a multi-lumen (or multi-channel) tubing (which may be made of heat shrinkable or regular tubing) or catheter in an exemplary embodiment is shown in FIG. 30B that includes one or more channels for optical fibers 300*a-b*, one or more capillaries 301, 301*aa*, 301*bb* that provide one or more channels 301*a*, 304*a*, 304*b*, and having a camera 314*a* and a light 314*b*.

Figure 31:
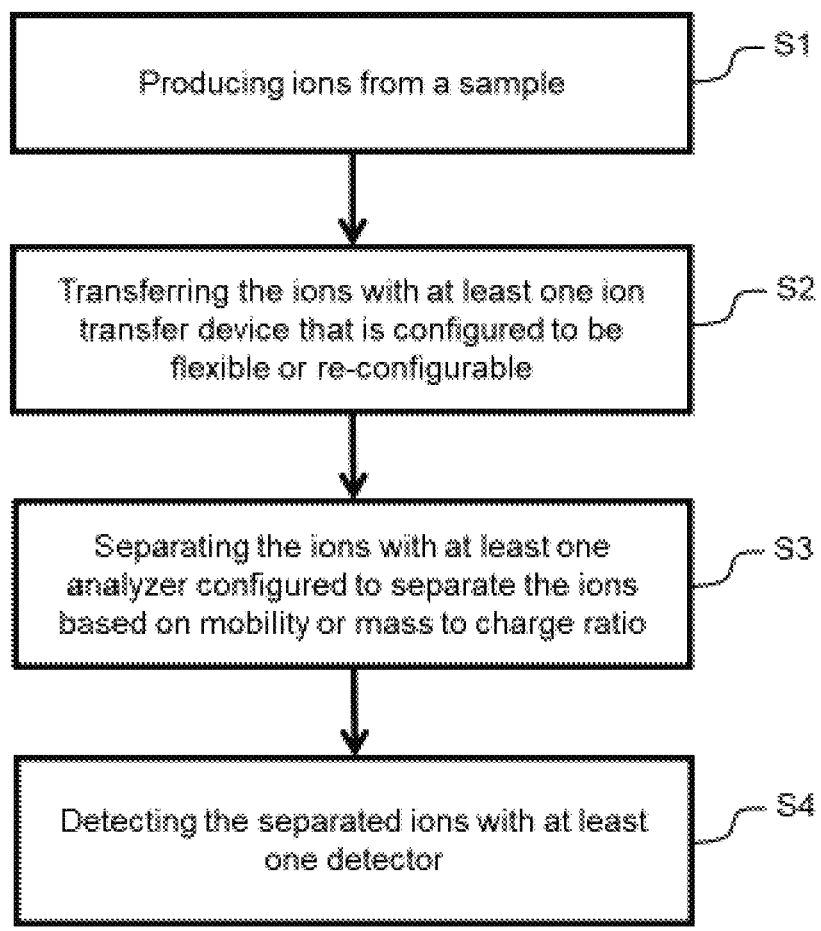
FIG. 31 shows a flow chart of a method for transferring ions with flexible or re-configurable ion transfer device in accordance with one or more embodiments of the present disclosure.

FIG. 31 shows a flow chart of a method of transferring ions with the flexible or re-configurable ion transfer device 20 in accordance with one or more aspects of the present disclosure. In one embodiment, a method for transferring ions includes producing ions from a sample in step S1, transferring the ions with at least one ion transfer device 20 that is configured to be flexible or re-configurable in step S2, the ion transfer device 20 having an enclosure, and a plurality of electrodes disposed at least in part inside the enclosure; separating the ions with at least one analyzer configured to separate the ions based on mobility or mass to charge ratio in step S3; and detecting the separated ions with at least one detector in step S4. The ions produced in S1 may be produced in vivo, from a surface or inner part of a living tissue on a human, animal, or a plant. The transferring of the ions may be realized by the method and application of the waveforms described in the present application.

Figure 32:
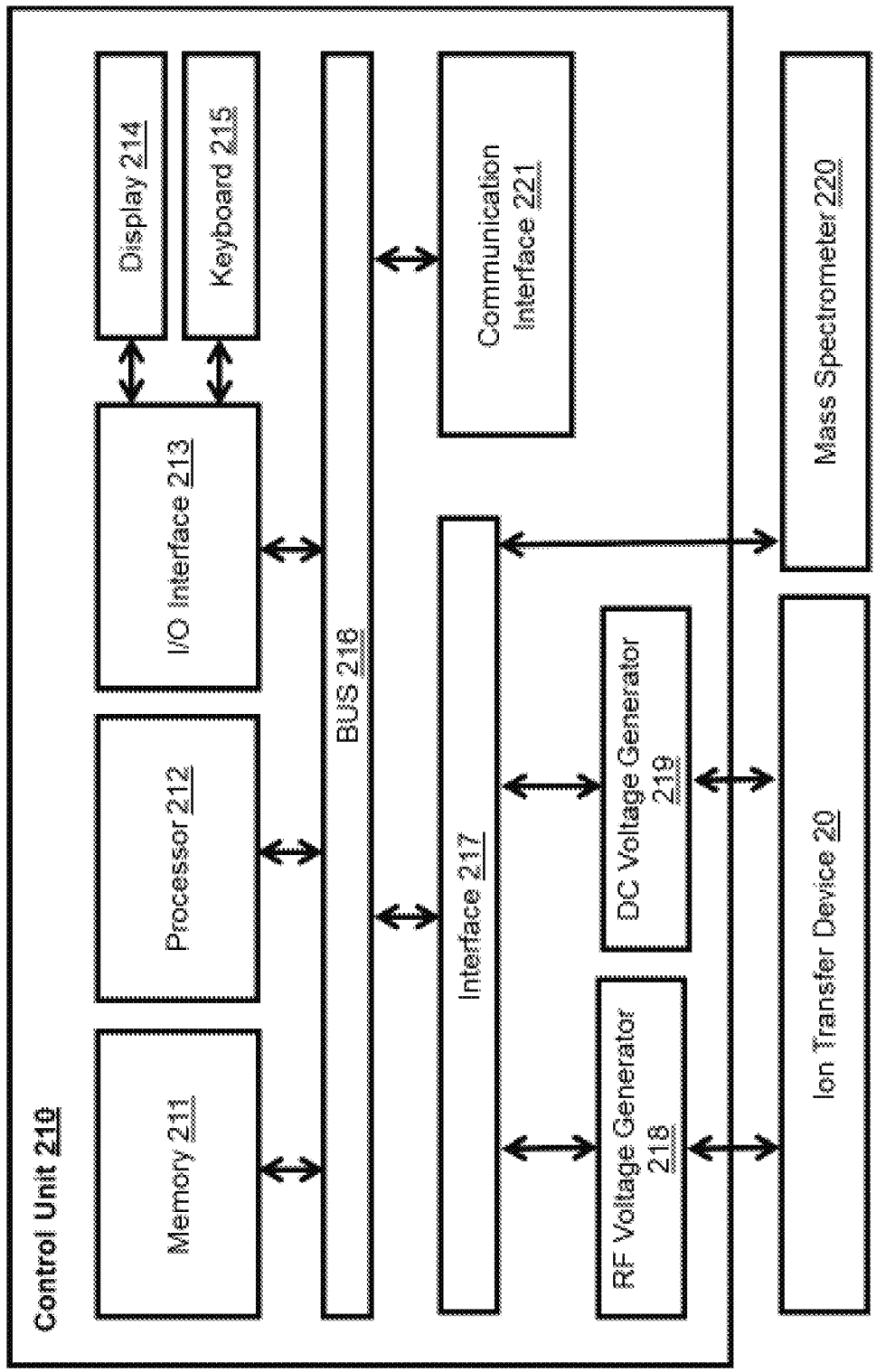
FIG. 32 shows a block diagram of control unit for ion transfer device upon which one or more embodiments of the present disclosure may be implemented.

FIG. 32 shows a block diagram of control unit 210 for ion transfer device 20 in more detail upon which an embodiment of the present disclosure may be implemented. The ion transfer device 20 may include or may be connected to one or more control units 210. The control unit 210 includes a memory 211, a processor 212, an input/output (I/O) interface 213 that is connected to a display 214 and a keyboard 215, an interface 217 that is connected to RF voltage generator 218 and DC voltage generator 219. The control unit 210 includes one or more memory 211, such as a random-access memory (RAM) or other dynamic storage device (e.g., dynamic RAM (DRAM), static RAM (SRAM), and synchronous DRAM (SDRAM)), coupled to the bus 216 for storing information and instructions to be executed by processor 212. In addition, the one or more memory 211 may be used for storing temporary variables or other intermediate information during the execution of instructions by the processor 212. The control unit 210 may further include a read only memory (ROM) or other static storage device (e.g., programmable ROM (PROM), erasable PROM (EPROM), and electrically erasable PROM (EEPROM)) coupled to the bus 216 for storing static information and instructions for the processor 212. The control unit 210 may further include a communication interface 221 coupled to the bus 216. The communication interface 221 provides a two-way data communication. For example, the communication interface 221 may be a network interface card to attach to any packet switched LAN. As another example, the communication interface 221 may be an asymmetrical digital subscriber line (ADSL) card, an integrated service digital network (ISDN) card, a Universal Serial Bus (USB), or a modem to provide a data communication connection to a corresponding type of communications line. A wired or wireless network may further be connected to the communication interface 221 connected to one or more computers that provide one or more operators and/or users a platform to communicate with the control unit 210. The control unit also includes an interface 217 that translates digital data received from the bus 216 and transmits instructions to one or more RF voltage generators 218 and one or more DC voltage generators 219, which provide the RF and DC voltages for operation of the ion transfer device 20. The RF voltage generators 218 and DC voltage generators 219 receive the instructions from the interface 217 and produce the voltages required by the ion transfer device 20. In one embodiment, the interface 217 may also be connected to a mass spectrometer that is connected to the ion transfer device 20 to, for example, synchronize to adjust the timing and multiplexing of the ion transfer process according to those disclosed in this application. The interface 217 may also be connected to one or more ionization probes to synchronize production and transfer of ions from a sample.

While the present disclosure has been described above with respect to a limited number of embodiments, those skilled in the art, having the benefit of this disclosure, will appreciate that other embodiments may be devised which do not depart from the scope of the invention as disclosed What claimed is:

1. An ion transfer device comprising:
   a first ion guide that receives ions from an inlet of the first ion guide and transfers the ions to an outlet of the first ion guide;
   a second ion guide that receives the ions from the outlet of the first ion guide through an inlet of the second ion guide and transfers the ions to an outlet of the second ion guide;
   one or more radio frequency (RF) voltage sources that supply one or more RF voltages, the one or more RF voltage sources being connected to the first ion guide and the second ion guide, the one or more RF voltages producing RF fields in the first ion guide and the second ion guide, the RF fields confining the ions within the first ion guide and the second ion guide; and
   one or more direct current (DC) voltage sources that supply one or more DC voltages, the one or more DC voltage sources being connected to the first ion guide and the second ion guide, the one or more DC voltages producing a first potential gradient in the first ion guide and a second potential gradient in the second ion guide,
   wherein the first potential gradient guides the ions within the first ion guide toward the outlet of the first ion guide, and the second potential gradient guides the ions within the second ion guide toward the outlet of the second ion guide,
   wherein the first potential gradient and the second potential gradient produced by the one or more DC voltages produce a potential barrier, the potential barrier preventing the ions in the first ion guide from entering the second ion guide,
   wherein the ions accumulate behind the potential barrier for a predetermined time period and form an ion packet,
   wherein an offset level of the first potential gradient is increased to reduce the potential barrier after the predetermined time period to move the ion packet from the first ion guide to the second ion guide, and
   wherein a plurality of ion packets periodically form in the first ion guide and move to the second ion guide at a frequency in a range from 10 Hz to 1000 Hz.

2. The ion transfer device according to claim 1, wherein the offset level of the first potential gradient in the first ion guide moves from a first offset level to a second offset level to increase the potential barrier is increased after a second predetermined time period to form a next ion packet in the first ion guide.

3. The ion transfer device according to claim 1, wherein:
   the first ion guide is located in a first chamber, a pressure of the first chamber being maintained at a first pressure level, and
   the second ion guide is located in a second chamber, a pressure of the second chamber being maintained at a second pressure level.

4. The ion transfer device according to claim 1, wherein the predetermined time period is in a range from 0.01 to 100 milliseconds.

5. The ion transfer device according to claim 1, wherein the ion packet moves from the first ion guide to the second ion guide if a potential level of the first potential gradient at the outlet of the first ion guide is equal to or greater than a potential level of the second potential gradient at the inlet of the second ion guide.

6. The ion transfer device according to claim 1, wherein the ions accumulate within the first ion guide in an accumulation location along a longitudinal axis of the first ion guide that is closer to the outlet of the first ion guide than to the inlet of the first ion guide.

7. The ion transfer device according to claim 1, wherein the ions move from the inlet of the second ion guide toward the outlet of the second ion guide by the second potential gradient.

8. The ion transfer device according to claim 1, wherein the ion transfer device receives the ions from an ion source, accumulates the ions to form the ion packet, and delivers the ion packet to a mass analyzer, the mass analyzer being a time-of-flight mass analyzer, an ion trap mass analyzer, or an electrostatic trapping mass analyzer.

9. The ion transfer device according to claim 1, wherein the potential barrier is periodically increased by moving the first potential gradient towards a second offset level and decreased by moving the first potential gradient towards a first offset level, the first potential gradient having the same slope in the first offset level and the second offset level.

10. The ion transfer device according to claim 1, wherein the ions move from the first ion guide to the second ion guide if the potential barrier between the first ion guide and the second ion guide is equal to or less than zero.

11. The ion transfer device according to claim 1, wherein the second ion guide receives the ions from the first ion guide as the ion packet, and guides the ions to the outlet of the second ion guide.

12. The ion transfer device according to claim 1, wherein the inlet and the outlet of the first ion guide are located at two ends of the first ion guide.

13. The ion transfer device according to claim 1, wherein the first ion guide and the second ion guide are multipole ion guides or stacked-ring ion guides.

14. The ion transfer device according to claim 1, wherein the first potential gradient has a negative slope from the inlet toward the outlet of the first ion guide, and the second potential gradient has a negative slope from the inlet toward the outlet of the second ion guide.

15. The ion transfer device according to claim 1, wherein a frequency of the one or more RF voltages supplied to the first ion guide and the second ion guide are in a range from 0.1 to 10 MHz.

16. The ion transfer device according to claim 1, wherein the first ion guide accumulates and transfers the ions to the second ion guide periodically and every 1 to 100 milliseconds.

17. The ion transfer device according to claim 1, wherein the one or more DC voltages have time-varying offset voltages to periodically move the first potential gradient between a first potential level and a second potential level while maintaining a slope of the first potential gradient, the time-varying offset voltages having a ramp, pulse, triangular, or square waveform.

18. The ion transfer device according to claim 1, wherein the first ion guide or the second ion guide is maintained at a pressure level with background gas, and the background gas cools the ions by collisional cooling.

19. The ion transfer device according to claim 1, wherein the ions are produced by an ion source, the ion source being an electrospray ion source, and the ions being produced from biological samples.

20. The ion transfer device according to claim 1, wherein a third ion guide having an outlet is provided upstream the first ion guide, the first ion guide receiving the ions from the outlet of the third ion guide.

21. A mass spectrometry system comprising:
an ion source that produces ions;
a first ion guide that receives the ions from an inlet of the first ion guide and transfers the ions to an outlet of the first ion guide;
a second ion guide that receives the ions from the outlet of the first ion guide through an inlet of the second ion guide and transfers the ions to an outlet of the second ion guide;
one or more RF voltage sources that supply one or more RF voltages, the one or more RF voltage sources being connected to the first ion guide and the second ion guide, the one or more RF voltages producing RF fields in the first ion guide and the second ion guide, the RF fields confining the ions within the first ion guide and the second ion guide;
one or more DC voltage sources that supply one or more DC voltages, the one or more DC voltage sources being connected to the first ion guide and the second ion guide, the one or more DC voltages producing a first potential gradient in the first ion guide and a second potential gradient in the second ion guide; and
a mass analyzer that separates the ions based on mass to charge ratio of the ions,
wherein the first potential gradient guides the ions within the first ion guide toward the outlet of the first ion guide, and the second potential gradient guides the ions within the second ion guide toward the outlet of the second ion guide,
wherein the first potential gradient and the second potential gradient produced by the one or more DC voltages produce a potential barrier, the potential barrier preventing the ions in the first ion guide from entering the second ion guide,
wherein the ions accumulate behind the potential barrier for a predetermined time period and form an ion packet,
wherein an offset level of the first potential gradient is increased to reduce the potential barrier after the predetermined time period to move the ion packet from the first ion guide to the second ion guide, and
wherein a plurality of ion packets periodically form in the first ion guide and move to the second ion guide at a frequency in a range from 10 Hz to 1000 Hz.

22. The mass spectrometry system according to claim 21, wherein:
the first ion guide is located in a first chamber, a pressure of the first chamber being maintained at a first pressure level, and
the second ion guide is located in a second chamber, a pressure of the second chamber being maintained at a second pressure level.

23. The mass spectrometry system according to claim 21, wherein the predetermined time period is in a range from 0.01 to 100 milliseconds.

24. The mass spectrometry system according to claim 21, wherein the ion packet moves from the first ion guide to the second ion guide if a potential level of the first potential gradient at the outlet of the first ion guide is equal to or greater than a potential level of the second potential gradient at the inlet of the second ion guide.

25. The mass spectrometry system according to claim 21, wherein the ions accumulate within the first ion guide in an accumulation location along a longitudinal axis of the first ion guide that is closer to the outlet of the first ion guide than to the inlet of the first ion guide.

26. The mass spectrometry system according to claim 21, wherein the ions move from the inlet of the second ion guide toward the outlet of the second ion guide by the second potential gradient.

27. The mass spectrometry system according to claim 21, wherein the ions move from the first ion guide to the second ion guide if a potential level of the first potential gradient at the outlet of the first ion guide is equal to or greater than a potential level of the second potential gradient at the inlet of the second ion guide.

28. The mass spectrometry system according to claim 21, wherein the ions within the first ion guide move toward the outlet of the first ion guide by the first potential gradient.

29. The mass spectrometry system according to claim 21, wherein the mass analyzer is a time-of-flight mass analyzer, an ion trap mass analyzer, or an electrostatic trapping mass analyzer.

30. The mass spectrometry system according to claim 21, wherein the potential barrier is periodically increased and decreased by moving up and down the one or more DC voltages.

31. The mass spectrometry system according to claim 21, wherein accumulated ions move from the first ion guide to the second ion guide if the potential barrier between the first ion guide and the second ion guide is equal to or less than zero.

32. The mass spectrometry system according to claim 21, wherein the second ion guide receives accumulated ions from the first ion guide as the ion packet, and transfers the ions to the outlet of the second ion guide.

33. The mass spectrometry system according to claim 21, wherein the inlet and the outlet of the first ion guide are located at two ends of the first ion guide.

34. The mass spectrometry system according to claim 21, wherein the first ion guide and the second ion guide are multipole ion guides or stacked-ring ion guides.

35. The mass spectrometry system according to claim 21, wherein the first potential gradient has a negative slope from the inlet toward the outlet of the first ion guide, and the second potential gradient has a negative slope from the inlet toward the outlet of the second ion guide.

36. The mass spectrometry system according to claim 21, wherein a frequency of the one or more RF voltages supplied to the first ion guide and the second ion guide are in a range from 0.1 to 10 MHz.

37. The mass spectrometry system according to claim 21, wherein the first ion guide accumulates and transfers the ions to the second ion guide periodically and every 1 to 100 milliseconds.

38. The mass spectrometry system according to claim 21, wherein the one or more DC voltages have time-varying offset voltages to periodically move the first potential gradient between a first potential level and a second potential level while maintaining a slope of the first potential gradient, the time-varying offset voltages having a ramp, pulse, triangular, or square waveform.

39. The mass spectrometry system according to claim 21, wherein the first ion guide or the second ion guide is maintained at a pressure level with background gas, and the background gas cools the ions by collisional cooling.

40. The mass spectrometry system according to claim 21, wherein the ion source is an electrospray ion source, and the ions are produced from biological samples.

41. The mass spectrometry system according to claim 21, wherein a third ion guide having an outlet is provided upstream the first ion guide, and the first ion guide receives the ions from the outlet of the third ion guide.

42. A method for transferring ions, the method comprising:
- providing RF electric fields in a first ion guide and a second ion guide for confining the ions within the first ion guide and the second ion guide;
- providing a first potential gradient in the first ion guide for guiding the ions entering from an inlet of the first ion guide toward an outlet of the first ion guide;
- providing a second potential gradient in the second ion guide for guiding the ions entering from an inlet of the second ion guide toward an outlet of the second ion guide;
- producing a potential barrier with the first potential gradient and the second potential gradient for preventing the ions in the first ion guide from entering the second ion guide;
- accumulating the ions behind the potential barrier for a predetermined time period to form an ion packet; and
- reducing the potential barrier by increasing an offset level of the first potential gradient after the predetermined time period to move the ion packet from the first ion guide to the second ion guide,
- wherein a plurality of ion packets periodically form in the first ion guide and move to the second ion guide at a frequency in a range from 10 Hz to 1000 Hz.

43. The method according to claim 42, wherein the transferring of the ions from the first ion guide to the second ion guide is efficient with 50% to 100% of accumulated ions in the first ion guide moving to the second ion guide.

44. The method according to claim 42, wherein the predetermined time period is in a range from 0.01 to 100 milliseconds.

45. The method according to claim 42, wherein, during the accumulating, the ions accumulate within the first ion guide in an accumulation location along a longitudinal axis of the first ion guide that is closer to the outlet of the first ion guide than to the inlet of the first ion guide.

46. The method according to claim 42, wherein the ions move from the first ion guide to the second ion guide if a level of the first potential gradient at the outlet of the first ion guide is equal to or greater than a level of the second potential gradient at the inlet of the second ion guide.

47. The method according to claim 42, wherein, during the transferring, the ions move from the first ion guide to the second ion guide by the first potential gradient if a potential level of the first potential gradient at the outlet of the first ion guide is equal to or greater than a potential level of the second potential gradient at the inlet of the second ion guide.

48. The method according to claim 42, wherein the first ion guide accumulates and transfers the ions and transferred to the second ion guide periodically and every 1 to 100 milliseconds.

49. The method according to claim 42, wherein there is no conductance limiting orifice in a trajectory of the ions moving from the first ion guide to the second ion guide.

50. The method according to claim 42, wherein the ions in the second ion guide are delivered to a mass analyzer, the mass analyzer being a time-of-flight mass analyzer, an ion trap mass analyzer, or an electrostatic trapping mass analyzer.

51. The method according to claim 42, wherein the ions are produced by an ion source, the ion source being an electrospray ion source, and the ions being produced from biological samples.

52. The method according to claim 42, wherein the first ion guide and the second ion guide are maintained at different pressure levels or vacuum levels.

53. The method according to claim 42, further comprising:
- providing background gas inside at least one of the first ion guide and the second ion guide for collisional cooling of the ions.

54. The method according to claim 42, wherein background gas is provided in the first ion guide, the second ion guide, or both the first ion guide and the second ion guide for collisional cooling of the ions, the background gas being nitrogen, helium, or argon.

55. The method according to claim 42, wherein:
- one or more RF voltage sources supply one or more RF voltages to the first ion guide and the second ion guide for producing the RF electric fields, and
- one or more DC voltage sources supply one or more DC voltages to the first ion guide for producing the first potential gradient, and to the second ion guide for producing the second potential gradient.

56. The method according to claim 42, wherein reducing the potential barrier moves the accumulated ions from the first ion guide into the second ion guide by the first potential gradient.

57. The method according to claim 42, wherein a longitudinal axis of the first ion guide and a longitudinal axis of the second ion guide are on a same line, and the first potential gradient of the first ion guide pushes the ions axially toward the second ion guide.

58. The method according to claim 42, wherein the ions entering the second ion guide move away from the inlet of the second ion guide by the second potential gradient.

59. The method according to claim 42, wherein the first ion guide and the second ion guide are multipole ion guides, stacked-ring ion guides, or a combination of multipole and stacked-ring ion guides.

60. The method according to claim 42, wherein a third ion guide having an outlet is provided upstream the first ion guide, and the first ion guide receives the ions from the outlet of the third ion guide.

61. The method according to claim 42, wherein the RF electric fields in the first ion guide and the second ion guide are produced by supplying RF voltages of a same frequency to the first ion guide and the second ion guide, the same frequency being in a range from 0.05 MHz to 10 MHz.

62. A mass spectrometry system comprising:
- an ion source that produces ions;
- an ion funnel that includes a plurality of plate electrodes, each plate electrode having a center hole with an inner diameter that is greater than or equal to three times the inter-electrode spacing of the plurality of plate electrodes;
- a first ion guide that receives the ions from an inlet of the first ion guide and transfers the ions to an outlet of the first ion guide;
- a second ion guide that receives the ions from the outlet of the first ion guide through an inlet of the second ion guide and transfers the ions to an outlet of the second ion guide;
- one or more RF voltage sources that supply one or more RF voltages, the one or more RF voltage sources being connected to the first ion guide and the second ion guide, the one or more RF voltages producing RF fields in the first ion guide and the second ion guide, the RF fields confining the ions within the first ion guide and the second ion guide;
- one or more DC voltage sources that supply one or more DC voltages, the one or more DC voltage sources being connected to the first ion guide and the second ion guide, the one or more DC voltages producing a first potential gradient in the first ion guide and a second potential gradient in the second ion guide; and a mass analyzer that separates the ions based on mass to charge ratio of the ions, wherein the first potential gradient guides the ions within the first ion guide toward the outlet of the first ion guide, and the second potential gradient guides the ions within the second ion guide toward the outlet of the second ion guide, wherein the first potential gradient and the second potential gradient produced by the one or more DC voltages produce a potential barrier, the potential barrier preventing the ions in the first ion guide from entering the second ion guide, wherein the ions accumulate behind the potential barrier for a predetermined time period and form an ion packet, wherein an offset level of the first potential gradient is increased to reduce the potential barrier after the predetermined time period to move the ion packet from the first ion guide to the second ion guide, and wherein a plurality of ion packets periodically form in the first ion guide and move to the second ion guide at a frequency in a range from 10 Hz to 1000 Hz.

* * * * *